United States Patent
Komatsu

(10) Patent No.: US 11,647,711 B2
(45) Date of Patent: May 16, 2023

(54) BROCCOLI PLANT

(71) Applicant: Takii & Company Limited, Kyoto (JP)

(72) Inventor: Takayuki Komatsu, Kyoto (JP)

(73) Assignee: TAKII & COMPANY LIMITED, Kyoto (JP)

( * ) Notice: Subject to any disclaimer, the term of this patent is extended or adjusted under 35 U.S.C. 154(b) by 0 days.

(21) Appl. No.: 17/392,255

(22) Filed: Aug. 2, 2021

(65) Prior Publication Data

US 2022/0046882 A1 Feb. 17, 2022

(30) Foreign Application Priority Data

Aug. 14, 2020 (JP) .............................. JP2020-136913

(51) Int. Cl.
*A01H 5/10* (2018.01)
*A01H 6/20* (2018.01)
*A01H 5/02* (2018.01)

(52) U.S. Cl.
CPC ............... *A01H 6/203* (2018.05); *A01H 5/02* (2013.01)

(58) Field of Classification Search
CPC ...................................................... A01H 6/203
USPC ......................................................... 800/260
See application file for complete search history.

(56) References Cited

U.S. PATENT DOCUMENTS

2013/0067610 A1\* 3/2013 Mero ..................... A01H 5/00
800/260

OTHER PUBLICATIONS

Adhikar et al., "Application of molecular markers in plant genome analysis: a review," Nucleus, 60 (3): 283-297 (2017).
Dunwell, "Haploids in flowering plants: origins and exploitation," Plant Biotechnology Journal, 8: 377-424 (2010).
Guimaraes et al., "Marker-Assisted Selection: Current status and future perspectives in crops, livestock, forestry and fish," Food and Agriculture Organization of the United Nations, Rome (2007).
Hansen et al., "Genetic analysis of protoplast regeneration ability in Brassica oleracea," Plant Cell, Tissue and Organ Culture, 58: 127-132 (1999).
Kim et al., "Callus Induction and Plant Regeneration from Broccoli (*Brassica oleracea* var. italica) for Transformation," Journal of Plant Biology, 45 (3): 177-181 (2002).
Kumar et al., "In vitro Plant Propagation: A Review," Journal of Forest Science, 27 (2): 61-72 (2011).
Mao et al., "Gene editing in plants: progress and challenges," National Science Review, 6: 421-437 (2019).
Megersa et al., "Propagation Methods of Selected Horticultural Crops by Specialized Organs: Review," Journal of Horticulture, 4 (2): 1000198 (2017).
Parkin et al., "Transcriptome and methylome profiling reveals relics of genome dominance in the mesopolyploid Brassica oleracea," Genome Biology, 15: R77 (2014).
Ravanfar et al., "Plant regeneration of *Brassica oleracea* subsp. italica (Broccoli) CV Green Marvel as affected by plant growth regulators," African Journal of Biotechnology, 8(11): 2523-2528 (2009).
Suzuki et al., "Characterization of Brassica S-haplotypes lacking S-locus glycoprotein," FEBS Letters, 482: 102-108 (2000).

\* cited by examiner

*Primary Examiner* — Keith O. Robinson

(74) *Attorney, Agent, or Firm* — Morgan, Lewis & Bockius LLP

(57) ABSTRACT

The present invention provides a new broccoli variety. The broccoli plant of the present invention includes a broccoli plant identified by Accession No. FERM BP-22393 or a progeny line thereof.

25 Claims, 6 Drawing Sheets

Specification includes a Sequence Listing.

Characteristic No. 3: Leaf: attitude

Note 3: semi-erect

Note 5: horizontal

Note 7: semi-pendulous

Characteristic No.15 : Head: length of branching

Note 3: short

Note 5: medium

Note 7: long

Characteristic No.18 : Head: shape in longitudinal section

Note 1: circular

Note 2: transverse broad elliptic

Note 3: transverse medium elliptic

Note 4: transverse narrow elliptic

Note 5: triangular

Characteristic No. 23 : Head: knobbling

Note 3: fine

Note 5: medium

Note 7: coarse

Whole view of cultivation area

Whole plant

BROCCOLI PLANT

SEQUENCE LISTING SUBMISSION VIA EFS-WEB

A computer readable text file, entitled "SequenceListing.txt," created on Jul. 30, 2021 with a file size of 69,119 bytes contains the sequence listing for this application and is hereby incorporated by reference in its entirety.

TECHNICAL FIELD

Related Application

This application claims priority from Japanese Patent Application No. 2020-136913 filed on Aug. 14, 2020. The entire disclosure of this Japanese patent application is incorporated herein by reference.

The present invention relates to a broccoli plant.

Background Art

Broccoli plants are cultivated in winter, harvesting from December to January. However, in winter cultivation, broccoli plants tend to grow slowly, and anthocyanin coloration often occurs. Broccoli plants colored with anthocyanin have a problem of low merchantability.

Therefore, there is a need for broccoli plants with superior characteristics.

SUMMARY OF INVENTION

Technical Problem

With the foregoing in mind, it is one objective of the present invention to provide a new broccoli plant.

Solution to Problem

In order to achieve the above objective, the present invention provides a broccoli plant including a broccoli plant identified by Accession No. FERM BP-22393.

The present invention also provides a method for producing a broccoli plant, including the step of self-crossing the broccoli plant according to the present invention.

The present invention also provides a method for producing a broccoli plant, including the step of crossing the broccoli plant according to the present invention with another broccoli plant.

Advantageous Effects of Invention

According to the present invention, a new broccoli plant can be provided.

DESCRIPTION OF EMBODIMENTS

<Broccoli Plant>

Figure 1A:
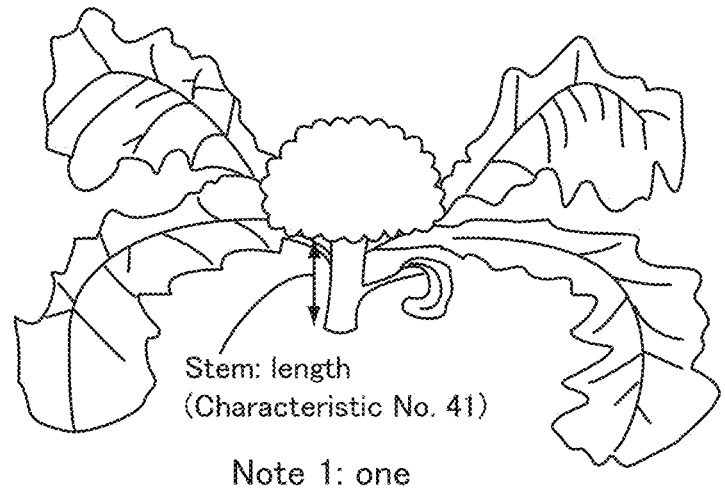
FIGS. 1A and 1B are schematic diagrams showing an example of the number of stems of a broccoli plant and an example of the length of a stem of a broccoli plant, respectively.
Figure 1B:
Figure 2A:
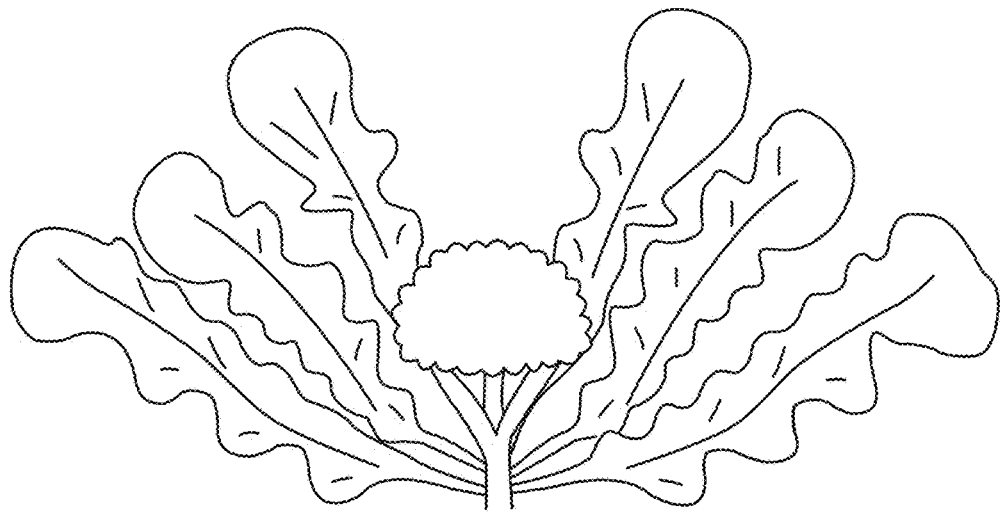
FIGS. 2A to 2C are schematic diagrams showing examples of the attitude of leaves of a broccoli plant.
Figure 2B:
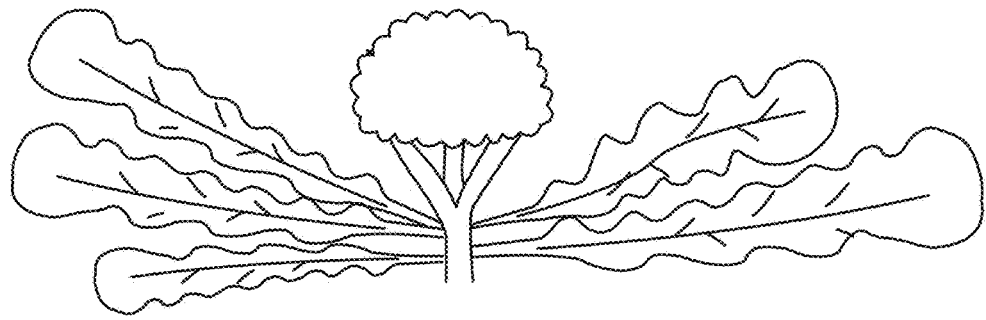
Figure 2C:
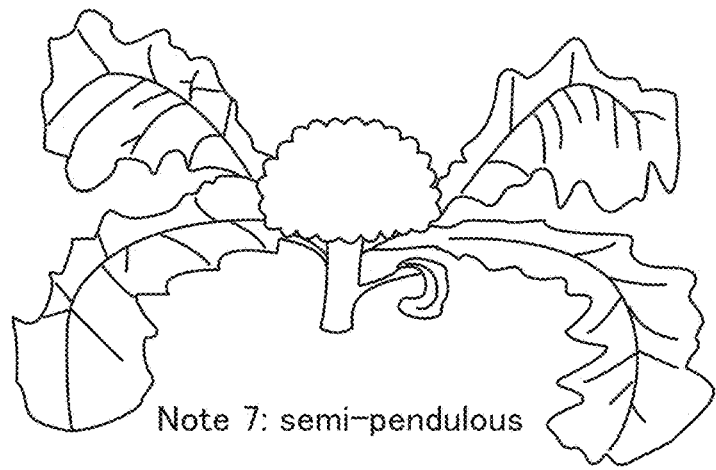
Figure 3A:
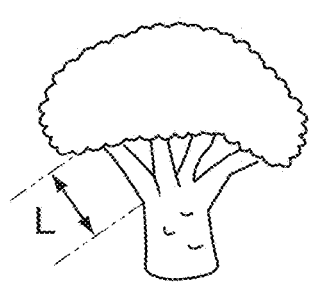
FIGS. 3A to 3C are schematic diagrams showing examples of the length of branching of a head of a broccoli plant, the shape in a longitudinal section of the head, and the knobbling of the head, respectively.
Figure 3A:
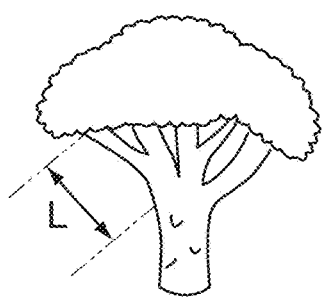
Figure 3A:
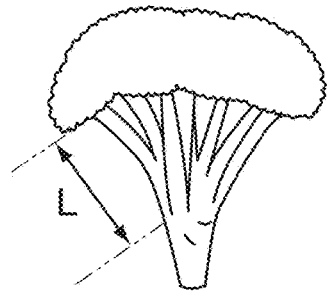
Figure 3B:
Figure 3B:
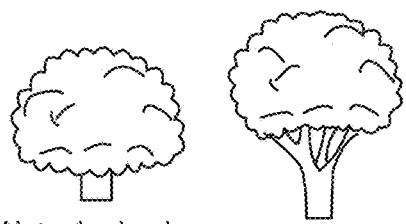
Figure 3B:
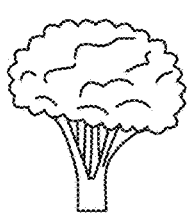
Figure 3B:
Figure 3B:
Figure 3C:
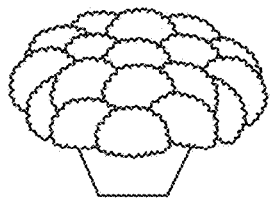
Figure 3C:
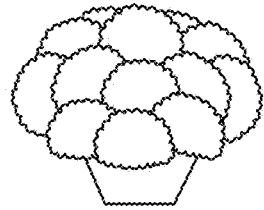
Figure 3C:
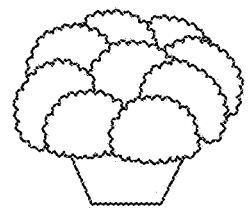
Figure 4:
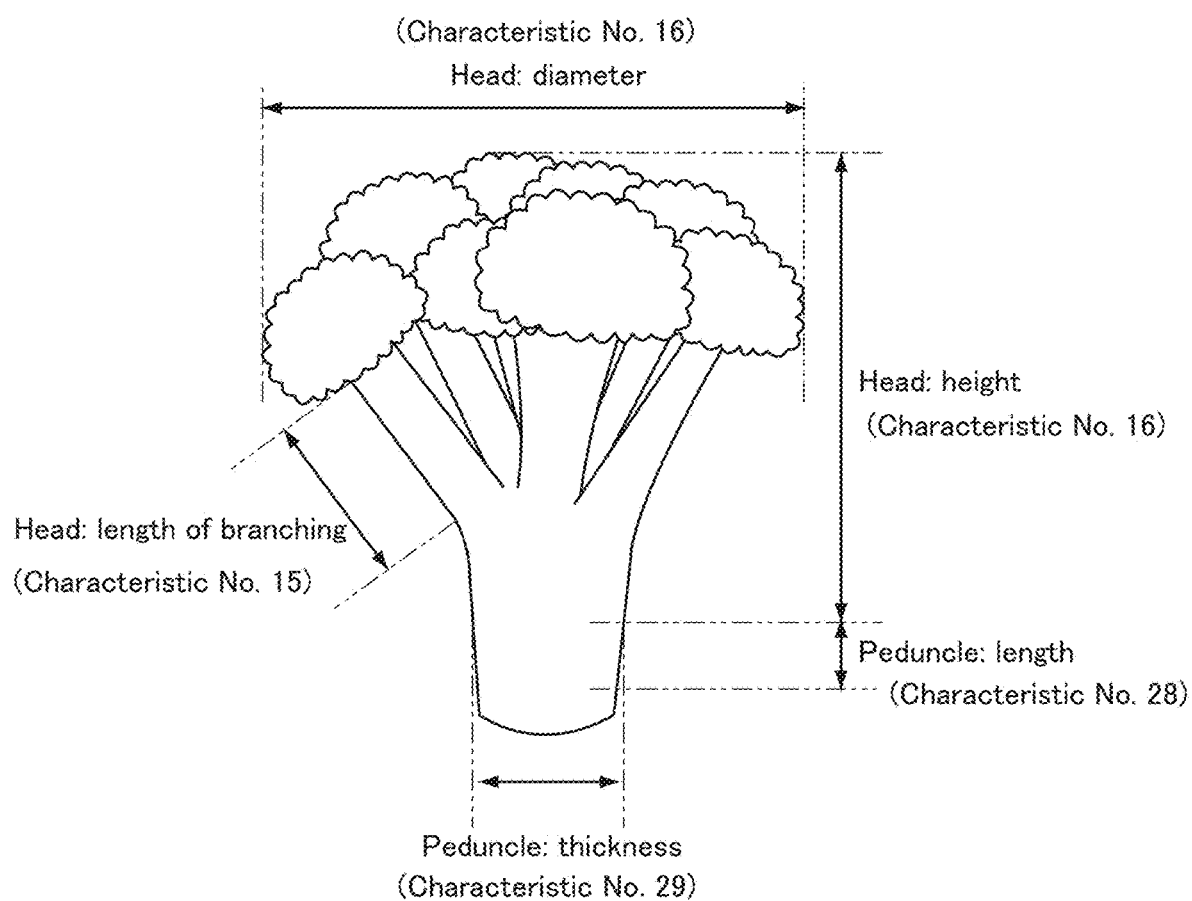
FIG. 4 is a schematic diagram showing an example of the length of branching of a head of a broccoli plant, the size of the head, the length of a peduncle of the head, and the thickness of the peduncle of the head.
Figure 5:
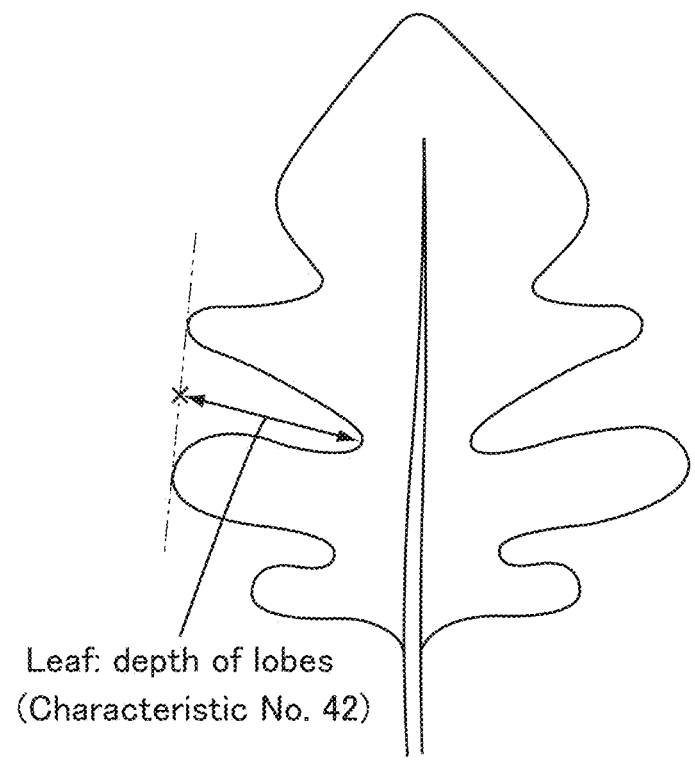
FIG. 5 is a schematic diagram showing an example of the depth of a lobe of a leaf of a broccoli plant.

The broccoli plant of the present invention includes a broccoli plant identified by Accession No. FERM BP-22393 or a progeny line thereof. The broccoli plant of the present invention is characterized in that it includes a broccoli plant identified by Accession No. FERM BP-22393 or a progeny line thereof, and other configurations or conditions are not particularly limited.

In the present invention, a "broccoli plant" is a plant classified into *Brassica oleracea* var *italica* of *Brassica oleracea* of *Brassica*. Examples of the broccoli plant include *Brassica oleracea* var. *italica* (*Brassica oleracea* L. convar. *Botrytis* (L.) Alef. var. *italica*) and *Brassica oleracea* var. *cymosa* Duch. (*Brassica oleracea* L. convar. *botrytis* (L.) Alef var. *cymosa* Duch.). The broccoli plant may be a hybrid with a related species or a wild species, for example.

In the present invention, a "broccoli plant for cultivation," a "broccoli variety for cultivation," or a "broccoli for cultivation" is a broccoli plant or a variety thereof, a breeding line, or a cultivar that is cultivated by humans and is excellent in cultivation. The "broccoli plant for cultivation," the "broccoli variety for cultivation," or the "broccoli for cultivation" may be a hybrid thereof, a hybrid with another broccoli variant, or a hybrid with another *Brassica oleracea*.

The term "plant," as used in the present invention, may refer to either a plant individual representing the whole plant or a part of the plant individual (plant part). Examples of the "plant" include plant cells, plant protoplasts, plant cell cultures or tissue cultures capable of regenerating plants, plant calli, plant clumps, plant cells isolated from plants or plant parts, leaves, pollens, embryos, cotyledons, hypocotyls, roots, root tips (tips of roots), anthers, pistils, flowers, ovaries, ovules, seeds, fruits, stems, and seedlings. The part of the plant individual may be any of organs, tissues, cells, and propagules, for example. Examples of the organs include petals, corollas, flowers, leaves, seeds, fruits, stems, and roots. The tissue is a part of the organ, for example. Specific examples of the part of the plant individual include microspores, flowers, flower buds, pistils, anthers, pollens, ovaries, embryos, ovules, hypocotyls, embryonic sacs, egg cells, cuttings, roots, root tips, trunks, stems, leaves, pedicles, leaf marrow, cotyledons, cells, meristematic cells, protoplasts, and seeds. The pollens may be mature pollens or immature pollens. The part of the plant individual can be, for example, derived from a plant at any growth stage, and may be derived from, for example, a pre-rooting individual, a post-rooting individual, a seedling, a cutting, or a mature individual, and the like. The part of the plant body may be one type of organ, tissue, and/or cell, or two or more types of organs, tissues, and/or cells, for example.

<Deposit Line>

The broccoli plant of the present invention may be, for example, a broccoli plant deposited under Accession No. FERM BP-22393 (deposited line) or a progeny line thereof.

The information on the deposit is shown below. Hereinafter, the deposited line is also referred to as a broccoli variety Takii 12.
Type of deposit: International deposit
Name of depository institution: National Institute of Technology and Evaluation, International Patent Organism Depositary; NITE-IPOD
Address: 2-5-8-120, Kazusakamatari, Kisarazu-shi, Chiba 292-0818, Japan
Accession No.: FERM BP-22393
Identifying designation: Takii 12
Date of acceptance: Jul. 30, 2020

The deposited lines exhibit morphological and physiological characteristics as described in Tables 1A to 1C below, for example. In Tables 1A and 1B, the morphological and physiological characteristics are based on Japanese prototypes in 2013. In Tables 1A and 1B, the morphological and physiological characteristics are evaluated based on the Broccoli Variant Test Guideline (April 2012) published by the Ministry of Agriculture, Forestry and Fisheries of Japan (MAFF). In Table 1C, the morphological and physiological characteristics are evaluated based on the criteria to be described below. Regarding the morphological and physiological characteristics, reference can be made to FIGS. 1A through 5.

TABLE 1A

Characteristics of deposited line

| Characteristic No. | Characteristics | Deposited Line |
|---|---|---|
| 1 | Plant: number of stems | One |
| 2 | Plant: height | Medium |
| 3 | Leaf: attitude | Semi-erect |
| 4 | Leaf: length | Medium |
| 5 | Leaf: width | Medium |
| 6 | Leaf: number of lobes | Many |
| 7 | Leaf blade: color | Gray-green |
| 8 | Leaf blade: intensity of color | Medium |
| 9 | Leaf blade: anthocyanin coloration | Absent |
| 10 | Leaf blade: undulation of margin | Medium |
| 11 | Leaf blade: dentation of margin | Weak |
| 12 | Leaf blade: blistering | Weak |
| 13 | Petiole: anthocyanin coloration | Absent |
| 14 | Petiole: length | Medium |
| 15 | Head: length of branching | Short |
| 16 | Head: size | Medium |
| 17 | Head: weight | Heavy |
| 18 | Head: shape in longitudinal section | Transverse broad elliptic |
| 19 | Head: color | Green |
| 20 | Head: intensity of color | Medium |
| 21 | Head: anthocyanin coloration | Present |
| 22 | Head: intensity of anthocyanin coloration | Weak |
| 23 | Head: knobbling | Fine |
| 24 | Head: texture | Medium |
| 25 | Head: firmness | Firm |
| 26 | Head: conspicuousness of spiral pattern | Obscure |
| 27 | Head: bracts | Absent |
| 28 | Peduncle: length | Short |
| 29 | Peduncle: thickness | Thick |

TABLE 1B

Characteristics of deposited line

| Characteristic No. | Characteristics | Deposited Line |
|---|---|---|
| 30 | Peduncle: hardness | Medium |
| 31 | Peduncle: color | Green |

TABLE 1B-continued

Characteristics of deposited line

| Characteristic No. | Characteristics | Deposited Line |
|---|---|---|
| 32 | Plant: secondary heads | Absent |
| 34 | Flower: color | Yellow |
| 35 | Flower: intensity of yellow color | Medium |
| 36 | Time of harvest | Late |
| 37 | Time of beginning of flowering | Medium |
| 38 | Male sterility | Absent |

TABLE 1C

Characteristics of deposited line

| Characteristic No. | Characteristics | Deposited Line |
|---|---|---|
| 40 | Leaf: number | Many |
| 41 | Stem: length | Short |
| 42 | Leaf: depth of lobes | Deep |

(Characteristic No. 1)

"Plant: number of stems" refers to the number of stems immediately before the time of harvest and can be evaluated by visual observation. "Plant: number of stems" can be evaluated on the basis of Note 1 (one) or Note 2 (more than one, e.g., Var.: GREEN COMET). The time of harvest refers to the time at which half of the individuals are in the optimal time of harvest.

(Characteristic No. 2)

"Plant: height" refers to the plant height (cm) at the time of harvest. "Plant: height" can be evaluated on the basis of Note 3 (low, e.g., Var.: NAKAZATO WASE), Note 5 (medium, e.g., Var.: WASE MIDORI), or Note 7 (high, e.g., Var.: NAKATE MIDORI).

(Characteristic No. 3)

"Leaf: attitude" refers to the angle (attitude) of the leaves at the beginning of head formation (head appearing stage) and can be evaluated by visual observation. "Leaf: attitude" can be evaluated on the basis of Note 3 (semi-erect), Note 5 (horizontal, e.g., Var.: OKA MIDORI), or Note 7 (semi-pendulous).

(Characteristic No. 4)

"Leaf: length" refers to the length (cm) of the leaf, including the petiole. "Leaf: length" can be evaluated on the basis of Note 3 (short, e.g., Var.: OKA MIDORI), Note 5 (medium, e.g., Var.: WASE MIDORI), or Note 7 (long, e.g., Var.: NAKATE MIDORI).

(Characteristic No. 5)

"Leaf: width" refers to the width (cm) of the leaf "Leaf: width" can be evaluated on the basis of Note 3 (narrow, e.g., Var.: OKA MIDORI), Note 5 (medium, e.g., Var.: GREEN COMET), or Note 7 (broad, e.g., Var.: NAKATE MIDORI).

(Characteristic No. 6)

"Leaf: number of lobes" refers to the number of lobes of the leaf and can be evaluated by visual observation. "Leaf: number of lobes" can be evaluated on the basis of Note 3 (few), Note 5 (medium, e.g., Var.: WASE MIDORI), or Note 7 (many, e.g., Var.: NAKATE MIDORI).

(Characteristic No. 7)

"Leaf blade: color" refers to the color of the leaf blade and can be evaluated by visual observation. "Leaf blade: color" can be evaluated on the basis of Note 1 (green, e.g., Var.: GREEN COMET), Note 2 (gray-green, e.g., Var.: OKA MIDORI), or Note 3 (blue-green).

(Characteristic No. 8) "Leaf blade: intensity of color" refers to the intensity of the color of the leaf blade and can be evaluated by visual observation. "Leaf blade: intensity of color" can be evaluated on the basis of Note 3 (light), Note 5 (medium, e.g., Var.: GREEN COMET), or Note 7 (dark, e.g., Var.: OKA MIDORI).

(Characteristic No. 9) "Leaf blade: anthocyanin coloration" refers to the anthocyanin coloration of the leaf blade and can be evaluated by visual observation. "Leaf blade: anthocyanin coloration" can be evaluated on the basis of Note 1 (absent) or Note 9 (present, e.g., Var.: NAKATE MIDORI).

(Characteristic No. 10) "Leaf blade: undulation of margin" refers to the intensity of the undulation of the margin of the leaf blade and can be evaluated by visual observation. "Leaf blade: undulation of margin" can be evaluated on the basis of Note 3 (weak), Note 5 (medium), or Note 7 (strong).

(Characteristic No. 11) "Leaf blade: dentation of margin" refers to the intensity of the dentation of the margin of the leaf blade and can be evaluated by visual observation. "Leaf blade: dentation of margin" can be evaluated on the basis of Note 3 (weak), Note 5 (medium), or Note 7 (strong, e.g., Var.: NAKATE MIDORI).

(Characteristic No. 12) "Leaf blade: blistering" refers to the intensity of the blistering of the leaf blade and can be evaluated by visual observation. "Leaf blade: blistering" can be evaluated on the basis of Note 3 (weak), Note 5 (medium), or Note 7 (strong).

(Characteristic No. 13) "Petiole: anthocyanin coloration" refers to the presence or absence of the anthocyanin coloration of the petiole and can be evaluated by visual observation. "Petiole: anthocyanin coloration" can be evaluated on the basis of Note 1 (absent) or Note 9 (present).

(Characteristic No. 14) "Petiole: length" refers to the length (cm) of the petiole and can be evaluated by visual observation. "Petiole: length" can be evaluated on the basis of Note 3 (short), Note 5 (medium), or Note 7 (long).

(Characteristic No. 15) "Head: length of branching" refers to the length of branching of the head at the base, excluding the stem. "Head: length of branching" can be evaluated on the basis of Note 3 (short), Note 5 (medium), or Note 7 (long).

(Characteristic No. 16) "Head: size" refers to the size of the head (height of head multiplied by diameter of head). "Head: size" can be evaluated on the basis of Note 3 (small, e.g., Var.: GREEN COMET), Note 5 (medium), or Note 7 (long, e.g., Var.: OKA MIDORI).

(Characteristic No. 17) "Head: weight" refers to the weight (g) of the head. "Head: weight" can be evaluated on the basis of Note 3 (light, e.g., Var.: GREEN COMET), Note 5 (medium, e.g., Var.: WASE MIDORI), or Note 7 (heavy, e.g., Var.: OKA MIDORI).

(Characteristic No. 18) "Head: shape in longitudinal section" refers to the shape in the longitudinal section of the head and can be evaluated by visual observation. "Head: shape in longitudinal section" can be evaluated on the basis of Note 1 (circular), Note 2 (transverse broad elliptic), Note 3 (transverse medium elliptic), Note 4 (transverse narrow elliptic), or Note 5 (triangular).

(Characteristic No. 19) "Head: color" refers to the color of the head and can be evaluated by visual observation. "Head: color" can be evaluated on the basis of Note 1 (cream), Note 2 (green, e.g., Var.: NAKATE MIDORI), Note 3 (gray-green), Note 4 (blue-green), or Note 5 (violet).

(Characteristic No. 20) "Head: intensity of color" refers to the intensity of the color of the head and can be evaluated by visual observation. "Head: intensity of color" can be evaluated on the basis of Note 3 (light, e.g., Var.: GOKUWASE MIDORI), Note 5 (medium, e.g., Var.: WASE MIDORI), or Note 7 (dark, e.g., Var.: OKA MIDORI).

(Characteristic No. 21) "Head: anthocyanin coloration" refers to the presence or absence of the anthocyanin coloration of the head and can be evaluated by visual observation. "Head: anthocyanin coloration" can be evaluated on the basis of Note 1 (absent) or Note 9 (present).

(Characteristic No. 22) "Head: intensity of anthocyanin coloration" refers to the intensity of the anthocyanin coloration of the head and can be evaluated by visual observation. "Head: intensity of anthocyanin coloration" can be evaluated on the basis of Note 3 (weak), Note 5 (medium), or Note 7 (strong).

(Characteristic No. 23) "Head: knobbling" refers to the degree of the knobbling of the surface of the head and can be evaluated by visual observation. "Head: knobbling" can be evaluated on the basis of Note 3 (fine, e.g., Var.: GREEN COMET), Note 5 (medium, e.g., Var.: OKA MIDORI), or Note 7 (coarse, e.g., Var.: NAKATE MIDORI).

(Characteristic No. 24) "Head: texture" refers to the degree of texture of the surface of the head and can be evaluated by visual observation. "Head: texture" can be evaluated on the basis of Note 3 (fine, e.g., Var.: NAKATE MIDORI), Note 5 (medium, e.g., Var.: OKA MIDORI), or Note 7 (coarse, e.g., Var.: NAKAZATO WASE).

(Characteristic No. 25) "Head: firmness" refers to the degree of firmness of the head and can be evaluated by visual observation. "Head: firmness" can be evaluated on the basis of Note 3 (loose), Note 5 (medium), or Note 7 (firm).

(Characteristic No. 26) "Head: conspicuousness of spiral pattern" refers to the conspicuousness of the spiral pattern of the surface of the head and can be evaluated by visual observation. "Head: conspicuousness of spiral pattern" can be evaluated on the basis of Note 1 (obscure) or Note 2 (obvious).

(Characteristic No. 27) "Head: bracts" refers to the presence or absence of the bracts of the head and can be evaluated by visual observation. "Head: bracts" can be evaluated on the basis of Note 1 (absent) or Note 9 (present).

(Characteristic No. 28) "Peduncle: length" refers to the length of the peduncle of the head. "Peduncle: length" can be evaluated on the basis of Note 3 (short, e.g., Var.: GREEN COMET), Note 5 (medium, e.g., Var.: JORYOKU), or Note 7 (long, e.g., Var.: NAKAZATO WASE).

(Characteristic No. 29) "Peduncle: thickness" refers to the thickness of the peduncle of the head. "Peduncle: thickness" can be evaluated on the basis of Note 3 (fine, e.g., Var.: GREEN COMET), Note 5 (medium, e.g., Var.: WASE MIDORI), or Note 7 (thick, e.g., Var.: OKA MIDORI).

(Characteristic No. 30)

"Peduncle: hardness" refers to the hardness of the peduncle of the head and can be evaluated by visual observation. "Peduncle: hardness" can be evaluated on the basis of Note 3 (soft), Note 5 (medium, e.g., Var.: GREEN COMET), or Note 7 (hard).

(Characteristic No. 31)

"Peduncle: color" refers to the color of the peduncle of the head and can be evaluated by visual observation. "Peduncle: color" can be evaluated on the basis of Note 1 (white), Note 2 (light green, e.g., Var.: GREEN COMET), Note 3 (green), or Note 4 (tinged with purple).

(Characteristic No. 32)

"Plant: secondary heads" refers to the presence or absence of the secondary heads at the time of harvest and can be evaluated by visual observation. "Plant: secondary heads" can be evaluated on the basis of Note 1 (absent) or Note 9 (present, e.g., Var.: NAKATE MIDORI).

(Characteristic No. 34)

"Flower: color" refers to the color of the flower at the time of flowering and can be evaluated by visual observation. "Flower: color" can be evaluated on the basis of Note 1 (white) or Note 2 (yellow).

(Characteristic No. 35)

"Flower: intensity of yellow color" refers to the intensity of the yellow color of the flower and can be evaluated by visual observation. "Flower: intensity of yellow color" can be evaluated on the basis of Note 3 (light), Note 5 (medium), or Note 7 (dark).

(Characteristic No. 36)

"Time of harvest" refers to the time of harvest (the time at which half of the individuals are in the optimal time of harvest). "Time of harvest" can be evaluated on the basis of Note 3 (early, e.g., Var.: WASE MIDORI), Note 5 (medium, e.g., Var.: OKA MIDORI), or Note 7 (late, e.g., Var.: NAKATE MIDORI).

(Characteristic No. 37)

"Time of beginning of flowering" refers to the time of beginning of flowering (the time at which 50% of the individuals are with at least 10% of small flowers). "Time of beginning of flowering" can be evaluated on the basis of Note 3 (early, e.g., Var.: GREEN COMET), Note 5 (medium, e.g., Var.: NAKATE MIDORI), or Note 7 (late).

(Characteristic No. 38)

"Male sterility" refers to the presence or absence of male sterility and can be evaluated by visual observation. "Male sterility" can be evaluated on the basis of Note 1 (absent) or Note 9 (present).

(Characteristic No. 40)

"Leaf: number" refers to the total number of leaves. "Leaf: number" can be evaluated on the basis of Note 3 (few, about 16, e.g., Var.: OHAYO), Note 5 (medium, about 22, e.g., Var.: GRANDOME), or Note 7 (many, about 26, e.g., Var.: OKUMIDORI 100).

(Characteristic No. 41)

"Stem: length" refers to the length of the stem from the ground edge to the base of the small flower head at the lowermost part of the main head. "Stem: length" can be evaluated on the basis of the Note 1 (short, about 16 cm, e.g., Var.: OHAYO) or Note 9 (long, about 26 cm, e.g., Var.: PIXEL).

(Characteristic No. 42)

"Leaf: depth of lobes" refers to the distance from the center point of the line connecting the apexes of the leaf blades above and below the lobe of the leaf to the position closest to the main vein of the lobe, and also refers to the deepest lobe when there are two or more lobes. "Leaf: depth of lobes" can be evaluated on the basis of Note 1 (shallow, about 2 cm, e.g., Var.: OHAYO) or Note 9 (deep, about 7 cm, e.g., Var.: CHALLENGER).

The deposited line has self-incompatibility. The S genes for self-incompatibility of the deposited lines are an $SRK^{18}$ gene and an $SLG^{18}$ gene. Regarding the $SRK^{18}$ gene and the $SLG^{18}$ gene, reference can be made to Reference 1 below. The base sequences of the $SRK^{18}$ gene (Genbank Accession No.: AB032473.1) and the base sequences of the $SLG^{18}$ gene (Genbank Accession No.: AB032471.1) are, for example, the base sequences of SEQ ID NO: 1 and SEQ ID NO: 2, respectively.

Reference 1: Tohru Suzuki et al., *Characterization of Brassica S-haplotypes lacking S-locus glycoprotein*, FEBS Letters, 2000, vol. 482, pp. 102-08.

$SRK^{18}$ gene (SEQ ID NO: 1)

5'-

ATGAAAGGTGTACGAAACATCTATCACCATTCTTACACCTCCTTGTTGCTCGTCTACGT

TGTCATGATTCTATTTCATCCTGGCCTTGCGATCTATATCACCACTTTGTCGGCTACAGA

ATCTCTTACAATCTCAAGCAACAGAACACTTGTATCTCCCGGCAATGTCTTCGAGCTC

GGTTTCTTCAAAACCACCTCAAGTTCCCGTTGGTATCTCGGGATATGGTACAAGAAAT

TGCCCGACAGAACCTATGTATGGATTGCCAACAGAGATAACCCTCTCCCCAATACCAT

TGGAACCCTCAAAATCTCAGGCAATAATCTTGTCATCCTTGGTCATTCCAATAAATCTG

TTTGGTCGACGAATGTAACTAGAGGAAATGAGAGATCTCCGGTGGTGGCAGAGCTTC

TCGCTAACGGAAACTTCGTGATGCGAGACTCCAATAACACAGACGCAAATGAATTCT

TGTGGCAAAGTTTCGATTTCCCTACAAATACTTTGCTTCCAGAGATGAAACTGGGTTA

CGACCTCAAAACAGGGCTGAACAGGTTCCTTACATCATGGAGAGGTTCAGATGATCC

GTCAAGCGGGGATCACTTGTACAAGCTCGAACCCCGAAGTTTTCCTGAATTTTATATA

TTTAACGACGACTTTCCAGTGCATCGGATTGGTCCATGGAATGGAATCGAATTTAGTG

GCATACCAGAGGACCAGAAGTCGAGTTACATGGTGTACAATTTCACAGAGAATAGTG

-continued

```
AGGAGGTTGCTTATTCATTTCGAATGACCAACAACAGCATTTACTCGAGATTGATAATA

AGTTCCGAAGGGTATTTACAGCGACTGATATGGACTCCGTCAACAAAGATATGGCAAG

AGTTCTGGTCTTCTCCAGTGAGCCTCCAGTGCGATCCATACAGGATTTGTGGGCCTTA

CGCTTACTGTGACGAGAACACATCACCGGTGTGTAACTGTATACAAGGGTTCGATCCC

AAGAACCAGCAGCAGTGGGATCTGAGATCCCATGCAAGTGGGTGTATAAGGAGGAC

GTGGCTGAGCTGCCGTGGTGATGGTTTTACAAGGATGAAGAATATGAAGTTGCCAGA

CACTACGGCGGCGATTGTCGACCGGAGTGTTGGTGTGAAAGAATGTGAGAAGAAATG

CCTTAGCAATTGTAATTGTACTGCATTTGCAAATGCGGATATCCGGAATGGTGGACG

GGTTGTGTGATTTGGACCGGGGAGCTTGAAGATATCCGGAATTACGTTGCTGACGGTC

AAGATCTTTATGTCAGATTAGCTGCTGCTGATCTCGTTAAGAAGAGAAACTCGAATGG

GAAAATCATAGGTTTGATTGTTGGAGTTAGTGTTCTGCTTCTTCTAATAATTTCCTGCC

TCTGGAAAAGGAGACAAAAGCGAGCAAAAGCAAGTGCAACATCTATTGCAAATCGA

CAGAGAAACCAAATATGCCTATGAACGGGATGGTGCTATCAAGCAAGAGACAGTTG

TCTGGAGAGAACAAAATTGAGGATTTGGAACTTCCATTGATAGAGTTGGAAGCTGTT

GTCAAAGCCACCGAAAATTTCTCCAGTTGTAATAAAATCGGAGAAGGTGGTTTTGGT

ATTGTTTACAAGGGAAGATTACTTGATGGGCAAGAAATCGCGGTAAAAAGGCTATCA

AAGACGTCATTTCAAGGGACTGATGAGTTTATGAATGAGGTGACATTAATCGCAAGGC

TTCAGCATATAAACCTTGTTCAAGTTCTTGGCTGTTGCATTGAAGGAGATGAGAAAAT

GCTGATATATGAGTATTTGGAAAATTTAAGCCTCGATTCTTATCTCTTCGGAAAAACCC

GAAGCTCTAAGCTAAGTTGGAAGGAGAGATTCGACATTACCAATGGTGTTGCTCGAG

GGCTTTTATATCTACATCAAGACTCACGATTTAGGATAATCCACAGAGATTTGAAAGTA

AGTAACATTTTGCTTGATAAAAATATGATCCCAAAGATCTCGGATTTTGGGATGGCCA

GAATATTTGCAAGGGATGAGACGGAAGCAAACACAATGAAGGTGGTCGGAACTTAC

GGCTACATGTCCCCAGAGTATGCAATGAATGGGATCTTCTCAGAAAAATCAGATGTTT

TCAGTTTTGGAGTCATAGTTCTTGAAATTGTTACTGGAAAGAGGAACAGAGGATTCTA

CAACTTGAACTACAAAAACAATTTTCTAAGCTATGCATGGAGTAATTGGAAGGAAGG

AAGAGCGCTAGAAATCGTAGATCCAGTCATTGTAGATTCATTGTCACCACTGTCATCA

ACATTTCAACCACAAGAAGTCCTAAAATGCATACAAATTGGTCTCTTGTGTGTTCAAG

AACTTGCAGAGCACAGACCAACGATGTCGACTGTGGTTTGGATGCTTGGAAGTGAAG

CAACAGAGATTCCTCAGCCTAAACCGCCAGGTTATTGCGTCGGAAGCAGTCCTTATG

AACTAGATCCATCAGCAAGTAGGCAGTTGGACGATGATGAATCCTGGACGGTGAACC

AGTACACTTGCTCAGTCATCGATGCCCGGTAATATGAACGCTGTTGAGGAAGTTCATA

TAATTAAACATTACTAAATGCAGTGACTCAATATCATATGTGAAAGAAGGAAATAAATT

CTCAAAATATAAGTATGTTATTTTGTAAC-3'
```

SLG[18] gene (SEQ ID NO: 2)

```
5'-

ATGAAAGGCGTGAGAAAAACCTACGATAATTCTTACACCGTAACCTTTTTGCTTGTCT

TTTTCGTCTTGATCCTATTTCGTCCTGCCTTTTCGATCAACACGTTGTCGGCTACAGAA

TCTCTTACAATCTCAAGCAACAGAACACTTGTATCTCCCGGCAACGTCTTCGAGCTCG

GCTTCTTCCGAACCACCTCAAGTTCTCGTTGGTATCTCGGGATATGGTACAAGAAATT
```

```
-continued
GCCCGACAGAACCTATGTATGGGTTGCCAACAGAGATAACCCTCTCTCCAGTTCCACT

GGAACCCTCAAAATTTCAGGCAATAATCTTGTCATCCTTGGCCACTCCAATAAATCTG

TTTGGTCGACGAATGTAACTAGAGGAAATGAGAGATCTCCGGTGGTTGCAGAGCTTC

TCGCTAATGGAAACTATGTGATACGAGACTCCAATAACAAGGACGCAAGTGGATTCTT

GTGGCAAAGTTTCGATTTCCCTACAAATACTTTGCTTCCAGAGATGAAACTGGGTTAC

GACCTCAAAACAGGGCTGAACAGGTTCCTTACATCATGGAGAGGTTCAGATGATCCG

TCAAGCGGGGAAATCACTTACAAGCTCGAACCCCGAAGGTTTCCTGAGTTTTATATAT

TTAGCGACGACTTTTGAGTGCACCGGATTGGTCCATGGAATGGAATCGGATTTAGTGG

CATACCAGAGGACCAGAAGTCGAGTTACATGGTGTACAATTTCACAGAGAATAGTGA

GGAGGTTGCTTATTCATTTCAAATGACCAACAACAGCATTTACTCGAGATTGATAATAA

CTTCCGAAGGGTATTTACAGCTACTGATGTGGACTCCGTCAACAAAGATGTGGCAAG

AGTTCTGGTCTTCTCCAGTGAGCCTCCAGTGCGATCCATACAGGATTTGTGGGCCTTG

CGCTTACTGTGACGAGAACACATCACCGGTATGTAACTGTATACAAGGGTTCTATCCC

AAGAACCGGCAGCAGTGGGATGTGAGAGTCGCTTCAAGTGGGTGTATAAGGAGAAC

ACGGCTGAGCTGCAGTGGAGATGGTTTTACCAGGATGAAGAACATGAATTTGCCAGA

CACTACAATGGCGACTGTAGACAGGAGCATTGATGTAAAAGAATGTAAGAAGAGATG

CCTTAGCGATTGTAATTGTACCGCTTATGCAAATGCGGATATCCGGAATGGTGGGACG

GGTTGTGTGATCTGGACCGGAGCGCTTGAGGACATCCGGACTTACTTTGCTGAAGGT

CAAGATCTTTATGTCAAATCGGCTGCTGCTGACCTTGCTTAG-3'.
```

In the present invention, plants having "essentially all physiological and morphological characteristics of the deposited line" are meant to be plants having the main characteristics of the deposited line when grown in the same environment. The main characteristics are the following characteristics of (1) to (10), i.e., characteristics of Characteristic Nos. 6, 9, 13, 21, 25, 28, 36, and 40 to 42, and self-incompatibility. The main characteristics are preferably characteristics of Characteristic Nos. 9, 13, 21, and 36 in Tables 1A and 1B, i.e., the following characteristics of (1) to (3) and (9) and self-incompatibility. The plants having essentially all physiological and morphological characteristics of the deposited line may be, for example, plants having the same characteristic as the deposited line, except for 10 or less, 9 or less, 8 or less, 7 or less, 6 or less, 5 or less, 4 or less, 3 or less, 2 or less, or 1 characteristic, i.e., 10 or less, 9 or less, 8 or less, 7 or less, 6 or less, 5 or less, 4 or less, 3 or less, 2 or less, or 1 characteristic may differ from the deposited line. The "characteristic different from the deposited line" may be a main characteristic of the deposited line or a characteristic other than the main characteristic of the deposited line, and is preferably a characteristic other than the main characteristic of the deposited line. The "characteristic different from the deposited line" can be made, for example, by the introduction of a characteristic and/or introduction of a gene, which will be described below. In the plants having essentially all the physiological and morphological characteristics of the deposited line, all the characteristics of Characteristic Nos. 1 to 21, 23 to 32, 34 to 38, and 40 to 43 and self-incompatibility may be the same as the deposited line.

(1) anthocyanin coloration of leaf blade: absent;

(2) anthocyanin coloration of petiole: absent;

(3) intensity of anthocyanin coloration of head: weak;

(4) number of leaves: many;

(5) length of stem: short;

(6) firmness of head: firm;

(7) number of lobes: many;

(8) depth of lobe: deep;

(9) time of harvest: late; and

(10) self-incompatibility gene: SRK[18] gene and SLG[18] gene.

The deposited lines have, for example, the single nucleotide polymorphisms (SNPs) described in Tables 2A through 2U below. In Tables 2A through 2U, the base [$N_1$/$N_2$] in parentheses denotes a single base polymorphism in which $N_1$ is a base in a dataset (*Brassica oleracea* L.: genome base sequence of TO1000) registered in NCBI with RefSeq assembly accession: GCF_000695525.1 (https://www.ncbi.nlm.nih.gov/assembly/GCF_000695525.1/) and $N_2$ is a base other than the base in the dataset. For the analysis of the data set, reference can be made to Reference 2 below, for example.

Reference 2: Isobel A. P. Parkin et al., *Transcriptome and methylome profiling reveals relics of genome dominance in the mesopolyploid Brassica oleracea*, Genome Biology, 2014, vol. 15, no. 6, art. no. R77.

TABLE 2A

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP1 | 1 | 0.990 | 454335 | SEQ ID NO: 3 | TGACTTGTGTCGGTGGCTAGAGGAAAAGGCCCCTTTGTCCACAAAC GTGT[T/G]GTCTGTCTGGGCCATTCATTTCAAGCCCATGTATTAC GGTTTTAATTACG | G | T | A |
| SNP2 | 1 | 6.422 | 1264234 | SEQ ID NO: 4 | TTTGAAACAACAAGCAGATAACCCAAAGCAACTTCTTGCTGAGCTA GATGG[G/C]CATGGCATCAGCTAATAAGGCAAGTGCTAGTGACAAG GCTGTTGCTACTG | G | C | B |
| SNP3 | 1 | 9.780 | 1783522 | SEQ ID NO: 5 | ATTCTCTGTTCTTGATCATGCGCTTGTGTCTTCTATTCCCTGAACC CTTCA[T/C]TGGACTCTTGACCTCTTTTCTTACCAAAACAAGTAAA ATCCTCAAGAGAA | C | T | B |
| SNP4 | 1 | 24.743 | 4314082 | SEQ ID NO: 6 | ACGATGTGCTGGAGGATGGAAGTGAAGTGGAAAATTTGTTGAAAAA TGCC[T/G]CAGAGAAGACAGCAGAGGCGCTGCAGGCGAAAGACGA GTATGAGAAACAT | T | G | A |
| SNP5 | 1 | 36.521 | 7889954 | SEQ ID NO: 7 | TCTTGCAGCCTAATCTTTCGGCTATCCCATGGCACTCGGTGATTTG AGCTC[A/C]AAGAGAGGATACAAAAGCACGCTTTTATTTCATGGGT CCTTGTGAGACAC | A | C | A |
| SNP6 | 1 | 39.178 | 8784702 | SEQ ID NO: 8 | TGAGATTTGGAGCTGCAGTGATCACAGACTCTAGCGACCGTCGGAC TAGCG[C/T]TTAGTAGAGTGACCTATTTCTTTGCATAACTCACATA CCGGTGGCATCCA | C | T | B |
| SNP7 | 1 | 40.958 | 9420949 | SEQ ID NO: 9 | AAGTTTGGATCGGACGCAATCGCTGCACTGGCGGCACTAACGCTCT CCGGC[C/T]ATCGAAGAAGTTGCAGCCATCTGCAGCGGCTGAGCGG GTAACTGTAAACC | C | T | A |
| SNP8 | 1 | 46.689 | 11980318 | SEQ ID NO: 10 | AACCGGAACATTCCGTAGTCTGCAGCGTACCAGAACTTAGCTCGGT ATCTC[G/A]GCAGGAAAGTAGAACATGGTCTCTGCGGGAACACCAC ACTCTCCCCCAGA | G | A | A |
| SNP9 | 1 | 52.193 | 13607081 | SEQ ID NO: 11 | TCAGCCTGGCGTCTCTCTCCAGCTCCAAGCTGAGCCCAGTTCAGCC GTGAA[G/C]GTCTGCTCACACCCCGGCATTTGAGCACCATTGTAGG TCTGCAAAATCCT | G | C | B |
| SNP10 | 1 | 52.272 | 13635739 | SEQ ID NO: 12 | TGAGACCAAGGTCATAGAGCGAGCCGAACTCTGAGTGGACAGAAGA CAACC[C/G]ACATCAACATCAGCCAAGCGTAACTAATAGTTACAAG GTGGATCTCTGCA | C | G | B |

TABLE 2B

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP11 | 1 | 56.649 | 17705704 | SEQ ID NO: 13 | CGTTTGGGAAATGCGCGATGACGTGATCTCGTTTGCGTTTCTTCTG ACTTC[A/G]TATCTCACTCGCATCTCGAGCTCGGGCCTTCGTCTCT GCAGCTGCGGGAC | A | G | B |
| SNP12 | 1 | 58.660 | 22288471 | SEQ ID NO: 14 | TCGTTAAATGCTGCAGTTTCCATGCCAAGCTTCTGATCTTCAAATG GGTGT[G/T]TCGTCAACTTTTTCTAATCGCTGAGGAAGAGGCGTTG GCATAGGATTGCA | G | T | A |
| SNP13 | 1 | 75.912 | 41231290 | SEQ ID NO: 15 | TCTCCGGCAACAGCCGATGGACCTGTTTGCCCACCGACGACAAAAC TTAAG[T/C]CGGGCAAGTTTCCCTGAAGGTTTCCTATTTGGCACGG CTACTGCAGCATA | T | C | B |
| SNP14 | 1 | 77.423 | 41526625 | SEQ ID NO: 16 | TGTCTGAGAGGCAAAATGCCAAGATCAGAGTGGTGAAAATGAACT CATTC[A/C]TAGCACATAACAAATGAAGTAGTCTTCTATGACCATC ACACTATACTACA | A | C | A |
| SNP15 | 1 | 82.329 | 42118296 | SEQ ID NO: 17 | CTGCAGATACAGACGGAGGATTGCGTTAGATCGGGATCGGGAGGGA GCAA[G/T]GAGATCGATCGGTTGCCGTGGAAAGGAGGGAGCGAGG GGAATCCTGATTA | G | T | A |
| SNP16 | 1 | 87.796 | 42587881 | SEQ ID NO: 18 | TATGTGGGAGTCATTGCTTGAACCGCTTCTGAGTCCTTTGTTGACA CCACT[G/C]TCAGCGAGCTCTTGACTCCTCGTGGACTAGTCTTCTA CGGGAAGGCAGGG | G | C | B |

TABLE 2B-continued

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP17 | 1 | 88.361 | 42631525 | SEQ ID NO: 19 | AGTACGACCGCACCTGGTTTGAAAATTTCCATCACTTTCCCCATGA TGGG[T/C]TTGAACAAGAGATGATAGCTCTCGTCGTCGATACCAT CGTCCAGTGGTAC | C | T | A |
| SNP18 | 1 | 88.361 | 42631552 | SEQ ID NO: 20 | TCCATCACTTTCCCCATGATGGGTTTGAACAAGAGATGATAGCTCT CGTC[G/A]TCGATACCATCGTCCAGTGGTACGTTGAGAGAATAGT ACTTTCCACTTCC | A | G | A |
| SNP19 | 1 | 95.612 | 43132615 | SEQ ID NO: 21 | AGTCCTCTGCAGCATAATCAGAGTAAGCAAAGAAGAGCAGGCTTGG AGTG[A/T]CGAAAGAGATGCTCTTTGGGTTCTGAATGGTTTTCAT GCCCGTGGTGTGA | T | A | B |
| SNP20 | 2 | 3.410 | 717479 | SEQ ID NO: 22 | ATAACTTCCACAATCGCTGGTGTTGCCGTCTCTAACGCTAACCTAT TCGG[T/A]ATTGCAAACGGAACAGCACGAGGCGGTGTTCCCTCTG CTCGAATAGCCAC | T | A | A |

TABLE 2C

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP21 | 2 | 3.410 | 717482 | SEQ ID NO: 23 | ACTTCCACAATCGCTGGTGTTGCCGTCTCTAACGCTAACCTATTC GGTAT[T/A]GCAAACGGAACAGCACGAGGCGGTGTTCCCTCTGC TCGAATAGCCACTTA | T | A | A |
| SNP22 | 2 | 8.829 | 1481256 | SEQ ID NO: 24 | GAAGCGAGTGCGATGAGTGCAAGACCTCCTACGATTGCTGCCGTG TTCTC[A/T]GCCCCATCGGACGAAGATCCTGCAGTGCCTGAGCT TATGGCGCTCTCTGC | A | T | B |
| SNP23 | 2 | 32.758 | 3792354 | SEQ ID NO: 25 | AGTGAAGAACCCTGCAGAGAAGACTCGAGTAGTTTCTCCGTGTTT GCTTG[G/A]TTTGAGGCGTTTGAGAGAAGAAGAAGTGGCGGAAG CAGCTATAGAACAGT | G | A | B |
| SNP24 | 2 | 49.203 | 8267341 | SEQ ID NO: 26 | GCTGAAAAACGAACTAGCCGCGATCATTGTGAAGAGGGCATCACT AAATC[G/A]CAATGCAGTAAATAAAGAGGTTGAAGAAGATAACA TCAAAGACATTAGTG | A | G | A |
| SNP25 | 2 | 49.415 | 8420520 | SEQ ID NO: 27 | TTGCTGCAGCTTTGTGAGGAGAGTGTGGTGTATCGAACCATGGTG GCGCG[A/C]GAAGGTGCGATTGCTCCTGTGGTGGCTTTGTCGCA GAGTAGTAAGAGTCG | A | C | B |
| SNP26 | 2 | 49.704 | 8638214 | SEQ ID NO: 28 | GGAAGCACGAGTTTTGCGGCTGTGGAGGACAGCATAGACACGGTG TTGGG[T/C]GATGCCTAGCTGGGATCGCCTCTTGTAGAGCGTAG GAGAGGCAATGAGTT | T | C | A |
| SNP27 | 2 | 51.821 | 11081737 | SEQ ID NO: 29 | ATGACCTACGACAAGTAGACAAGATGTGTGTGTCCGAAACAGGCG GCTCA[A/G]GCAAGTTAGTTTTCAGGAATGCATCAACCACAACA GGTGAGGCATATGTT | G | A | A |
| SNP28 | 2 | 55.999 | 27333228 | SEQ ID NO: 30 | CACCATAAAAGCTGCAGCAGCCTCTTCAACAACAATTTTTCTTCT TCCTT[G/A]CACGATCCTCTCCTAGAGGGTTCTCCTACTTCTCC TCTTCTTTTCAAAGA | G | A | A |
| SNP29 | 2 | 62.589 | 45424768 | SEQ ID NO: 31 | CTCATTGCTCGTACACTGCAAATGTTCATGTCTCTGCTCCTGCTG TGTCC[G/A]GCAGATTTGTACTTCTATACGGTCCTCAGATAGTT GGCTTCTCATTTGCC | A | G | A |
| SNP30 | 2 | 64.493 | 46653493 | SEQ ID NO: 32 | GAGCAAGAGACTGTGATGAGGTTCCTGTGCTGTGAAATGTTGTAG AAAGA[A/T]TCTGATGGTCCACAAACTGAGGAGAAGAGTAGTTC TGTATCTGAGGCTGC | A | T | B |

TABLE 2D

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP31 | 2 | 74.571 | 49757428 | SEQ ID NO: 33 | TCACGGTGGCTGAAAAAACTTCGGGATCAGCATAAAAGATCCACC GGAGG[G/A]GAGGTGTTCGGAGGAGGGAAACATGCGACGGGATG GTGGCTTCCGGGGAA | A | G | A |
| SNP32 | 2 | 77.901 | 50407246 | SEQ ID NO: 34 | AGGTCAGAATCAGTGACACCTGGATAAAACGACCTGGAGACTGAC TGAGA[G/A]AAGTCCAGCTCGACGATTTGAGTGAACCTGAGGGC GAGACGGCCAAGCAA | G | A | B |
| SNP33 | 2 | 83.240 | 51346970 | SEQ ID NO: 35 | GTTCCTATCCTTTGCAAGAGCGTGATCCCGGTGTCTATACCGGTG ATTCT[C/T]CTCAAGGTAGGCACGAGGACGCGGTCGTAGATTAT GATGAAAACAGTCAT | C | T | A |
| SNP34 | 2 | 83.240 | 51347002 | SEQ ID NO: 36 | GTCTATACCGGTGATTCTCCTCAAGGTAGGCACGAGGACGCGGTC GTAGA[T/G]TATGATGAAAACAGTCATTCCCGTCATCAAGAAGA CCACATAGGTGGCTG | T | G | B |
| SNP35 | 2 | 84.263 | 51516676 | SEQ ID NO: 37 | AGTCCAACGCGGTCGTAGTCAACGGGATCGTTGACCGCTCGTTGG TGAGA[G/A]ACAGCCGTTGACGCGATTACGTTGCGGTGAGTGAG GAGAACGCCTTTGAC | A | G | B |
| SNP36 | 2 | 84.263 | 51516714 | SEQ ID NO: 38 | TCGTTGGTGAGAGACAGCCGTTGACGCGATTACGTTGCGGTGAGT GAGGA[G/T]AACGCCTTTGACTTTCCCCGTGGTCCCGGACGAGA AGAGAATCGCTGCAG | T | G | B |
| SNP37 | 2 | 86.232 | 51834225 | SEQ ID NO: 39 | CTTGGTATTGTGCAGTTTATCCCAACACGTTTGACTCTGGATTCA GCGGT[A/G]ACAAGGCCACCACCGCTATTGTGTGAAGCTGACTT ACTGAGTTGCATGGA | A | G | A |
| SNP38 | 2 | 86.232 | 51834270 | SEQ ID NO: 40 | GCGGTAACAAGGCCACCACCGCTATTGTGTGAAGCTGACTTACTG AGTTG[C/T]ATGGACAAGGTGAGTAAAACTGTCTTGTTTGCCCC TCTTTTCATGGTGGT | C | T | A |
| SNP39 | 3 | 1.187 | 675632 | SEQ ID NO: 41 | GCCTCCTCGTTCCAGCGTTGTAACGAGACACAAAACGCTTTAGTG AGACT[A/C]CACAACAGCTTGTTGCAACAAGCCGTGATAAAGCT CAATAACGAAGCCAA | A | C | B |
| SNP40 | 3 | 2.498 | 948354 | SEQ ID NO: 42 | GTCGTCTCTGCCCTCCCCGGCGGGTTCAACGAGATCGATCCCGTC GCCGT[C/T]GTCGTGGTCCTCGCGATCACCGTCATCATCTGCTG CAGCACGAGGGAGAG | T | C | B |

TABLE 2E

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP41 | 3 | 5.739 | 1516935 | SEQ ID NO: 43 | GTGGTTGAAGGACAGCCAACGCAGCCAGAGCAAGGTAACCAAGC CACGTC[A/G]CTACTCGTGTCCATGGCCAGGAGTAGAGTCTGA GCCGGAGTTCCGATCTT | G | A | B |
| SNP42 | 3 | 5.739 | 1516977 | SEQ ID NO: 44 | GCCACGTCACTACTCGTGTCCATGGCCAGGAGTAGAGTCTGAGC CGGAGT[T/A]CCGATCTTAGCCTTGACAATGTACGTTGCGCTC TGCAGCATTTGACGCCC | A | T | B |
| SNP43 | 3 | 20.656 | 3369359 | SEQ ID NO: 45 | CGGGTGTGGGAGCCGGAGGAGAGGCAGCAGAGTCGGTGGGTGCC TCGCCA[G/A]AATCACTGGGACTAGCCGCGGAGTAGTCATCCT CAGCAGCGGGTCCTTCT | A | G | A |
| SNP44 | 3 | 21.013 | 3409356 | SEQ ID NO: 46 | TCTGTTTAGAGGCAGTGGACTTGAGTTTCCGGTCTGGCTTCACC GTCTCA[G/T]CGCGTTTAGGTTTAGCGTTCTTGTCCACAGGAG AAGCTTCTCTGCCTCA | T | G | B |
| SNP45 | 3 | 28.303 | 4315752 | SEQ ID NO: 47 | TTGAACTTGCCGTGTTTGAACTTACCGTGACCATGATACCCGTA GCCATA[T/G]CCGTGACCATGGTGGTGACCATAGTGTCCGTGG TGAGACATATGGTGAGA | T | G | A |
| SNP46 | 3 | 38.853 | 5932635 | SEQ ID NO: 48 | GTGACCAAGCTAACAAAGCGAGTCCAGGAATGTTCCAATTCTGT GGTCCAC[G/A]CAAAGCTGAATAAAGGGCATGAGCTTATTCAC CAAACGCCAAAACAAAT | G | A | A |

TABLE 2E-continued

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP47 | 3 | 48.248 | 8135062 | SEQ ID NO: 49 | GCTGGTCGGAACTCATGGAGAGTGAGTAAATTTTCTTCTTTACA CGAGAA[T/G]GAATCCATCCATGGCTCAAATCTTGATCGGTTT CAGGGTACGTTGAAGAA | T | G | B |
| SNP48 | 3 | 49.393 | 8510724 | SEQ ID NO: 50 | AGTCACCGGAGAGGACCCGGGTTCAACGGGAGCCACTCTAGTAA TAGTAG[T/C]AATACCTGGGGGAGGTTCGGCGGGAACAGCAGG GCGGTTGTGACGAAGAC | C | T | A |
| SNP49 | 3 | 54.259 | 10912440 | SEQ ID NO: 51 | AGTTGGATCCTCAACGTTTGCCTTCTTTGGGTTCAACGGTAATG ACATTC[T/G]CAATCTCATTACTTTTCTGAATAAAGCTTTTTT CTTATTGTGTGAAACTA | T | G | B |
| SNP50 | 3 | 56.441 | 12711867 | SEQ ID NO: 52 | CTGCAGATTATTGTTCAATACACTATACTATTGGGAGGTGGCTG TAAGGT[A/C]TTATGGGCATTGAAGGTGGGAACACAAGTTCAA AATCTGGAAATGTGGAC | C | A | B |

TABLE 2F

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP51 | 3 | 59.622 | 14684781 | SEQ ID NO: 53 | TCTCCTGCATCGAAGGTCCAGTGAACCGCATAGTGTGTACGTT CATTTGT[T/A]TGAAACGCCAGAGAGGAAATGTAACCATTGT GTATCTCCCCGCATATCCC | A | T | B |
| SNP52 | 3 | 68.614 | 20818643 | SEQ ID NO: 54 | GCGGCACAAACGGAGCAGGATCTTACTTCTGAGAAGAGAGTAT GCGTTCG[C/T]GATCGATTCACCTTTTGCTAGGGATCGATTT CCTGGCTTAGTATACTTTG | T | C | B |
| SNP53 | 3 | 71.069 | 22019198 | SEQ ID NO: 55 | AGCCAATGAGCTTGTGGACTTCATGGAAGCCTCTGGGGATCTT CTGGATG[A/G]CAAAGCAATGGCGTCTTTAGTCGAAGGGCAT TGCGATGCCAAAGATCTCG | A | G | B |
| SNP54 | 3 | 75.613 | 23508195 | SEQ ID NO: 56 | TGTTGGAGAGTGCAGTTTATGACTCTAATGCCGCTGACATCCT GTTCGTT[T/G]CCGTACCTTCCAAGGCTTCCGACACTGATTC CATGTCCTGGACCGCAGGT | T | G | A |
| SNP55 | 3 | 76.384 | 23746683 | SEQ ID NO: 57 | AGAGTCTTCCTTGGGGTTGGAGTTGGTGACGACAGGTCCGCTA CAGTACT[C/T]CCTGCCGGACTCACCGGATCCGTCGCCCAAC CCTTCTCCATATCTGGTTC | C | T | B |
| SNP56 | 3 | 76.582 | 23809957 | SEQ ID NO: 58 | TTCTTCTCAGTGGCACTACCATTTGCTGCAGAAGCTCTGAGAA GAGGCTC[C/T]AAGAGCTTGCTTGCCACATCAGGAGGCAAAG CGTCTTCACCGGGAAGAAC | T | C | A |
| SNP57 | 3 | 79.755 | 24764254 | SEQ ID NO: 59 | CTAGCATCAACCTCTGTCCCGCCAGTCCCTGTCACAGCTGCTC TATCCCC[T/G]GCCTGCCCTATCTCATCTGCCCTAGCCCCTG CTGCAGGTTCTTCGGGCTG | T | G | A |
| SNP58 | 3 | 80.244 | 24921510 | SEQ ID NO: 60 | ACACATCCACAATCTCCTCAAACGAACAACGCCTCATGCTACG GCCTCTA[T/C]AATCTTGAGCATAGTTCCTCAAGTCCAAAAG CTCTCCGATCTGCAGCTCA | T | C | A |
| SNP59 | 3 | 83.407 | 26569816 | SEQ ID NO: 61 | CTCCGCCGCCACTAGCGCTCCCATTTCCTCCAGCTCCACCTTC CTTATCC[C/A]CCTGTTTCCCCGTGGTCGTCCTCTCCCCTTC CACCTCCCTGTACTTCTGC | A | C | B |
| SNP60 | 3 | 92.321 | 45636043 | SEQ ID NO: 62 | TTTGGCCATGGTGAGGGGAAGCTGCAGGCGAAGAAGAAGGAG ACAGCTG[C/T]GGAGATTCGTCTGCAGGAGGTGCGAGCTCGG ATCAAAGCTTTGACCGAGT | C | T | A |

TABLE 2G

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP61 | 3 | 93.347 | 47819830 | SEQ ID NO: 63 | CGGTTCGATCAGCTTGCACTTCTCGGTAAAGCAATGGATGTAG AAGACCA[G/A]ATCGAATACATTGTTGAAGGCCTATCCGATG ATTACAAGCAGGTAGCTGA | G | A | A |
| SNP62 | 3 | 93.945 | 48535735 | SEQ ID NO: 64 | GCTTCAACACTAAGGTACTATAGAAGAACTTGTTTATGTATGT TGCATCT[C/T]CATACGTGTCTGCGCTTTGGATTCGGTCAAT CATTGTATGTATGTTGCAT | T | C | B |
| SNP63 | 3 | 98.958 | 52628849 | SEQ ID NO: 65 | CTGTTTACCCAAGAACTTGATGCCAACGACCCTGTCTTTGTCG TATGGCT[C/T]AGGAGAAGAGGACATGGCCATGTTGCACACC ACTTCGGTTTGGTAAGTGG | T | C | B |
| SNP64 | 3 | 99.714 | 53167534 | SEQ ID NO: 66 | CATTATGTTCTGCAGCATCTGCAGTGGATCACCATGGCTCACC ACCAGAA[C/T]TGCGCACCTTTGAAATTCTGCTTCCATGGAT AACATGGCAGTGGCAAGTC | T | C | B |
| SNP65 | 3 | 109.082 | 58494494 | SEQ ID NO: 67 | TAAACTGTATTAGCTCACTTTCAGCATCGGTTAGTCCAGACGA GAAGAAT[G/T]ACGACTTCTGAACACTTACTGCCAAGCCTGA TCGAAGCTCAAATCCTTGA | T | G | A |
| SNP66 | 3 | 109.268 | 58569947 | SEQ ID NO: 68 | AGTCATAAGTCTTCTTCACTCTCTTTGTTACACGGTAGCTTAG AACAGCC[A/C]CAAGAAAAGAACAAAGACAAAGAACGGCAC ACAAATTGCTAAGATTATC | C | A | A |
| SNP67 | 3 | 109.415 | 58628362 | SEQ ID NO: 69 | AGAATTGGTCTGCAGCCAAGCAGATTCAAGCGATGGTGGCTAA TCTTGTG[C/T]TCCCACGTGGAGCAGAAGCGATGCCGGTTTA CATAATGAGCAGTGTTATG | C | T | B |
| SNP68 | 3 | 113.736 | 60116952 | SEQ ID NO: 70 | CCTTCTCACTCGCTGCAGCGACTTCTCTTCTTCTTCATCACTA ACAACAA[G/C]ACTAACAAACTCGTCAGCTTCTTCCTCATCA CCTCTCTCGGTTTCTTCAT | C | G | B |
| SNP69 | 3 | 117.120 | 61115979 | SEQ ID NO: 71 | TTTGACATTGGCTCATCAGGAGGTGGAGGTGGTGGGTCTGTTC CATAGGC[A/G]GTGATGAAACGGTCCAGACAGTTGGAGTGGA GGTGGTCTGTGTTGCAGAC | A | G | B |
| SNP70 | 3 | 121.679 | 62286307 | SEQ ID NO: 72 | ACGTCCCTTTGTTGTCATCCCACCAGAATCGAGTGAATGCAGA CTGTATC[C/T]GTTTGCACAATGAAACCGGGAGCTTGAAGCA AGTCATAGAGTGCGATGGA | C | T | B |

TABLE 2H

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP71 | 3 | 125.279 | 63119854 | SEQ ID NO: 73 | AGCTTCCAAAGAACCTTCCCAAACCTAAACCATACCAAGAATC CAAGCAC[A/G]AAACCACCTAAAACACTCGACAGCAATGATC TCCGACGGCACGAGAGAGA | G | A | B |
| SNP72 | 3 | 131.139 | 64347040 | SEQ ID NO: 74 | TTATGCTGTTTTAGCACTAGTGCTTGACCGAGCACGACCTAGA GCAGCGG[C/T]TTCTGAGGGGCTAACCATCCTAGCTGCAGCC GCTGCCTTCAGTCAGGAGC | C | T | B |
| SNP73 | 3 | 131.253 | 64369480 | SEQ ID NO: 75 | CGGTGAGCGTTGGGGTTGATGTCGGGTTGGATACAGAGCTTTG AGCCAGG[A/G]ACGAACTTTCTCGCTTCTACAACGGTCTTGA GACCTGAGTCTACTCTGCA | G | A | A |
| SNP74 | 4 | 11.174 | 1826660 | SEQ ID NO: 76 | AGACCTCGTGCTCCCCTCTGTCGTAGTTCACGTACACGGATTT CTTCTCC[C/T]GGAGTGCGTCGGAGGTCTTCGCTGCAGCTCG AGGACGATAGGCGCGGGAA | C | T | A |
| SNP75 | 4 | 14.947 | 2437167 | SEQ ID NO: 77 | CCATCTGCGAAAGCAATCCCGAGCTCAGGCAGCTCCATGTTGC TCTCCTC[C/T]ACACCAGACACGTTGAAGCAAGGGTCTAGGA TCGGGAAGTCTTCAAACAC | T | C | A |
| SNP76 | 4 | 27.358 | 4981234 | SEQ ID NO: 78 | AGTGCGAAGGATGATGTTCTCAGGTACTGCATTATTTTCTTCT TTATTTA[G/T]TTCAGTGCACTACATGTTACTGCTTTCACTT GCCTCATTTCATTATTTTT | G | T | B |

TABLE 2H-continued

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP77 | 4 | 28.164 | 5155338 | SEQ ID NO: 79 | AAAAAAACTGCAAAGTTCTATATGAAAGTTTGAAAGAAGAACA TATACCA[T/A]TTTGTTGTAGACTCTGAGTCTTTCCTTGACA ACTTCTGCAGTGTCATCAG | A | T | A |
| SNP78 | 4 | 30.983 | 5756433 | SEQ ID NO: 80 | CTGCAGCAGTCCAACTCATTCCCCGCTAGAACTGGAGATCCCC AGGCTAC[C/T]TCAGCTGCAAGCAATCCAGGTGTCTCTGGAG GACAGAAGCCGTTTGTGCC | C | T | A |
| SNP79 | 4 | 34.723 | 6571438 | SEQ ID NO: 81 | TACGAGATCATCCTCTCGAAACTCCCTTGCAAATGGCGCCCCG CTTTGGA[A/C]CATGTCATGAAAATCCTCAACCGTTAGATTC AAGGCACGCTGCTGCAGAA | C | A | B |
| SNP80 | 4 | 36.210 | 6888107 | SEQ ID NO: 82 | GAGAAGGAGGAAGCCTTGGAGAGGGTTGGGAGTTTGAGTGAGG AAGCTGA[T/G]AAGAGCGGGAAGAGAGCGGAGAACGCGAGGG AACAGCTAGGAGCAGCGCA | T | G | A |

TABLE 2I

| SNP ID | Chr | cM | Location of SNP on chromosome | SEQ ID NO: | [SNP] and its adjacent sequences (5'→3') | A | B | Deposit line |
|---|---|---|---|---|---|---|---|---|
| SNP81 | 4 | 39.468 | 7584976 | SEQ ID NO: 83 | CAGCGAGTGCAGCAAATCCTATAACCCGCGTATGCATCGTTGTC AAGAGG[C/T]CATGACGGCGACTAAGAGCATCGGCGACTTTAT TGGTTTTGTCGGACTGA | C | T | A |
| SNP82 | 4 | 42.615 | 8421224 | SEQ ID NO: 84 | CCTCATTTCAAAACTTTCCCATCTCTAGTCTTCAGCTCAGTGAC GATGAG[A/C]TGATCAGTGGCAGGAACGGTAAAGAGATGGATG AGAGTCAGAGTCCAGAG | A | C | B |
| SNP83 | 4 | 42.934 | 8529326 | SEQ ID NO: 85 | CATTACGGAACTTTGAAGAGGTACGAGTTTGAGATGCATAGTAG AGTCTC[A/T]ATGGCTTGGATTCTTGGACTTGGGCCTAGCCTT GGGCTTGTTCGTGTTCC | A | T | A |
| SNP84 | 4 | 44.097 | 8977099 | SEQ ID NO: 86 | CTGAGGAGTTTGGTAGTGTCGCTAAAGCTACTGATAGTGATCTT GATTTC[G/A]TTGTGGTTTCTCCTTCAAAGGCTATTGAGGATG ATAAGGATGCTAAGGTT | G | A | A |
| SNP85 | 4 | 55.699 | 37635182 | SEQ ID NO: 87 | AGAAATCTTGTCACAATTATCAAACATTCGCAACACATTAGCAG GAGATT[T/C]GCCAAGTGAGAAACTCGTTCATGTCGTTGAGAA GCTTCAATGCAAGCCAC | C | T | A |
| SNP86 | 4 | 63.882 | 44453699 | SEQ ID NO: 88 | TGCGGAGGCCTGTAGTTGCGGTTTTCCAAAGCGGCTGCAATGGC TCTTTC[G/A]ACGGATGCTGCTGATACGGATCTGGAGGTTCTA GAGGAAGGCTTTGGGCA | G | A | B |
| SNP87 | 4 | 79.868 | 49190065 | SEQ ID NO: 89 | ACAACGTTGCTCTGCAGATAGTGATCATATATCTCAGACTTATT AGACTC[G/T]AGGATAGCGAGAGCTGCCTTTCTTCTTCAAGAA CTCTGGAATCTCCACCG | G | T | A |
| SNP88 | 4 | 79.868 | 49190123 | SEQ ID NO: 90 | CGAGAGCTGCCTTTCTTCTTCAAGAACTCTGGAATCTCCACCGA ACCACC[A/T]TCTCTAAAGGAGGAAGAAGGTCTTCTTGTAGCT CCAGTTGAGGCAGTATC | A | T | A |
| SNP89 | 4 | 82.873 | 49966272 | SEQ ID NO: 91 | CAAAAGTAGAAGCGAAAGCTATGATGATGATTACAAAAGTCTCC ATCCTT[C/A]TAAACAAAATCGGCACGTATAATTATCCTAGAT ATGTGTATATATAAGTA | A | C | A |
| SNP90 | 4 | 89.350 | 51208004 | SEQ ID NO: 92 | GTTAAGGTGTGGCGGGTCCACGTCATCTCAGGGAACCGAAGCCA TGACTC[C/A]AAGGCAGATCATGGCCGTTGAAGATGGCAGAAG AAACTTGACGCCTGCAG | A | C | A |

TABLE 2J

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP91 | 4 | 89.440 | 51222103 | SEQ ID NO: 93 | GAGGGCGGTAGATCTCTCAGATTCCTCTCTCCATCTCCCTCGTTT TCTTC[T/C]GTCTCTTCTGCTGGTGGTGAAGCAAATAGACACTC TAGGTCTCTTAGTGT | T | C | A |
| SNP92 | 4 | 89.932 | 51294829 | SEQ ID NO: 94 | TTCGATCAGGGATCTGCAGATCAGAAGAGAGACGCATGGAGCACG TGATA[G/C]TAGGAGGCGTTCATGATCTCCCAGGAAACCAGAAC AGTGGAGAGATCGAG | c | G | B |
| SNP93 | 4 | 92.074 | 51600428 | SEQ ID NO: 95 | AGCGATGGGAGCATCTTGTACCTTGATCTTCCCTCCAACATGGTA GGATC[A/T]TTCTTGATGGGTTGGTTCGGCGTCGTGTTCAAAGC AGACATAACCAGAGT | T | A | A |
| SNP94 | 4 | 92.790 | 51699975 | SEQ ID NO: 96 | TCTCCGTCTGGAGTCTCTGTCATGTCTCCGCTCTCGCCGTCCTCC GGGGG[T/C]AACGGGATGTCGTCGATGGCGTGGCCGCAGCCGAA CGTTCCTGCTCTGCA | T | c | A |
| SNP95 | 4 | 92.972 | 51724947 | SEQ ID NO: 97 | AAAGTGCAACCATCATGCATATCGACTTTATGATCATCTTTGAG ATGGTC[A/G]ACAAGGGTTTGAATATCACCGGTCACCGAACAC TCGGAGCCAGCGTAGGG | A | G | A |
| SNP96 | 4 | 97.323 | 52290476 | SEQ ID NO: 98 | CTCGGTGCTGCAGCAGGAGGCTGGATCAATGACTACTACGGACG TAAAAA[G/A]GCCACCATGTTTGCTGATGTTGTTTTCGCAGCT GGAGCAATCGTCATGGC | G | A | A |
| SNP97 | 4 | 99.247 | 52528712 | SEQ ID NO: 99 | AGAATAGGGTTTACCTGCAACAAGATTCTCACAAGCTCCGTGCT TCCAAA[A/C]CGAGAAGCTTCAAGAAAGCATTGGTTCACGTTA TCCGCGCCTCCTTCCAC | A | C | B |
| SNP98 | 4 | 103.716 | 53075337 | SEQ ID NO: 100 | GTCAACCGTGTGGAGCTGCTAGCCAAGAAAATCACAGAGCTTGG TTACTC[A/G]TGCTTCTATATCCATGCGAAGATGGCTCAAGAC CACCGTAACAGGGTTTT | G | A | B |
| SNP99 | 4 | 104.352 | 53152564 | SEQ ID NO: 101 | GACAACATCTCTCTGATCTCACCGTTCACAACGCTCTGCACATC AGCAAA[G/T]ACCTTAGCCCACAACGGCTTCTCAGAGACCGGT AAATCGAAAAGATCATT | G | T | B |
| SNP100 | 5 | 4.966 | 1140114 | SEQ ID NO: 102 | GAATCTGTACATGTTCCTTTGTTTATATGGAGAACTCGTCCTTC AGACCG[A/G]GGGATGTGGGGAAAGGTGTCTCTACAGGTACT TTCTTCTGCAGAACTCG | A | G | A |

TABLE 2K

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP101 | 5 | 4.976 | 1141506 | SEQ ID NO: 103 | ACGACCCTTGGGATCGGGATAAGGAACGACACTGCACGTAGCGA TCTCTT[T/G]GTTGATTCGAGCTCACGGTACGAGATCTTCGCG GCGGAGTATCTCGGCGC | G | T | B |
| SNP102 | 5 | 7.820 | 1514669 | SEQ ID NO: 104 | AACAACCATCTCTGCAGGAAAGAGATAGAGAGACCATAAGAACT GAACTT[C/G]ATATGCATAAACATTTACAAAGTACCTTCAGCA GCATCTCCACTACCGCT | G | C | B |
| SNP103 | 5 | 7.820 | 1514715 | SEQ ID NO: 105 | ACTTCATATGCATAAACATTTACAAAGTACCTTCAGCAGCATCT CCACTA[C/G]CGCTAGAACCATCAGCGTTGTCAATCTCCATAG CAGGCTGCTTAGGAGCT | G | C | B |
| SNP104 | 5 | 15.375 | 2554344 | SEQ ID NO: 106 | TCACGGAGGGCAGTCGCAGTTGAATCATCTATTCCCAGCAGATA CTGTAG[T/C]CTCGACACCTTTTCTGGCGCCGGCTTGGGATCA CTCTTTGAATAGATACT | T | C | B |
| SNP105 | 5 | 15.608 | 2588838 | SEQ ID NO: 107 | GCGAAATGGACAGCAGTAAAAGGCGCGTTCATGAGAACAGTCGT CCTATA[A/G]GAAGCGTAGAACGCACCAAACCCTTCCTCCCTC ATAACCCTCCTCACGCA | A | G | A |
| SNP106 | 5 | 16.607 | 2732567 | SEQ ID NO: 108 | CATAGAAAAGCCACGAGCGAAGCAACCTCTTCAGGCTCCCCGAA ACGCCC[T/C]AACGGCTTTCTAGACGTTACAGCCTTCTTGAAG TCATCATCGTATACCTG | T | C | B |

TABLE 2K-continued

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP107 | 5 | 31.035 | 4956729 | SEQ ID NO: 109 | CTATGATGATGTCCTCGCCCACTGTCTCCCAAGACGCTCGAATAAACTCA[A/G]CTGAGTAGCCATCCGGTCACGGGCTCTTGTTCAGTGGCATAGAGAATAAT | A | G | B |
| SNP108 | 5 | 41.841 | 10181899 | SEQ ID NO: 110 | ACCTGGACCACCACCATCTCCAGCGCCTACTGCAGAAACCACAGACACAT[C/T]GTCACCTGCCGCACCACAACAACAACCAACACGGATGAGCACCAGAAACC | C | T | A |
| SNP109 | 5 | 44.362 | 12281717 | SEQ ID NO: 111 | TACCGTTAGTGCTCTGCTTCGGTTTATTCCTCAACTTTTGGCAAGCGTCA[A/T]GAGGATCAGCCACGTAAAGGACTCCGGTTTCTACCGTAGCCTCTTCTGAT | T | A | B |
| SNP110 | 5 | 47.460 | 18521685 | SEQ ID NO: 112 | TATACGCAATCCTGCAGCATAATGAACATCAGTAGGAGCTTGGACGAAACT[G/T]ACTAGTCTGTGAACAGTAAAGGTTATATCTGGACGAGTAATAGTCAGAT | G | T | A |

TABLE 2L

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP111 | 5 | 48.732 | 30884244 | SEQ ID NO: 113 | AGTCATCGGGCGTGGACCATGTTAGCGAACTCGCGCTTGTCTCTGCCTTG[G/C]ACTGACAAGATTTGATGGCGGAGACGGTATCGCAGCAGTATTGTGATCCT | G | C | B |
| SNP112 | 5 | 51.345 | 37641346 | SEQ ID NO: 114 | CCTGCAGAAGGTGGAGACCAGACCACTCTCGAAGCTGATGTTGTCCTCGT[G/C]TCAGCAGGAAGATCTCCCTTCACATCTGGACTTGATCTTGACAAAATCGG | G | C | A |
| SNP113 | 5 | 52.528 | 38794559 | SEQ ID NO: 115 | TCCCGAGTTGGCTGCAGGCGTACACCACCAGATGTAACAACTGTTTCCAG[C/T]AGCTTTTCCTCACGGGTTTTGCTCTCAAGACGAACTGAACCCGAACTTTC | T | C | A |
| SNP114 | 5 | 56.319 | 41364962 | SEQ ID NO: 116 | CTGGTTTCGATGATCTACGAAAAGGGCTTGACACTTCCTTGTCACTCGAA[T/C]CAAGGACACACCAGCGGCGAGATCATAAACCTCATGACGGTTGATGCAGA | T | C | B |
| SNP115 | 5 | 56.778 | 41506661 | SEQ ID NO: 117 | TGTATCAGCCGCCTATCTGGAAAATATACTTGTCTCCTAACAATCGCAGG[C/T]CTAATCGGACAGAAGAGGTGACAATAGATCTGTAACTTTCTCCTTGTA | C | T | B |
| SNP116 | 5 | 68.679 | 43448077 | SEQ ID NO: 118 | TTGGAACTTATTACTGTGTTTTTTGTTTCTGTGGGAGCAGGGATGAGAG[C/T]GTTACCAAAGCAGCGGTTGCAGCAATGGGTGATCTGGCAGATGTTGTAGG | C | T | B |
| SNP117 | 5 | 71.693 | 43800880 | SEQ ID NO: 119 | GCAGATCCTGGCTTCGGCGAACAATACACTGCCTCCAAAGATAACGCCAG[C/G]GGATTACAGAGCTGAAGTGCGCCGAGGATTGCTGACTCCAAGAAGTTCTA | C | G | B |
| SNP118 | 5 | 76.081 | 44280290 | SEQ ID NO: 120 | AATGTGTTTACTGTGCTGTGCTCGACGCTGAGCCATGCAGTGCGAACGGG[C/T]AAGAAAAGTCAAGGCACGTCTGAATCTGCAGCCAAGGAACCTGAGGAATC | C | T | B |
| SNP119 | 5 | 76.505 | 44322768 | SEQ ID NO: 121 | ATCCCATCCGATTTGACGGAGACGCCGAGAGATTCATCCTTCGTCGGCGT[T/C]GTCTTCTCCAAGCTCTCTTGATTGAAGAATCTCTGAAGACGAAATGGCGT | T | C | A |
| SNP120 | 5 | 76.505 | 44322808 | SEQ ID NO: 122 | TCGTCGGCGTTGTCTTCTCCAAGCTCTCTTGATTGAAGAATCTCTGAAGA[C/G]GAAATGGCGTTCTGGTGGCCGCTGATCGTTCTCGCCTTCGCTTACGCGAT | C | G | A |

TABLE 2M

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP121 | 5 | 81.616 | 44870044 | SEQ ID NO: 123 | GCGGTGACGGTGACGCCGCCGCCGACAAGGCGGCCACCGGGGAG GCCGCC[G/A]AAGAAGAAAACGCCGGCGGAGGAGGTGATGAAG CGGCAGCTGCAGTGTAG | G | A | A |
| SNP122 | 5 | 86.439 | 45492393 | SEQ ID NO: 124 | GACAGAGAAGAGTGCCTGACCACGTGGAGAAGAGCGTAGACGAA AACGCT[C/T]GAAGGTGCGTTCCCTTTGTTTGCTTCAGCTATG AGATCCCCATAGCTGCA | T | C | B |
| SNP123 | 5 | 86.707 | 45530316 | SEQ ID NO: 125 | GGGATCAGGAGCAGTATCAGTTGCAACACCAGGCTCATGGTGAG GCACAA[G/T]ATCACGATGGAAATGATGGGGGAGATCAAGTTG ATGAAGGTGAGGAAGGA | T | G | A |
| SNP124 | 5 | 93.187 | 46733625 | SEQ ID NO: 126 | CCCAGTGCCGTCACCAAAGGATGGAAAGCCAATCCTGTTGAATT TGATTC[C/T]GTCTTCAACAAGAGCAGACACACGTTTGCTTAT GGCAGTCCAGATATCAT | C | T | B |
| SNP125 | 6 | 4.372 | 724690 | SEQ ID NO: 127 | TGAAAACAGCATTCCACACTCACAACGGTCACTATGAATACCTA GTGTTG[C/T]CCTTCGGATTGTGCAATGCCCCATCGACATTCC AGGCGTTGATGAACTCT | C | T | B |
| SNP126 | 6 | 6.800 | 1007519 | SEQ ID NO: 128 | TTTCTGAGGTCATACTGTCGATTGATGCTGAGGTCGGATCTCCA GTGCTC[A/G]GCTCTCCAGATCCATGATGTTCATCTCTCTTTG CCATTCTGAGGTCGTCA | A | G | B |
| SNP127 | 6 | 22.962 | 2922287 | SEQ ID NO: 129 | TCGTAGTTTTCGTTCTGATCATCAAAACCGAAGAAGTCTTGTAT GGGAAG[G/C]GAGCTAGTCGTGAATGACGTGTCAAAGTCATCA TCGTCGCCAAGGATTGT | G | C | B |
| SNP128 | 6 | 24.373 | 3114174 | SEQ ID NO: 130 | AAGTGCATGGGCTAGCATCGTAGCTGCAGTTTCCGCCATCAAGT TGTGTG[T/G]TTCGCCTTCAAGTACCCTTTGTCTTCTTGTTTC ACTCTCCACCGGGTCTG | G | T | B |
| SNP129 | 6 | 28.036 | 3627446 | SEQ ID NO: 131 | AGGAGAGTTTCGTGGTTTTGATGGACGTATCTGAGAGTAAGCCT GCCTCC[A/G]GTCAAACGCAAGAGCAAAGGTATAACCGAACCA TCATCGTTGTTCGCAAC | A | G | B |
| SNP130 | 6 | 31.980 | 4189191 | SEQ ID NO: 132 | ATACTTTGATGGTGCAAAGATTGAATGCAGAGGTATGGCTTTTT TAGTCC[C/A]GTCCCTTCTGGATTGAATAGACTTTTAGCTACT GCTGCAGATTTGTTCAT | A | C | A |

TABLE 2N

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP131 | 6 | 39.058 | 5440585 | SEQ ID NO: 133 | GTTGTTTCGTGCAAATCTCACTGCTGCAGCTTGAGCATTCGTCA TAGTCT[A/G]GGAAGGTTGAGTTGTTGTTGCAGTCATACCAAG GACCGGCGTCTTCTCTT | A | G | A |
| SNP132 | 6 | 39.058 | 5440620 | SEQ ID NO: 134 | CATTCGTCATAGTCTAGGAAGGTTGAGTTGTTGTTGCAGTCATA ACCAAGG[A/T]CCGGCGTCTTCTCTTCTTGTCGCATAGCATTCA GATGGCATTCTTCTTGA | A | T | A |
| SNP133 | 6 | 43.889 | 6852182 | SEQ ID NO: 135 | TTCCCATCAACAACCTTTGTAGGATCAGCAAGCGCCGCCTGAGC ACCTTC[G/A]GAAGTCTTATACACAAACAAAGCAAACCCTCGT GACTTCCCAGTGACTTT | G | A | A |
| SNP134 | 6 | 44.870 | 7272721 | SEQ ID NO: 136 | ATAACAACAGATCCGTCTGCAGCTATTCCCAATACAAACTCTC AGCTCC[A/G]TCAGATCCTAGAGCTGCGAAAACAGAGGAGGTC TGAGCATCATAGACAAC | G | A | B |
| SNP135 | 6 | 48.965 | 10618159 | SEQ ID NO: 137 | ATCTTGATCTCTCTGCAGATCTGGCCACGAACAGTGTCATCGTG GTTACC[G/A]TTGATTATCTTGAGTGCGTATACGCGGGAGGTT GGACGGTGGACTACTCT | G | A | A |
| SNP136 | 6 | 50.138 | 13042773 | SEQ ID NO: 138 | ATAGCAAACCTGTTGGTGTAGTACTGATCTTGACAATTATAGCC AGCCAA[C/T]GTTCTGGGTCGACCAGACATAACATCTTCAGCA GCTGCAGCCCTCAACATT | C | T | B |

TABLE 2N-continued

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP137 | 6 | 50.525 | 13884163 | SEQ ID NO: 139 | AAATATGCGATCCGAATCCGAACGGATACCCGAACGTCGACCCC TAGCTC[T/C]GAAGGACAATGAAAACCAATCGATTCAGCGGCA TAGAGCCATAGAGGAAG | T | C | B |
| SNP138 | 6 | 52.027 | 15217464 | SEQ ID NO: 140 | GCCATTCTCCATCGAATTGAACAAGGTCTCGTTATCGATTTGGA GCCAGT[C/G]AGTCCTGATGAGGTCCCAGTCACTGCTGCTGGT GCGTTGAAGTCATACAA | G | C | A |
| SNP139 | 6 | 55.973 | 18016782 | SEQ ID NO: 141 | TGCAGTGAGAGCCAATGATGAATGGGTGCCCTACTCACCATCTC AAGCTG[G/C]TGTGTCTGACACAAAAGCCCGGGGAATAGCCAC ACAGGTTGGTCTTACTG | G | C | A |
| SNP140 | 6 | 66.709 | 24827566 | SEQ ID NO: 142 | GTAGAAAAGAGGGGAAGAGTATTTATGAGTGAGCAAACACCTAT CTATCG[A/G]GATTACAAATTAGTAGGAATAAAGTGCTTGCCT TCCCAAAGTCTATATCT | A | G | B |

TABLE 2O

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP141 | 6 | 67.753 | 29368693 | SEQ ID NO: 143 | AACTTTTCTTGAGAAACAACCGCAAACACGAGCGGGAAGAGTTG GTTTTC[A/G]GCATCAAACCCCGCGGCGACTAGCAGTTTTCCG GAGTGTTTACCGCAGTC | G | A | B |
| SNP142 | 6 | 67.775 | 30981277 | SEQ ID NO: 144 | AAACATGAGACCACACTGCAGTAGAAATTGGCTTGCCCGCTAAC GCTACT[C/G]CAAATAATTGATGCCATACCCAGACAGCTTTGC AGACCTCAGTCGAAAGA | C | G | A |
| SNP143 | 6 | 70.902 | 36429664 | SEQ ID NO: 145 | GCTTATGAGTTGTGTGTTTTTTCTATCTCAGATAAGTTGTATT GGGACC[A/G]TGCGGCTCATGTTGGAACAAACACACCAGGAGG ACTGGTACTAGTAGCGT | G | A | B |
| SNP144 | 6 | 71.169 | 36729257 | SEQ ID NO: 146 | CTGCTACACCCACCTCTTCATTCCCATGGGGTTGAAGTACTCCT CCTTGG[C/G]CATCGAACCCGTTGCTGTGAGGCGGTGCTTGTG AGTTCATCTCTATCTGT | C | G | B |
| SNP145 | 6 | 73.316 | 38879766 | SEQ ID NO: 147 | CTATCTGCAGGAGCCCTAATACTGACACGTGTAATCTCAAAATA TTCCAC[T/G]GCGAAGAAGTTGAGGTGACCCATTTTGCTGTTG ATAGATTTGATGCGGCT | T | G | B |
| SNP146 | 7 | 1.305 | 20364274 | SEQ ID NO: 148 | TTAGAACACCTGTGCTGCCGCACTGTGGTCAAGGCTTCTCTCAG AGCCAA[A/G]GCTTCCGCCATCAGAGGTGAGGCTACATACTCT GCTCGAGCTTGAAACTC | A | G | A |
| SNP147 | 7 | 1.653 | 25133727 | SEQ ID NO: 149 | GCAGTATACTCTGGTATGGTGATACCTCTGTACTTTGCAGGGCT TTCATC[A/C]GACAAAAGCTCTTTGATCGGTTCATAAACCGTG TCATTTGGAAACAGACT | A | C | B |
| SNP148 | 7 | 3.260 | 29384441 | SEQ ID NO: 150 | TCATCGCTCACGTCACTGCTCGTGCTTCCTCTGTAGATACTGCT TTTGCC[G/A]CTCTCCATGAAATCAAGGCGGCTTCCACTAAGC TTGGCGCTTCCGCTCGT | A | G | A |
| SNP149 | 7 | 12.311 | 33894835 | SEQ ID NO: 151 | TCGTTACCGGTCCGAGCGCCGTCGCTGGTTTCTTCCCGGAGAAT CTTCCA[G/A]GAGAAACTCCACGAACTTCCCAGGTGCGCCAAT TTAGCCCAAGTGAAGCA | G | A | B |
| SNP150 | 7 | 13.369 | 34371604 | SEQ ID NO: 152 | GAACGGTTAGTTTCTCCACTAATTTCTCCAAATTCAGACACGGG TTTGGT[C/T]TTATTCAGACATGTGGTTTAGTCAACGTAAAGC TAAAATGGGTAAAAGAC | T | C | A |

TABLE 2P

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP151 | 7 | 13.825 | 34583372 | SEQ ID NO: 153 | TACTGCAGAGATGCGCAAAGCCGAGGTCACGTGAGGCCAAGAA A CTTGATA[G/A]AGAAGCAGAGCCTAGCTCTTTTCGGTCCCGA GGGAAAGGAGGAAGAGAGC | G | A | B |
| SNP152 | 7 | 25.291 | 38743951 | SEQ ID NO: 154 | GGGTTTAGTACAATAGCCTCTGCAGTTGGTTACCCTGTCCACT T CTGAGTT[C/T]GCTGACCTCAAGACATACACGAATGGTGTGA TAAAGCTTCGTGTTGTAGT | C | B | |
| SNP153 | 7 | 28.998 | 40014701 | SEQ ID NO: 155 | AACATGAGTGTCCTCTTCTCTCCGAGGAACCCGGATCGTGTCC G CGATTCC[G/T]ACACTGAGACGTTTCTTTGGTGACGATTATT ACATCTGCAGGTTTCAGGT | T | B | |
| SNP154 | 7 | 37.842 | 43233659 | SEQ ID NO: 156 | CTGCAGTATATTTTTTGGAATCACACTCTGCAAATCTGATCTT A TCTTGTT[A/C]TCTTTCTCTATCCCCTAATCTAAAAGATACT ATCAACGAAGCGAACTTGC | C | A | |
| SNP155 | 7 | 38.592 | 43345503 | SEQ ID NO: 157 | TCACTGCAGTGAGTCTCATAAAGTACCATTTTATTTTGATTAC G AGGCTGG[G/T]GTTCTGGCTGGAGATGTGAGCGACATTGTCC TTCTCGACGTGACGCCGCT | T | A | |
| SNP156 | 7 | 41.700 | 43818102 | SEQ ID NO: 158 | TCATCAAGTGGCACCATAAGAGGGTTCGCCTCATCCATCTCTA G CATTCAT[G/A]TCTGAATCGTAATCTAGTTTCATTTCTTCAT CTCCATCACCCTCCTGCAG | A | B | |
| SNP157 | 7 | 43.584 | 44096110 | SEQ ID NO: 159 | ATTTTGAGATGTCTGGACTGTTTCATCCTGATCAGATCCGGTT T GGTGGCG[T/A]CTGAACAGGAGGAGCTGCCCGGCTTAGGTTG GTTGAGGAAGCTGCAGCAG | A | B | |
| SNP158 | 7 | 44.266 | 44191945 | SEQ ID NO: 160 | GGTAAGGCTTCTCGAGGAACCTCGTGTAGAGTGTAAGTGAGAA C ACGAGGG[C/T]TTGGGGTTTACTACTATTCTTGGACATTCGA TGGACAGCATCTCCAATGA | T | A | |
| SNP159 | 7 | 44.266 | 44191975 | SEQ ID NO: 161 | GTGTAAGTGAGAAACGAGGGCTTGGGGTTTACTACTATTCTTG A GACATTC[G/A]ATGGACAGCATCTCCAATGAGTCCTTATCAA TTCGTGGCTGCAGAAGAAG | G | A | |
| SNP160 | 7 | 46.334 | 44490415 | SEQ ID NO: 162 | AGCCACAAAGAACGAGAAATCACTTCTTTCCAGTGCTTGTGGG A AGATTTG[G/A]GCATGGAGATACAGAGATCAGAAGCCACCTG ATGTTTGCTCATGAGATGG | G | B | |

TABLE 2Q

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP161 | 7 | 48.124 | 44794150 | SEQ ID NO: 163 | GTGAACATGCCATCCACTTCGCTGTCTCCTGCGGGTACCTCAA T AAAGAAA[T/C]GTCGGACAATCAGGTTTCCCTCCGGAAACCA CAAATGCTGGGTATGAAAG | T | C | B |
| SNP162 | 7 | 54.996 | 46191816 | SEQ ID NO: 164 | TGAAACTCATATGGTAATATAATTTTTTTTCTTCCTCATATTC ATTCTGT[T/C]TCACTTTGAGGCTTGATGAATGAGTGTCTTG TGACAGGTGGAACTAGAGG | C | T | B |
| SNP163 | 7 | 61.162 | 47585593 | SEQ ID NO: 165 | ACACGCATTGGTAACCTCTCGTTCTGAACAGCGTGCGCGCAAG CTTCTAC[T/A]AGATAGCTTCCTACAGTCCATTAGCCTGCAGA TTCTCTTCTTCTCGCTCTT | T | A | A |
| SNP164 | 7 | 61.702 | 47714484 | SEQ ID NO: 166 | GGTGGTGGTGCTGCAGGAGGCGGCGGAGGTACGGTAGAGGGTG ATGGAGG[G/C]ACAGCGAAAGGAGCTTTCTCCGTCGTCACAA AGCCTCGCTTCTTCAACCC | C | G | A |
| SNP165 | 7 | 63.419 | 48124324 | SEQ ID NO: 167 | GTGCAATCAGCTGAGAAGTGACCTTGCTTGTAACAGTTGTTGC AGAGTCT[C/A]AGGTCACCAGGAGGGAGGTGGCGAGCCGTGC AGTCTTTAGCTTGGTGTCC | A | C | A |
| SNP166 | 7 | 63.806 | 48216530 | SEQ ID NO: 168 | ATCCCGAGTACTTGACTCTCTGCCTGACCACGGTAGACTTGAT TCTCAGA[G/A]ATTTTTTGACGCCAGAGACATGGTTCCCAAT TATACAGAGTCATCTCCGC | G | A | B |

TABLE 2Q-continued

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP167 | 8 | 0.016 | 148296 | SEQ ID NO: 169 | CAGGTTCCTGGAGGGACAACACTGTTGGAGCATTTGCAAGGTA AAGTTTC[G/A]ATAGAAGAGAGTGTGATGAGTGCTGCAGCAG AAGCTGTGAGGGCAGCAAT | A | G | B |
| SNP168 | 8 | 0.016 | 2426797 | SEQ ID NO: 170 | ATGATTTCGGAAAAGAAGCAGAAGCTAGAGCCGAAGAGAAGGA GACAAAA[G/C]CGATGAGCTGGAGAAGGAAATGGTAGTGACC TTCAAGACCTAAGTGATCA | G | C | A |
| SNP169 | 8 | 0.032 | 13520717 | SEQ ID NO: 171 | CGCCGAACCCTGATCAACCGAGATCGGTGCAGGAAGCCACCGT TGAGACG[C/T]GTCGTCCAATCTCTGACGGATCTCAGCCTCA ATAAAAGGGCTGCAGATG | C | T | B |
| SNP170 | 8 | 2.152 | 18675613 | SEQ ID NO: 172 | TGACCGCAAGCACATCTGACATCTCGGCCCGTTGAGAGATCCA TATGGCG[G/A]ACTCGAATCTTGCCCCAACTGCAGCGCCTGT AACCCCACACATTTTTTAA | A | G | A |

TABLE 2R

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP171 | 8 | 4.123 | 19739628 | SEQ ID NO: 173 | ACCACTCGTTTCCAATGACGCTATTCGTTCCTCGGACCACACA TCTGGAT[C/T]ACCGCACGCTGGAACAGCTCAATAACTGGAC GTGGCAGTTCTGTGTTATC | C |  | B |
| SNP172 | 8 | 4.915 | 20071352 | SEQ ID NO: 174 | GCTCTACTCATCTGCTCCAGCCTCACCGCGCTAATGGGAGGGA GACTAGT[G/C]GCAGCGCCAACGCTTTGGCCTGAGTTACTAC CTCCTCCTGTTGTTAAACC | G | A |  |
| SNP173 | 8 | 11.767 | 24841237 | SEQ ID NO: 175 | ATATGTACTCCGGCGAGTGGAATTTAGTGAAATCTGAATGTTG GGCAGGG[G/C]GAGGGCGGATGATATCCATGTAGCGAGGGAG GTAATAGCTGCAGATGAGG | C | B |  |
| SNP174 | 8 | 13.753 | 26341786 | SEQ ID NO: 176 | TAGATGAAAGCCAAGGTAGAGAAAGGGCAATAAACCAAGTATA TGAGATC[C/G]AACAAGACGCTAGATATGAACTTGCTGAAGG AGCTGCAGCTCCTGGAATA | G | A |  |
| SNP175 | 8 | 21.371 | 28667380 | SEQ ID NO: 177 | TTCTGCCAGTCACTTTATCATAGATAACCTACAAACAAAACCA AACCCCA[A/T]TTCATCATAAATTCAAAACAAAACCAAATCT CAAATTATCTTCAAAGACC | A | A |  |
| SNP176 | 8 | 31.456 | 31835841 | SEQ ID NO: 178 | ACGAGGCCATGGTCAGAATCAGCTGCAGCTGGATCAGCTGGTT ACGTTGA[T/C]TGTCCAGCTGTATGTTCACGTAATCTTCCGT GTCGTCAATGTATTCCCTC | T | A |  |
| SNP177 | 8 | 32.905 | 32719677 | SEQ ID NO: 179 | CATGTTCACTATTATCATTCTGCACGCTTGTTCCATCCTTAGC CACAGAT[T/G]CTACAACATTGTCATCACCTGTTTTAGCTTC TCTCTGCAGCAGAACAAGA | G | B |  |
| SNP178 | 8 | 35.366 | 33804788 | SEQ ID NO: 180 | AAGAAAGAAAAGCTCCTCGCCAGCTGAGGAGGAGGAAGCAGCG GGACCTTG[T/C]GGGTACGTGTGCGGGGTCCTCGGGAGAGAT CTATCGGAGGATCCTTGGC | T | A |  |
| SNP179 | 8 | 40.549 | 35972043 | SEQ ID NO: 181 | ATAATCGTTGCGGTGGCGGTTCCAGTTTCGCCGCCGGACCAGC ACTCGCC[T/G]AGGTTGGGACACTTAGCCTCCTCGCAGACGG TGTGAAGGTTAAGGTCTCT | G | A |  |
| SNP180 | 8 | 45.635 | 36966286 | SEQ ID NO: 182 | CGTCGAACCTCGGTTTAGCACGCAACCAGTGGTACAACACATC CAGCCAT[T/C]TCGGAAGAAGAACCTCTCCATCAGATACAGC CATTAGGTGTATCGGCACT | C | B |  |

TABLE 2S

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP181 | 8 | 49.698 | 37687701 | SEQ ID NO: 183 | AATCCAGAAGTTGAAAAGAAAGCGAGATCTTTGGCTATAACCTCCACTATC[C/G]GATCACACTCAACTCTGTTTTTGGCCCTCAACTGTCGCAGCCGGGCTTGT | C | G | A |
| SNP182 | 8 | 53.908 | 38577262 | SEQ ID NO: 184 | AGGAAGCTAGAATATCTACACTTGTGGGATTTGCCTGAGCTGACTGAGCAT[C/A]TACTGGAGTCCTTTGCCGTTTCCGTATTTGAGTCTGATCAATGTACAAAA | C | A | A |
| SNP183 | 8 | 62.287 | 40758807 | SEQ ID NO: 185 | GCGTGGAGAACATCTCCACCGAAGTCCTCAAGTCCTTCAAAATGCCGGCAC[A/G]ACTTTCTCAGCATTCTCTCCCGTAGCCACCACAAGCGTCCTGCAGATATA | G | A | B |
| SNP184 | 8 | 62.374 | 40785808 | SEQ ID NO: 186 | TTGTCGATCAAGGAAGAGGACAGTCAAACTGAGCGGGAGATGGAAGATAG[T/G]TTTGATAATGAACAACCACCAAGTCCTCCTATGCATTTATCTGCAGGGCT | T | G | A |
| SNP185 | 9 | -0.030 | 313527 | SEQ ID NO: 187 | CTCCCGGTTGATCATGTTCTGAAGTTCCATGAATGCTTGTTCCGCATGGAA[G/C]CTCCTCCATCTCCTTTGGAATGGTTAGATACAATATATTCTTGGAAGAAC | G | C | A |
| SNP186 | 9 | 0.104 | 330755 | SEQ ID NO: 188 | TGCTTCCTCCTTTCACTGCCGTTTTCCCTCGTTAGCGGTTACACTCCTCCG[T/C]ACCCCCGCCGCTGAGAAACTTGTTGAAAGTCTCGGCGTCGGGAACAGTGC | T | C | B |
| SNP187 | 9 | 0.183 | 340706 | SEQ ID NO: 189 | GAGAAGAAGAGCTAGAGGCAGGGTTTCCCAGAAGTGACTGTGAGATCAGAA[G/A]AGCTGTACAAGTAAGCAGGTTGAAGCAAGGGTGCGTTTGAAGCAGGGATG | G | A | B |
| SNP188 | 9 | 1.079 | 455157 | SEQ ID NO: 190 | TAAGTGAGACAGTTGTTACAGTTTTTCTCAGACAAGTCTGGCGCTGCACTG[T/C]ACGGAAGCGAAGAATCTAGTGTAAGGTGGAGAAGCAGGACCATCTCCTTG | T | C | B |
| SNP189 | 9 | 7.242 | 1254086 | SEQ ID NO: 191 | TTCTCCTTCTCACGTAACCGATCCTCTAAACGATCTTTGGCTGGATCTGAG[A/G]GAGAGGAGGTTTCTCTTCAGCTGCAGATTCTCGGTTTCTGCATCTATCAA | A | G | B |
| SNP190 | 9 | 10.178 | 1639986 | SEQ ID NO: 192 | ATTGAGGTGTCTATTCAGGGTGAGCAGTTCACCAAGACCTTCACAAGTGGA[T/C]CTTTTGCCAAAGATTTATGAGACACTACAGAAGTTGGTTGGGCTGTTGAA | T | C | B |

TABLE 2T

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP191 | 9 | 15.497 | 2355085 | SEQ ID NO: 193 | CTGCAGAATCAACAGTCTAAGCTGGTGTCTGAAGACCACATAAATCTCGA[C/T]AACAAACAAAACATAGCTACATATTTCTCTTACCCGACTAGTGTCTACAA | C | T | A |
| SNP192 | 9 | 26.071 | 3745424 | SEQ ID NO: 194 | GGGAAAGAGCCTCTGGCTTAGCTAAAGACGTCATCATCTGCTCGAGCTGC[C/G]GTTTCAGTTCCTCGAGGTGGGATAGAGTTTGTTTCACAGCCTCCATAGCT | C | G | B |
| SNP193 | 9 | 30.177 | 4464952 | SEQ ID NO: 195 | TTCTTGTACATGATAACGTGGTGGCATCCATCTTCTTTGGCTTGAGCCGC[T/C]TTCTCATTGGTCGAGACAGTTCCAATGACGGTAGCTCCAAGCGCATTTGC | T | C | A |
| SNP194 | 9 | 32.759 | 5079336 | SEQ ID NO: 196 | CTCTACTCCAACCGCAACTGCAGTCTGCAAGAAACCAACCTTTCAAGAAC[A/C]AAAACCTTACCAACAAGCATAGAAGAAGTGAAGGAGAGATGAAAGGACCT | A | C | A |
| SNP195 | 9 | 41.524 | 7839999 | SEQ ID NO: 197 | TGAAGACGGTTACGTTGTGACTAAGCCTGGTACTACGAAGACGAGCGTGG[C/A]TGGTGTGTTCGCTGCGGGAGATGTGCAAGATAAGAAGTACAGGCAGGCCA | C | A | B |
| SNP196 | 9 | 45.092 | 9246116 | SEQ ID NO: 198 | GGAGGCGTTCTCTCCGCGCTTGCAACGTTCAGGATTCTTCAGGAGCCGCT[T/C]AGGAATTTTCCTGATCTGGTGTCAATGATGGCTCAGACTAAAGTGTCTCT | C | T | B |

TABLE 2T-continued

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP197 | 9 | 53.464 | 17031088 | SEQ ID NO: 199 | TAGCTTCTTAGGTCCACTTTTTGTGCACACTGCTCTTCAAACA GGTGGCT[T/G]CATGTCCTCTTACTCCCTGGGCTCTTGCTTG TCTGTCTTTCTAGCTTGTT | T | G | B |
| SNP198 | 9 | 58.238 | 42755363 | SEQ ID NO: 200 | TTTGACCCGCCGGAGACTTGACAAAAGGAACCAGGGCAGCCGA GGATGAT[G/A]ATCTCGTCTTCATCTGTTCTTTGCCTAAACC TGAGTTGAGTTTAGCTGGT | G | A | A |
| SNP199 | 9 | 60.841 | 44984162 | SEQ ID NO: 201 | CTTCCGCAGAATCAGCTTTATAATGGTCATCAAGCAACACAGC AGCATCA[G/A]GCACAACAAACATCTATGCATCATTTGCAAC CCCAAGTAGTTTCGGGATC | G | A | A |
| SNP200 | 9 | 69.310 | 48249783 | SEQ ID NO: 202 | ATTGTAGTGACCATTTCCATCTCTCTCTTCACCATCATCCCTC TTCTCTA[C/T]CCTTTTGTTGAAGACCCTAACTTCTTCTTCA AGCAACAACATCCAAGTCA | C | T | B |

TABLE 2U

| SNP ID | Chr | cM | Location of SNP on chromosome | SEQ ID NO: | [SNP] and its adjacent sequences (5'→3') | A | B | Direct line |
|---|---|---|---|---|---|---|---|---|
| SNP201 | 9 | 70.587 | 48542186 | SEQ ID NO: 203 | AAGAAGATCCAGTCGATGAAGGACAAGAATCTGAGGTCGGA GATGGAGAC[C/T]GTCACCAGGGACGCGAGGAGGCTCGCG GTTTCGTACTGCAGGATTCACCT | C | T | B |
| SNP202 | 9 | 73.370 | 49125336 | SEQ ID NO: 204 | TTCAATGCGCTTGCTATCAAGAGATTGAAGGAGATTCAGTG TTACCGTGG[C/G]GTTAGGCACATCCAAGGGTTGCCGTGT CGTGGACAGAGAACCAAGAACAA | C | G | B |
| SNP203 | 9 | 77.936 | 50007823 | SEQ ID NO: 205 | AAGGAAGCAGGCTTTGCACGAACGTCGGTTGGCACTTGAAC AAGATGTAC[T/G]AACCTTCTCTTGAGTTTTTGTGTTTCT ATTCTCCAATTTTTATTCATAAT | G | T | A |
| SNP204 | 9 | 82.039 | 50576467 | SEQ ID NO: 206 | TAACAAACGTACCTTACAAATGGCAAGGCAGGGTCAGCACA GCGAGTTCC[C/T]GAAGGCAATCTATCCGCTGAATTTGCA AGGGAGCTAGCAAGACCATTTTG | C | T | A |
| SNP205 | 9 | 95.733 | 51845327 | SEQ ID NO: 207 | TCCTTTTCAGCTGTTTTAGCACTTCGTCCACGTCCCCTTCC ACGCCCTCT[G/T]CCTCTACCCCTTCCACTGGGTCCCACT TGCCCCGTCTCATGCTGCAGTGA | G | T | A |
| SNP206 | 9 | 100.571 | 52317409 | SEQ ID NO: 208 | GTCACCTCTCAGCAGGAATCGATTCAAGAGCTCTACGCTGA GCTCGACGA[A/G]GAGAGAAACGCGGCTTCCACGGCTGCG AACGAGGCGATGTCTATGATACT | G | A | B |
| SNP207 | 9 | 106.361 | 53047247 | SEQ ID NO: 209 | CCTACTATCCTAAGGTTAGTCTCGATGTTCCCAGCAACCTT TCTTAGCAA[C/T]CCGGCTCTACCAATCAAGGCGGTGCTT GCCGCCTCGAACGAAGAATGCCA | T | C | A |
| SNP208 | 9 | 111.615 | 54261547 | SEQ ID NO: 210 | TTAAACAACAGGGGAAGAGGTGGTTTTACGGGCGGCCTCG TGGTGGTTT[A/T]GGCGGTGGTAATTTCCGAGGTGGTAGA GGAGGCAGGGGAGGTAGAGGAGG | A | T | A |
| SNP209 | 9 | 112.468 | 54570013 | SEQ ID NO: 211 | GCATCTGACATCATTGTCGAGACAGCAGAGGCATTCCTGCC AAAACTCGG[G/A]TCTGCACGGCTTGTCCTGGTTGACTTG AGCCATGGGTCGAAGATTCTGTC | G | A | A |

<Progeny Line>

The broccoli plant of the present invention may be a progeny line of a deposited line. The progeny line may be a plant individual of a progeny line, a part of a plant individual of a progeny line, or a seed of a progeny line.

In the present invention, the "progeny line" or the "progeny broccoli plant" (hereinafter collectively referred to as the "progeny line") is a plant obtained from a broccoli plant of the deposited line or the progeny line thereof. In the present invention, the progeny line may be a plant obtained from crossing the deposited line with another deposited line or another broccoli plant, or by crossing the deposited line with a wild broccoli plant. The progeny line may be obtained, obtainable, or derived directly or indirectly through self-crossing and/or cross-pollination of the deposited line or a progeny line thereof. Also, the progeny line may be derived from a parental line obtained from the deposited line using traditional breeding methods such as self-crossing and/or cross-pollination. Examples of the progeny line include self-crossing progeny lines and first-generation hybrids F1 (hybrid first-generation line, F1 hybrid). In obtaining the progeny line, the deposited line may be used as a female parent, a male parent, or both parents.

The term "crossing" as used in the present invention refers to the crossing of two parent lines. The crossing may be "cross-pollination" or "self-pollination." Cross-pollination refers to fertilization by the binding of two gametes derived from different plants. Self-pollination means that pollens migrate from the anther to the stigma of the same plant. Self-pollination can also be referred to as self-crossing, for example. The crossing may include backcrossing, which is one of the traditional breeding methods.

The "backcrossing" is one of the traditional breeding techniques in which a breeder repeatedly backcrosses a progeny line of the hybrid to one of the parental lines and introduces a characteristic into a plant or a variety. A plant including the characteristic to be introduced may be referred to as a donor plant, for example. A plant into which the characteristic is introduced may be referred to as a recurrent parent, for example. The backcrossing can be performed by crossing a donor plant with a recurrent parent, thereby obtaining a first-generation hybrid F1 (hybrid first-generation line, F1 hybrid). The progeny line having a characteristic is then crossed with a recurrent parent. Then, by backcrossing and/or self-crossing several generations, the characteristic of the donor plant can be introduced into the recurrent parent.

In the present invention, the progeny line may be regenerated from a cell culture or a tissue culture derived from the deposited line, a protoplast, or a part of a plant individual; may be obtained by self-crossing the deposited line; or may be obtained by producing seeds from the plant individual of the deposited line.

The term "regeneration," as used in the present invention, refers to the development or vegetative propagation of a plant from a cell culture, a tissue culture, or a protoplast.

The "tissue culture" or "cell culture" may be a composition including the same or different types of isolated cells or may be a collection of cells that are organized into parts of a plant. Tissue cultures of various tissues of broccoli plants and methods for regenerating plants from the tissue cultures are well known, and reference can be made to References 3 to 5 below, for example.

Reference 3: Lise N. Hansen et al., *Genetic analysis of protoplast regeneration ability in Brassica oleracea*, Plant Cell, Tissue and Organ Culture, 1999, vol. 58, pp. 127-32.

Reference 4: Ravanfar S. A. et al, *Plant regeneration of Brassica oleracea* subsp. *Italica (Broccoli) CV Green Marvel as affected by plant growth regulators*, African Journal of Biotechnology, 2009, vol. 8, no. 11, pp. 2523-28.

Reference 5: Jong Hee Kim et al., *Callus Induction and Plant Regeneration from Broccoli (Brassica oleracea var italica) for Transformation*, Journal of Plant Biology, September 2002, vol. 45, no. 3, pp. 177-81.

The progeny lines may have desired characteristics. The progeny lines may have "essentially all physiological and morphological characteristics of the deposited line" when they are cultivated in the same cultivation conditions, for example. Specifically, the progeny line may have a common characteristic with the deposited line. As a specific example, 1 or more, 2 or more, 3 or more, 4 or more, 5 or more, 6 or more, 7 or more, 8 or more, 9 or more, 10 or more, 11 or more, 12 or more, or 13 or more characteristics of the progeny line match the characteristics of the deposited line. The progeny line may be a plant having the main characteristic of the deposited line. The main characteristics are characteristics of Characteristic Nos. 9, 13, 21, and 36 in Tables 1A and 1B, i.e., the characteristics of (1) to (3) and (9). The progeny lines may be, for example, plants having the same characteristic as the deposited line, except for 13 or less, 12 or less, 11 or less, 10 or less, 9 or less, 8 or less, 7 or less, 6 or less, 5 or less, 4 or less, 3 or less, 2 or less, or 1 characteristic, i.e., 13 or less, 12 or less, 11 or less, 10 or less, 9 or less, 8 or less, 7 or less, 6 or less, 5 or less, 4 or less, 3 or less, 2 or less, or 1 characteristic may differ from the deposited line. The "characteristic different from the deposited line" may be a main characteristic of the deposited line or a characteristic other than the main characteristic of the deposited line, and is preferably a characteristic other than the main characteristic of the deposited line. The "characteristic different from the deposited line" can be made, for example, by the introduction of a characteristic and/or introduction of a gene, which will be described below. In the progeny lines, all the characteristics of Characteristic Nos. 1 to 38 may be the same as the deposited line. Examples of the characteristic different from the deposited lines include diamondback moth (*Plutella xylostella*) insect resistance, fall armyworm (*Spodoptera frugiperda*) resistance, LSL (Long Shelf Life, stay green, ethylene insensitive), and characteristics of coloring green even under weak light (characteristics of coloring green even in hidden areas). Each characteristic can be introduced, for example, by crossing with a known plant having a locus associated with each characteristic.

The progeny line may include a cell containing at least one set of chromosomes derived from the deposited line. At least 6.25%, 12.5%, 25%, 30%, 35%, 40%, 45%, 50%, 55%, 60%, 65%, 70%, 80%, 85%, 90%, 95%, 96%, 97%, 98%, or 99% of allele of the progeny line may be derived from the deposited line. That is, the progeny line may have at least about 6.25%, 12.5%, 25%, 30%, 35%, 40%, 45%, 50%, 55%, 60%, 65%, 70%, 80%, 85%, 90%, 95%, 96%, 97%, 98%, or 99% genetic complement with the deposited line.

The "allele" is any one or more genes, and all of which are associated with a trait or characteristic of a broccoli plant. In a diploid cell or organism, a pair of alleles of a given gene occupy the corresponding locus on a pair of homologous chromosomes.

The genetic complement can be calculated, for example, by decoding a molecular marker or a base sequence, comparing it with a molecular marker or a base sequence of a Takii 12, and calculating a concordance rate. Examples of the molecular marker include SNP markers, amplified fragment length polymorphism (AFLP) markers, restriction fragment length polymorphism (RFLP) markers, microsatellite markers, sequence-characterized amplified region markers, and cleaved amplified polymorphic sequence (CAPS) markers. Methods for analyzing genomes using the molecular markers are well known and widely published (e.g., References 6 and 7 below). The base sequence can be decoded, for example, by extracting a chromosome from the progeny line and sequencing the chromosome. The proportion of allele derived from the deposited line and the proportion of genetic complement may be estimated, for example, by the number of times of crossing. In this case, the proportion can be estimated from the number of times of crossing from the deposited line. As a specific example, when the number of times of crossing from the deposited line is n, the proportion can be estimated to be, for example, $(1/2)^n \times 100\%$.

Reference 6: Sinchan Adhikari et al., *Application of molecular markers in plant genome analysis: a review*, The Nucleus, 2017, vol. 60, issue 3, pp. 283-97.

Reference 7: Elcio P. Guimaraes et al., *MARKER ASSISTED SELECTION Current status and future perspectives in crops, livestock, forestry and fish*, 2007, Springer, pp. 29-49.

Preferably, the proportion of allele derived from the deposited line and the proportion of genetic complement is, for example, an average value of the proportion of a plurality of progeny lines. The "plurality" here, for example, is the number of individuals capable of subjecting statistical examination, and, as a specific example, is 200 individuals or more, and preferably 200 to 1,000 individuals.

The progeny line may have an SNP derived from the deposited line. The SNPs of the deposited line are the SNPs shown in Tables 2A through 2U. At least 6.25%, 12.5%, 25%, 30%, 35%, 40%, 45%, 50%, 55%, 60%, 65%, 70%, 80%, 85%, 90%, 95%, 96%, 97%, 98%, or 99% of the SNPs of the progeny line may be derived from the deposited line, for example. That is, at least about 6.25%, 12.5%, 25%, 30%, 35%, 40%, 45%, 50%, 55%, 60%, 65%, 70%, 80%, 85%, 90%, 95%, 96%, 97%, 98%, or 99% of the SNPs of the progeny line may match the SNPs of the deposited line. In the present invention, if 50%, 55%, 60%, 65%, 70%, 80%, 85%, 90%, 95%, 96%, 97%, 98%, or 99% or more of the SNPs of a target broccoli plant match the SNPs of the deposited line, for example, the target broccoli plant can be determined (discriminated, estimated, appraised, or distinguished) to be a progeny line of the deposited line. For example, the progeny line preferably has at least one SNP selected from the group consisting of SNP7, SNP8, SNP20, SNP21, SNP75, SNP78, SNP81, SNP84, SNP90, SNP142, SNP165, and SNP177 among the SNPs of the deposited line, and more preferably has at least one SNP selected from the group consisting of SNP78, SNP81, and SNP142 among the SNPs of the deposited line.

The progeny line may have, for example, a mutation or transgene. In this case, the progeny line has, for example, one or more characteristics modified. The progeny line can be produced, for example, by transferring a mutation or a transgene into the deposited line or a progeny line thereof. The mutations may be introduced artificially or may be introduced naturally. The mutation may be, for example, a chemical-induced mutation or a radiation-induced mutation. Also, the mutation may be introduced, for example, by a molecular biological procedure or a genome-editing technique (e.g., Reference 8 below). As to the transgene, a method using *Agrobacterium tumefaciens* can be given.

Reference 8: Yanfei Mao et al., *Gene editing in plants: progress and challenges*, National Science Review, 2019, vol. 6, pp. 421-37.

Examples of the one or more characteristics include diamondback moth insect resistance, fall armyworm resistance, LSL (stay green, ethylene insensitive), and characteristics of coloring green even under weak light (characteristics of coloring green even in hidden areas).

The "transgene" refers to a desired gene introduced into the genome of a plant, e.g., by a genetic engineering procedure or a traditional breeding method. The transgenes may be derived from the same species or from different species, for example. The transgene may be a gene having the same base sequence as or a different base sequence from the species from which it is derived, for example. In the latter case, a different base sequence can be prepared, for example, by performing codon optimization, the addition of a transcription control factor such as a promoter, or the like, to the same base sequence. The transgene may have a translated region and an untranslated region.

<Haploid Plant and Doubled Haploid Plant>

The broccoli plant of the present invention may be a haploid plant and/or a doubled haploid plant that is obtained, obtainable, or induced from the deposited line. The haploid plant and/or the doubled haploid plant of the deposited line may be used in a method for producing a parent line of the deposited line. In one embodiment, the present invention may provide a plant of a haploid plant and/or a doubled haploid plant, a plant part of a haploid plant and/or a doubled haploid plant, or a seed of a haploid plant and/or a doubled haploid plant.

The doubled haploid plants can be produced by doubling chromosomes in haploid plants or cells (e.g., Reference 9 below). As a specific example, haploid pollens are cultured under predetermined conditions to form 1n chromosome plantlets. The chromosomes are then doubled by treating plantlets with chemicals such as colchicine, for example. Thus, the cells of the plantlets have chromosomes of 2n (doubled haploids). Then, by growing the plantlets after the treatment, it is possible to obtain the doubled haploid plants and progeny lines.

Reference 9: Jim M. Dunwell, *Haploids in flowering plants: origins and exploitation*, Plant Biotechnology Journal, 2010, vol. 8, pp. 377-424.

<Method for Producing Broccoli Plant>

As described above, the method for producing a broccoli plant of the present invention includes the step of crossing a first broccoli plant with a second broccoli plant, wherein the first broccoli plant is the broccoli plant of the present invention. The production method of the present invention is characterized in that the broccoli plant of the present invention is used for at least one of parents in the crossing, and other steps and conditions are not particularly limited.

Further, the method for producing a broccoli plant according to the present invention includes the step of self-crossing (self-pollinating) the broccoli plant according to the present invention. The production method of the present invention is characterized in that the broccoli plant of the present invention is self-crossed, and other steps and conditions are not particularly limited.

According to the production method of the present invention, a progeny line of the deposited line can be produced. Regarding the production method of the present invention, reference can be made to the description as to the broccoli plant of the present invention.

In the present invention, the crossing between the first broccoli plant (first parental line) and the second broccoli plant (second parental line) may be, for example, crossing between the same individuals (regular self-pollination), crossing between individuals of a line maintained in the same clonal individual or inbred line (quasi-self-pollination), or crossing between different individuals (cross-pollination). In the case of the regular self-pollination, one of the first parental line and the second parental line is a female organ in the same individual and the other of which is a pollen in the same individual. The quasi-self-pollination may be, for example, a case where the S genotype related to self-incompatibility is the same, and the cross-pollination may be, for example, a case where the S genotype related to self-incompatibility is different. In crossing of broccoli plants, preferably the first parental line and the second parental line are of different S genotypes and the crossing is cross-pollination.

In the present invention, the first parental line is the broccoli plant of the present invention, e.g., a broccoli plant deposited under the Accession No. FERM BP-22393 or a progeny line thereof.

The second parental line is not particularly limited, and any broccoli plant can be used. The second parental line may be, for example, taxonomically a broccoli plant of the same species or a broccoli plant of different species with the first parental line. The second parental line may be, for example, the deposited line or the progeny line or other broccoli plant.

The production method of the present invention may further include the step of growing a progeny line obtained in the crossing after the crossing, for example. Growth conditions in the growing are general growth conditions for broccoli plants.

The broccoli plant of the present invention can be obtained, for example, by the production method of the present invention.

<Method for Producing a Seed of a Broccoli Plant>

The present invention provides a method for producing a broccoli seed. The method for producing a broccoli seed according to the present invention includes the steps of self-crossing the broccoli plant of the deposited line or crossing the broccoli plant of the deposited line with another broccoli plant, and optionally gathering (collecting or harvesting) the resulting seed. The method for producing a seed of the present invention may provide a plant, a plant part, or a seed by growing a seed of a broccoli plant.

The method for producing a seed of the present invention may be a method for producing a seed derived from the deposited line. In this case, the method for producing a seed of the present invention may include the step of (a) crossing a plant of the deposited line with another broccoli plant to produce a seed. The method for producing a seed of the present invention may further include the steps of (b) cultivating a broccoli plant from the seed obtained in step (a) to produce a broccoli plant derived from the deposited line, and (c) self-crossing the broccoli plant obtained in step (b) or crossing the broccoli plant obtained in step (b) with another broccoli plant to produce an additional broccoli plant derived from the deposited line. The method for producing a seed of the present invention may further include the step of (d) optionally repeating steps (b) and (c) one or more times to further produce a broccoli plant(s) derived from the deposited line. In this case, as the broccoli plant was cultivated from the seed obtained from step (a) in step (b), an additional broccoli plant that has been obtained in step (c) can be used. The "one or more times" is, for example, one to 10 times, three to seven times, or three to five times. The method for producing a seed of the present invention may further include the step of collecting or harvesting the seed. The method for producing a seed of the present invention may provide a seed produced by the above method and a plant or a part of a plant individual obtained by growing the seed.

<Method for Producing a Hybrid Broccoli Plant>

The present invention provides a method for producing a hybrid broccoli plant. The method for producing a hybrid plant of the present invention includes the step of crossing the broccoli plant of the present invention with another broccoli plant. The method for producing a hybrid plant of the present invention may include the step of collecting or harvesting the seed obtained by crossing. The method for producing a hybrid plant of the present invention may provide a seed produced by the above method and a hybrid plant or a part of a hybrid plant individual.

<Method for Introducing a New Characteristic>

The present invention provides a method for introducing at least one new trait or characteristic (hereinafter, together referred to as a "characteristic") into the deposited line. The method for introducing a characteristic of the present invention can also be referred to as, for example, a method for producing a broccoli plant into which a new characteristic has been introduced. The method for introducing a characteristic of the invention includes the steps of (a) crossing a plant of the deposited line with a broccoli plant having at least one new characteristic to produce a progeny line, and (b) selecting a progeny line having at least one new characteristic, for example. The method for introducing a characteristic of the present invention includes (c) crossing the progeny line with the deposited line to produce a backcross progeny seed(s), and (d) selecting a backcross progeny having at least one new characteristic and having essentially all physiological and morphological characteristics of the deposited line, for example. In steps (b) and (d), selection of a progeny line having a new characteristic may be performed by detecting the characteristic or by detecting a gene or a molecular marker associated (linked) with the characteristic. Examples of the new characteristic include diamondback moth insect resistance, fall armyworm resistance, LSL (stay green, ethylene insensitive), and characteristics of coloring green even under weak light (characteristics of coloring green even in hidden areas).

The method for introducing a characteristic of the present invention may include the step of (e) optionally repeating steps (c) and (d) one or more times to produce a broccoli plant(s) having at least one new characteristic. In this case, in the method for introducing a characteristic of the present invention, a backcross progeny that has been selected in step (d) can be used as the progeny line in step (c). A broccoli plant obtained or obtainable in step (e) may have essentially all physiological and morphological characteristics of the deposited line. Regarding the "essentially all physiological and morphological characteristics," reference can be made to the description as to the progeny line by replacing a "progeny line" with a "broccoli plant obtained or obtainable in step (e)." The "one or more times" is, for example, one to 10 times, three to seven times, or three to five times. The method for introducing a characteristic of the present invention may include the step of collecting or harvesting a seed. The method for introducing a characteristic of the present invention may provide a seed produced by the above method and a plant or a part of a plant individual obtained by growing the seed.

<Method for Transferring a Transgene>

The present invention provides a method for producing a plant derived from a deposited line having at least one new trait or characteristic. The method for transferring a transgene of the present invention can also be referred to as, for example, a method for producing a broccoli plant into which a new characteristic has been introduced.

The method for transferring a transgene of the invention includes the step of transferring a mutation or a transgene that imparts at least one new characteristic into a plant of a deposited line, for example. The transfer of a mutation or a transgene can be performed, for example, in the same manner as the transfer of a mutation or a transgene in the progeny line. A broccoli plant obtained or obtainable by the transferring may have essentially all physiological and morphological characteristics of the deposited line. Regarding the "essentially all physiological and morphological characteristics," reference can be made to the description as to the progeny line by replacing a "progeny line" with a "broccoli plant obtained or obtainable by the transferring." The method for transferring a transgene of the present invention may include the step of collecting or harvesting a seed. The method for transferring a transgene of the present invention may provide a seed produced by the above method and a plant or a part of a plant individual obtained by growing the seed. Examples of the new characteristic include diamondback moth insect resistance, fall armyworm resistance, LSL (stay green, ethylene insensitive), and characteristics of coloring green even under weak light (characteristics of coloring green even in hidden areas).

<Broccoli Plant Regenerated Product and Regeneration Method>

The present invention provides a broccoli plant regenerated from a cell culture, a tissue culture, or a protoplast of a deposited line (hereinafter referred to as a "regenerated product"). The present invention may provide cell cultures or tissue cultures of regeneratable cells or protoplasts derived from broccoli plants of a deposited line. The cells, tissues, or protoplasts may be derived from tissues including leaves, pollens, embryos, cotyledons, hypocotyls, meristematic cells, roots, root tips, anthers, flowers, seeds, or trunks.

The present invention provides a method of growth or propagation of a broccoli plant of a deposited line. The propagation of the broccoli plant of the deposited line may be a vegetative propagation of the broccoli plant of the deposited line. In this case, the method for regenerating a broccoli plant of the present invention includes the steps of (a) collecting a tissue that can be grown from a plant of a deposited line, (b) culturing the tissue to obtain a grown shoot, and (c) rooting the grown shoot to obtain a rooted plantlet, for example. The method for regenerating a broccoli plant of the present invention may further include (d) optionally growing a plant from a rooted plantlet. Regarding the method of vegetative propagation, for example, reference can be made to References 10 and 11 below. The regeneration method of the present invention may provide a plantlet, a plant, or a part of a plant individual regenerated (produced) by the method described above. The plant may have essentially all physiological and morphological characteristics of the deposited line. Regarding the "essentially all physiological and morphological characteristics," reference can be made to the description of the progeny line by replacing a "progeny line" with a "regenerated plant."

Reference 10: Habtamu Gudisa Megersa, *Propagation Methods of Selected Horticultural Crops by Specialized Organs: Review*, Journal of Horticulture, 2017, vol. 4, issue 2, 1000198.

Reference 11: Nitish Kumar et al., *In vitro Plant Propagation: A Review*, Journal of Forest Science, 2011, vol. 27, no. 2, pp. 61-72.

<Harvest and Processed Product of Broccoli Plant>

The present invention provides a harvest and/or a processed product of a deposited line or a progeny line. The harvest is a whole plant or a part of a plant individual, preferably including a flower head or a seed.

When the harvest is a flower head, the harvest may include a peduncle immediately below the flower head, in addition to the flower head. The length of the peduncle to be harvested is, for example, about 1 to 20 cm and about 7 to 15 cm. If the harvest is a flower head, the flower head may be a bundle of a plurality of flower heads.

The processed product includes any product obtained by treating the deposited line or the progeny line. The treatment is not particularly limited, and can be, for example, cutting, slicing, grinding, pureeing, drying, canning, bottling, washing, packaging, freezing and/or heating. In the deposited line or the progeny line, a plant or a part of a plant individual used in the processed product is, for example, a flower head. The processed product may be, for example, a product obtained by washing and packaging the deposited line or the progeny line. The processed product may be contained, for example, in a container of any size or shape. Specific examples of the container include a bag, a box, and a carton. The cut may be, for example, a floret processing of cutting the main flower head into small flower heads.

The present invention may provide a container containing one or more broccoli plants. The container contains a whole plant or a part of a plant individual, preferably a flower head.

The present invention may provide a method for producing a broccoli plant as a food (a method for producing a food). The method for producing a food of the present invention includes the step of collecting or harvesting a whole plant or a part of a plant individual of the deposited line or the progeny line, preferably a flower head of the deposited line or the progeny line, for example. In addition, the method for producing a food of the present invention includes the step of cultivating a broccoli plant of the deposited line or the progeny line until it is matured.

<Method for Determining Genotype>

The present invention provides a method for determining or detecting a genotype of a deposited line or a progeny line. The method for determining a genotype of the invention includes the steps of (a) obtaining a nucleic acid sample from a deposited line or a progeny line, and (b) detecting a genome in the nucleic acid sample, for example. In step (a), the method for preparing a nucleic acid from the deposited line or the progeny line can be performed using a general method for preparing a nucleic acid from a tissue. In step (b), for example, a polymorphism and/or an allele in the genome in the nucleic acid sample is detected. Detection of the polymorphism and/or allele can be performed using, for example, SNP genotyping, AFLP detection, genomic DNA RFLP identification, genomic DNA CAPS detection, genomic DNA random amplified polymorphic detection, polymerase chain reaction, DNA sequences, allele specific oligonucleotide probes, DNA microarrays, and the like. The polymorphism and/or the allele may be detected, for example, by sequencing the base sequence of the genome, or, as described above, by referring to the SNPs of the deposited lines. In step (b), one or two or more polymorphisms and/or alleles in the genomic DNA may be detected. The method for determining a genotype of the present invention may include the step of storing a detection result of a polymorphism and/or an allele in a computer-readable medium. The present invention may provide a computer-readable medium produced by such a method.

The method for determining a genotype of the present invention may be performed on any broccoli plant (target broccoli plant) in place of the deposited line or the progeny line, for example. In this case, the method for determining a genotype of the present invention may further include the step of determining whether the target broccoli plant is the progeny line on the basis of the result of step (b), for example. The determination can also be said to be, for example, discrimination, estimation, appraisal, or distinguishability. The determination can be made based on, for example, a concordance rate between the result of step (b) and the genotype of the deposited line.

EXAMPLES

The present invention will be described specifically below with reference to examples.

It is to be noted, however, that the present invention is by no means limited to embodiments described in the following examples.

Example 1

Broccoli plants of the deposited line were bred to examine their traits and characteristics and to examine polymorphisms possessed by the deposited line.

(1) Breeding of Deposited Line

In 2007, a broccoli line of stable cultivation with many leaves (made by TAKII & CO., LTD) was crossed with a broccoli line with relatively vigorous growth in a low-temperature period and no anthocyanin coloration (made by TAKII & CO., LTD) to obtain F1 generation. In 2008, the F1 generation was self-crossed to obtain F2 generation. The obtained F2 generation was selected by focusing attention on the stability of growth, the shape of the flower head, the color of the flower head, and the like, and the selected F2 generation was self-crossed. After that, selection and self-crossing were repeated in the same manner, thereby obtaining F7 generation. Since it was determined that the target characteristic was fixed, breeding was terminated at the F7 generation in 2013.

One hundred strains of F7 were seeded on Aug. 2, 2013 at the testing laboratory (Sato, Okubo-cho, Tahara-shi, Aichi Prefecture), and then cultivated to examine that there was no variation in characteristics in F7 and that the bred broccoli variety had uniformity and stability. Then the F7 generation was self-crossed, and the seed of the F8 generation was deposited, disclosed herein, and recited in the claims, under the Budapest Treaty and accepted by the International Patent Organism Depositary Authority, #120, 2-5-8, Kazusakama-tari, Kisarazu-shi, Chiba 292-0818, Japan, as Accession No. FERM BP-22393. The date of deposit was Jul. 30, 2022. Upon issuance of a patent, all restrictions upon the deposit will be removed, and the deposit is intended to meet all of the requirements of 37 C.F.R. § 1.801-1.809. The accession number for those deposited seeds of broccoli cv. Takii 12 is Accession No. FERM BP-22393. The deposit will be maintained in the depository for a period of 30 years, or 5 years after the last request, or for the effective life of the patent, whichever is longer, and will be replaced, if necessary, during that period.

(2) Characteristics of Deposited Line

Figure 6A:
FIGS. 6A and 6B are photographs showing the deposited lines at the time of harvest.
Figure 6B:
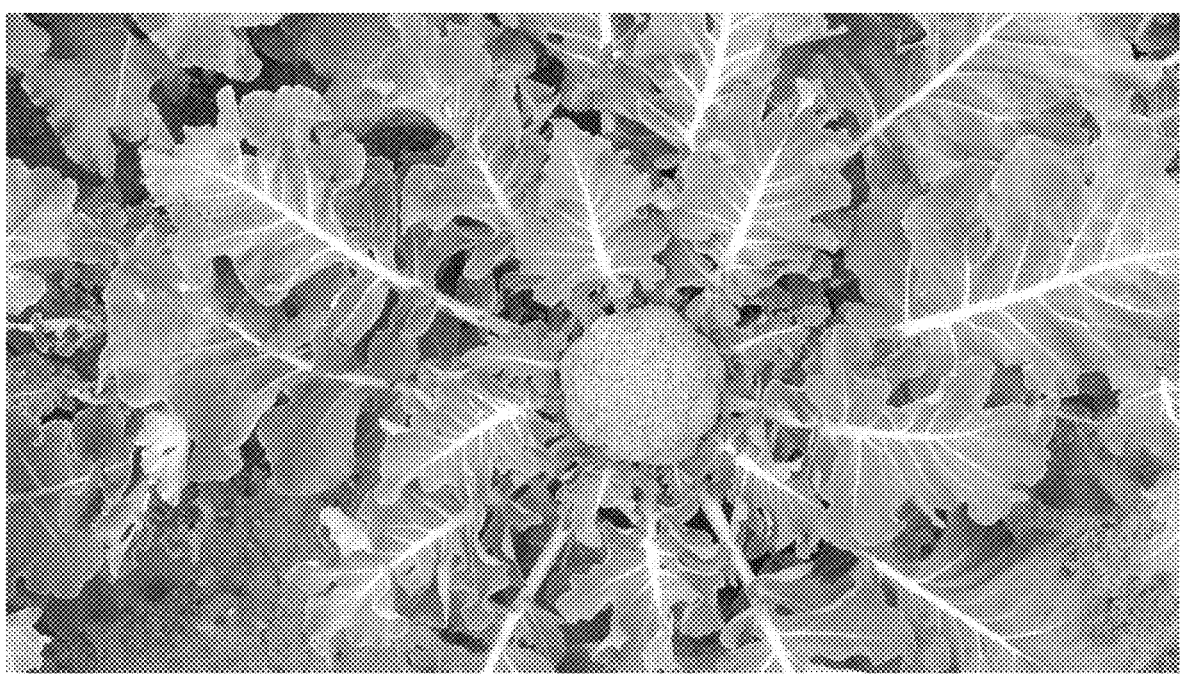

The traits and characteristics of F7 plant individuals were evaluated according to the Broccoli Variant Test Guideline published by the MAFF. The traits and characteristics of F7 plant individuals were also evaluated based on the criteria for Characteristic Nos. 40 to 42. The results are shown in Tables 3A through 3C below. It has been verified that the deposited lines also exhibit the same characteristics. Photographs of the F7 line at the time of harvest are shown in FIGS. 6A and 6B. FIG. 6A is a photograph showing the whole view of the cultivation area of F7, and FIG. 6B is a photograph showing the whole plant of F7.

TABLE 3A

| Characteristic No. | Characteristics | Measurement Method | Note | Deposited Line |
|---|---|---|---|---|
| 1 | Plant: number of stems | Observation | 1: one, 2: more than one | 1 |
| 2 | Plant: height | Measurement (cm) | 3: short, 5: medium, 7: tall | 5 (45 cm) |
| 3 | Leaf: attitude | Observation | 3: semi-erect, 5: horizontal, 7: semi-pendulous | 3 |
| 4 | Leaf: length | Measurement (cm) | 3: short, 5: medium, 7: long | 5 (48 cm) |
| 5 | Leaf: width | Measurement (cm) | 3: narrow, 5: medium, 7: broad | 5 (19 cm) |
| 6 | Leaf: number of lobes | Observation | 3: few, 5: medium, 7: many | 7 |
| 7 | Leaf blade: color | Observation | 1: green, 2: gray-green, 3: blue-green | 2 |
| 8 | Leaf blade: intensity of color | Observation | 3: light, 5: medium, 7: dark | 5 |
| 9 | Leaf blade: anthocyanin coloration | Observation | 1: absent, 9: present | 1 |
| 10 | Leaf blade: undulation of margin | Observation | 3: weak, 5: medium, 7: strong | 5 |
| 11 | Leaf blade: dentation of margin | Observation | 3: weak, 5: medium, 7: strong | 3 |
| 12 | Leaf blade: blistering | Observation | 3: weak, 5: medium, 7: strong | 3 |
| 13 | Petiole: anthocyanin coloration | Observation | 1: absent, 9: present | 1 |
| 14 | Petiole: length | Observation | 3: short, 5: medium, 7: long | 5 |
| 15 | Head: length of branching | Measurement (cm) | 3: short, 5: medium, 7: long | 3 (3 cm) |
| 16 | Head: size | Measurement (cm × cm) | 3: small, 5: medium, 7: large | 5 (10.5 cm × 13 cm) |
| 17 | Head: weight | Measurement (g) | 3: light, 5: medium, 7: heavy | 7 (440 g) |
| 18 | Head: shape in longitudinal section | Observation | 1: circular, 2: transverse broad elliptic, 3: transverse medium elliptic, 4: transverse narrow elliptic, 5: triangular | 2 |

TABLE 3B

| Characteristic No. | Characteristics | Measurement Method | Note | Deposited Line |
|---|---|---|---|---|
| 19 | Head: color | Observation | 1: cream, 2: green, 3: gray-green, 4: blue-green, 5: violet | 2 |
| 20 | Head: intensity of color | Observation | 3: light, 5: medium, 7: dark | 5 |
| 21 | Head: anthocyanin coloration | Observation | 1: absent, 9: present | 9 |
| 22 | Head: intensity of anthocyanin coloration | Observation | 3: weak, 5: medium, 7: strong | 3 |
| 23 | Head: knobbling | Observation | 3: fine, 5: medium, 7: coarse | 3 |
| 24 | Head: texture | Observation | 3: fine, 5: medium, 7: coarse | 5 |
| 25 | Head: firmness | Observation | 3: loose, 5: medium, 7: firm | 7 |

TABLE 3B-continued

| Characteristic No. | Characteristics | Measurement Method | Note | Deposited Line |
|---|---|---|---|---|
| 26 | Head: conspicuousness of spiral pattern | Observation | 1: obscure, 2: obvious | 1 |
| 27 | Head: bracts | Observation | 1: absent, 9: present | 1 |
| 28 | Peduncle: length | Measurement (cm) | 3: short, 5: medium, 7: long | 3 (2.5 cm) |
| 29 | Peduncle: thickness | Measurement (mm) | 3: thin, 5: medium, 7: thick | 7 (42 mm) |
| 30 | Peduncle: hardness | Observation | 3: soft, 5: medium, 7: hard | 5 |
| 31 | Peduncle: color | Observation | 1: white, 2: light green, 3: green, 4: tinged with purple | 3 |
| 32 | Plant: secondary heads | Observation | 1: absent, 9: present | 1 |
| 34 | Flower: color | Observation | 1: white, 2: yellow | 2 |
| 35 | Flower: intensity of yellow color | Observation | 3: light, 5: medium, 7: dark | 5 |
| 36 | Time of harvest | Measurement (date) | 3: early, 5: medium, 7: late | 7 (December 13) |
| 37 | Time of beginning of flowering | Measurement (date) | 3: early, 5: medium, 7: late | 5 (March 10) |
| 38 | Male sterility | Observation | 1: absent, 9: present | 1 |

TABLE 3C

| Characteristic No. | Characteristics | Measurement Method | Note | Deposited Line |
|---|---|---|---|---|
| 40 | Leaf: number | Observation | 1: few, 9: many | 9 |
| 41 | Stem: length | Observation | 1: short, 9: long | 1 |
| 42 | Leaf: depth of lobes | Observation | 1: shallow, 9: deep | 9 |

(3) SNP Marker of Deposited Line

The SNPs described in Tables 2A through 2U were analyzed for the deposited lines and the commercial broccoli varieties described below. The results are shown in Tables 4A through 4G below. As shown in Tables 4A through 4G below, it was found that SNP7, SNP8, SNP20, SNP21, SNP75, SNP78, SNP81, SNP84, SNP90, SNP142, SNP165, and SNP177 are deposited line-specific SNPs and that the progeny line can be identified by combining one or more of these SNPs. It was verified that F7 has the same SNPs. In addition, in Tables 4A through 4G, A represents a homozygous type of SNP A, H represents a heterozygous type of SNP A and SNP B, B represents a homozygous type of SNP B, chr represents a chromosome number, and cM represents centimorgan.

(Products of TAKII & CO., LTD)
SHASTA, ERUDE, HAITSU SP, FOREST, TBR-449, CASTLE, GREEN FACE, MEGADOME
(Products of SAKATA SEED CORPORATION)
PIXEL, SK9-099, GREEN CANNON, GRANDOME, HEARTLAND, DESTINY, Gypsy,
Emerald Crown, Marathon, Avenger, Imperial (Products of Brolead Co., Ltd.)
SUBARU, FIGHTER
(Product of Nacos)
SHIKIMIDORI 96
(Product of MIKADO KYOWA SEED CO. LTD.)
SPEED DOME 052
(Product of Seminis, Inc.)
IRONMAN

TABLE 4A

| SNP ID | Chr | cM | Location of SNPs on chromosomes | A | B | Deposited line | Deposited line | Deposited line | Deposited line | Deposited line | Deposited line |
|---|---|---|---|---|---|---|---|---|---|---|---|
| SNP1 | 1 | 0.990 | 454335 | G | T | A | A | A | A | A | A |
| SNP2 | 1 | 6.422 | 1264234 | G | C | B | B | B | B | B | B |
| SNP3 | 1 | 9.780 | 1783522 | C | T | B | B | B | B | B | B |
| SNP4 | 1 | 24.743 | 4314082 | T | G | A | A | A | A | A | A |
| SNP5 | 1 | 36.521 | 7889954 | A | C | A | A | A | A | A | A |
| SNP6 | 1 | 39.178 | 8784702 | T | C | B | B | B | B | B | B |
| SNP7 | 1 | 40.958 | 9420949 | C | T | A | A | A | A | A | A |
| SNP8 | 1 | 46.689 | 11980318 | A | G | A | A | A | A | A | A |
| SNP9 | 1 | 52.193 | 13607081 | G | C | B | B | B | B | B | B |
| SNP10 | 1 | 52.272 | 13635739 | C | G | B | B | B | B | B | B |
| SNP11 | 1 | 56.649 | 17705704 | A | G | B | B | B | B | B | B |
| SNP12 | 1 | 58.660 | 22288471 | G | T | A | A | A | A | A | A |
| SNP13 | 1 | 75.912 | 41231290 | T | C | B | B | B | B | B | B |
| SNP14 | 1 | 77.423 | 41526625 | C | A | A | A | A | A | A | A |
| SNP15 | 1 | 82.329 | 42118296 | G | T | A | A | A | A | A | A |
| SNP16 | 1 | 87.796 | 42587881 | C | G | B | B | B | B | B | B |
| SNP17 | 1 | 88.361 | 42631525 | C | T | A | A | A | A | A | A |
| SNP18 | 1 | 88.361 | 42631552 | A | G | A | A | A | A | A | A |
| SNP19 | 1 | 95.612 | 43132615 | T | A | B | B | B | B | B | B |
| SNP20 | 2 | 3.410 | 717479 | T | A | A | A | A | A | A | A |
| SNP21 | 2 | 3.410 | 717482 | T | A | A | A | A | A | A | A |
| SNP22 | 2 | 8.829 | 1481256 | A | T | B | B | B | B | B | B |
| SNP23 | 2 | 32.758 | 3792354 | G | A | B | B | B | B | B | B |
| SNP24 | 2 | 49.203 | 8267341 | A | G | A | A | A | A | A | A |
| SNP25 | 2 | 49.415 | 8420520 | A | C | B | B | B | B | B | B |
| SNP26 | 2 | 49.704 | 8638214 | T | C | A | A | A | A | A | A |
| SNP27 | 2 | 51.821 | 11081737 | G | A | A | A | A | A | A | A |

TABLE 4A-continued

| SNP ID | Chr | cM | Location of SNPs on chromosomes | Deposited line | SHASTA | ERUDE | HAITSU SP | FOREST | TBR-449 | CASTLE | GREEN FACE |
|---|---|---|---|---|---|---|---|---|---|---|---|
| SNP28 | 2 | 55.999 | 27333228 | G | A | A | A | A | A | A | A |
| SNP29 | 2 | 62.589 | 45424768 | A | G | A | A | A | A | A | A |
| SNP1 | 1 | 0.990 | 454335 | A | B | H | H | H | H | B | H |
| SNP2 | 1 | 6.422 | 1264234 | B | B | B | B | B | B | B | B |
| SNP3 | 1 | 9.780 | 1783522 | B | B | B | B | B | B | B | H |
| SNP4 | 1 | 24.743 | 4314082 | A | A | A | H | B | H | B | A |
| SNP5 | 1 | 36.521 | 7889954 | A | B | B | B | B | B | H | B |
| SNP6 | 1 | 39.178 | 8784702 | B | B | H | B | B | B | B | B |
| SNP7 | 1 | 40.958 | 9420949 | A | B | H | B | B | B | H | B |
| SNP8 | 1 | 46.689 | 11980318 | A | H | H | H | B | B | B | B |
| SNP9 | 1 | 52.193 | 13607081 | B | H | H | A | A | B | H | A |
| SNP10 | 1 | 52.272 | 13635739 | B | A | A | A | A | B | A | A |
| SNP11 | 1 | 56.649 | 17705704 | B | H | B | H | A | B | A | A |
| SNP12 | 1 | 58.660 | 22288471 | A | H | A | H | H | B | H | B |
| SNP13 | 1 | 75.912 | 41231290 | B | H | H | A | H | H | H | H |
| SNP14 | 1 | 77.423 | 41526625 | A | A | A | A | H | A | B | A |
| SNP15 | 1 | 82.329 | 42118296 | A | A | A | A | A | H | H | H |
| SNP16 | 1 | 87.796 | 42587881 | B | H | H | A | H | B | H | A |
| SNP17 | 1 | 88.361 | 42631525 | A | H | B | H | H | B | B | H |
| SNP18 | 1 | 88.361 | 42631552 | A | H | B | H | H | B | B | H |
| SNP19 | 1 | 95.612 | 43132615 | B | H | A | H | H | H | A | H |
| SNP20 | 2 | 3.410 | 717479 | A | B | H | H | H | B | B | H |
| SNP21 | 2 | 3.410 | 717482 | A | B | H | H | H | B | B | H |
| SNP22 | 2 | 8.829 | 1481256 | B | B | B | B | B | B | B | B |
| SNP23 | 2 | 32.758 | 3792354 | B | H | B | B | H | B | H | H |
| SNP24 | 2 | 49.203 | 8267341 | A | B | B | B | B | B | B | B |
| SNP25 | 2 | 49.415 | 8420520 | B | B | B | B | B | B | B | H |
| SNP26 | 2 | 49.704 | 8638214 | A | B | B | B | B | B | H | H |
| SNP27 | 2 | 51.821 | 11081737 | A | B | B | B | B | H | H | B |
| SNP28 | 2 | 55.999 | 27333228 | A | A | H | H | A | H | A | A |
| SNP29 | 2 | 62.589 | 45424768 | A | A | H | H | A | B | A | A |

| SNP ID | Chr | cM | Location of SNPs on chromosomes | MEGA-DOME | PIXEL | SK9-099 | GREEN CANNON | GRAN-DOME | HEART-LAND | DES-TINY | Gypsy |
|---|---|---|---|---|---|---|---|---|---|---|---|
| SNP1 | 1 | 0.990 | 454335 | B | H | A | A | A | B | H | A |
| SNP2 | 1 | 6.422 | 1264234 | H | H | B | B | B | B | H | B |
| SNP3 | 1 | 9.780 | 1783522 | B | B | B | B | B | B | B | B |
| SNP4 | 1 | 24.743 | 4314082 | H | A | B | B | A | B | A | A |
| SNP5 | 1 | 36.521 | 7889954 | H | H | B | H | H | B | H | H |
| SNP6 | 1 | 39.178 | 8784702 | B | B | B | H | B | B | H | B |
| SNP7 | 1 | 40.958 | 9420949 | B | H | B | B | B | B | B | B |
| SNP8 | 1 | 46.689 | 11980318 | H | H | B | B | B | B | H | H |
| SNP9 | 1 | 52.193 | 13607081 | H | H | H | H | H | A | A | B |
| SNP10 | 1 | 52.272 | 13635739 | A | H | H | H | H | A | A | H |
| SNP11 | 1 | 56.649 | 17705704 | H | B | H | B | H | A | H | H |
| SNP12 | 1 | 58.660 | 22288471 | H | H | H | B | H | A | A | H |
| SNP13 | 1 | 75.912 | 41231290 | A | A | B | H | B | B | H | H |
| SNP14 | 1 | 77.423 | 41526625 | B | H | A | A | A | B | B | A |
| SNP15 | 1 | 82.329 | 42118296 | H | H | B | A | H | A | H | H |
| SNP16 | 1 | 87.796 | 42587881 | A | A | H | A | H | B | A | H |
| SNP17 | 1 | 88.361 | 42631525 | B | H | H | H | H | B | A | B |
| SNP18 | 1 | 88.361 | 42631552 | B | H | H | H | H | B | A | B |
| SNP19 | 1 | 95.612 | 43132615 | A | B | B | H | B | A | B | H |
| SNP20 | 2 | 3.410 | 717479 | B | B | B | B | H | B | H | H |
| SNP21 | 2 | 3.410 | 717482 | B | B | B | B | H | B | H | H |
| SNP22 | 2 | 8.829 | 1481256 | B | B | B | B | B | B | B | B |
| SNP23 | 2 | 32.758 | 3792354 | H | H | H | B | B | A | H | B |
| SNP24 | 2 | 49.203 | 8267341 | H | H | A | B | B | B | H | B |
| SNP25 | 2 | 49.415 | 8420520 | B | B | B | H | B | B | H | H |
| SNP26 | 2 | 49.704 | 8638214 | H | H | H | H | H | B | A | H |
| SNP27 | 2 | 51.821 | 11081737 | H | H | H | H | H | B | A | H |
| SNP28 | 2 | 55.999 | 27333228 | A | H | A | A | H | A | A | H |
| SNP29 | 2 | 62.589 | 45424768 | A | H | A | H | A | A | A | H |

| SNP ID | Chr | cM | Location of SNPs on chromosomes | Emerald Crown | Marathon | Avenger | Imperial | SUBARU | FIGHTER | SHIK-IMIDORI 96 | SPEED DOME 052 | IRON-MAN |
|---|---|---|---|---|---|---|---|---|---|---|---|---|
| SNP1 | 1 | 0.990 | 454335 | H | A | A | H | H | H | B | H | H |
| SNP2 | 1 | 6.422 | 1264234 | H | B | B | B | H | B | B | H | B |

TABLE 4A-continued

| SNP | Chr | cM | | | | | | | | | | |
|---|---|---|---|---|---|---|---|---|---|---|---|---|
| SNP3 | 1 | 9.780 | 1783522 | B | B | B | B | B | B | B | B | B |
| SNP4 | 1 | 24.743 | 4314082 | H | H | H | B | A | A | B | A | H |
| SNP5 | 1 | 36.521 | 7889954 | B | H | H | B | H | B | B | H | A |
| SNP6 | 1 | 39.178 | 8784702 | B | H | H | H | H | B | B | H | H |
| SNP7 | 1 | 40.958 | 9420949 | B | B | B | B | B | B | B | B | B |
| SNP8 | 1 | 46.689 | 11980318 | H | B | B | H | H | H | H | H | B |
| SNP9 | 1 | 52.193 | 13607081 | H | H | H | H | A | H | A | H | H |
| SNP10 | 1 | 52.272 | 13635739 | H | H | H | H | A | H | A | H | H |
| SNP11 | 1 | 56.649 | 17705704 | B | H | H | H | H | B | H | H | H |
| SNP12 | 1 | 58.660 | 22288471 | H | H | H | H | A | H | H | A | H |
| SNP13 | 1 | 75.912 | 41231290 | H | H | B | H | H | H | H | H | A |
| SNP14 | 1 | 77.423 | 41526625 | H | A | A | A | H | H | B | H | A |
| SNP15 | 1 | 82.329 | 42118296 | B | A | H | H | H | B | H | A | H |
| SNP16 | 1 | 87.796 | 42587881 | H | A | H | H | A | H | H | A | H |
| SNP17 | 1 | 88.361 | 42631525 | A | H | H | H | A | B | B | H | H |
| SNP18 | 1 | 88.361 | 42631552 | A | H | H | H | A | B | B | H | H |
| SNP19 | 1 | 95.612 | 43132615 | B | B | B | B | B | H | H | B | B |
| SNP20 | 2 | 3.410 | 717479 | B | H | H | B | H | B | B | H | B |
| SNP21 | 2 | 3.410 | 717482 | B | H | H | B | H | B | B | H | B |
| SNP22 | 2 | 8.829 | 1481256 | B | B | B | B | B | B | B | H | H |
| SNP23 | 2 | 32.758 | 3792354 | H | B | B | H | H | H | A | H | B |
| SNP24 | 2 | 49.203 | 8267341 | B | B | B | B | H | B | H | H | B |
| SNP25 | 2 | 49.415 | 8420520 | B | H | H | H | H | B | B | B | H |
| SNP26 | 2 | 49.704 | 8638214 | H | H | H | H | A | B | H | H | H |
| SNP27 | 2 | 51.821 | 11081737 | H | H | H | H | A | B | H | H | H |
| SNP28 | 2 | 55.999 | 27333228 | A | H | A | H | A | A | A | A | B |
| SNP29 | 2 | 62.589 | 45424768 | H | H | H | H | A | H | A | A | H |

TABLE 4B

| SNP ID | Chr | cM | Location of SNPs on chromosomes | A | B | De-posited line | De-posited line | De-posited line | De-posited line | De-posited line | Deposited line |
|---|---|---|---|---|---|---|---|---|---|---|---|
| SNP30 | 2 | 64.493 | 46653493 | A | T | B | B | B | B | B | B |
| SNP31 | 2 | 74.571 | 49757428 | A | G | A | A | A | A | A | A |
| SNP32 | 2 | 77.901 | 50407246 | G | A | B | B | B | B | B | B |
| SNP33 | 2 | 83.240 | 51346970 | C | T | A | A | A | A | A | A |
| SNP34 | 2 | 83.240 | 51347002 | T | G | B | B | B | B | B | B |
| SNP35 | 2 | 84.263 | 51516676 | A | G | B | B | B | B | B | B |
| SNP36 | 2 | 84.263 | 51516714 | T | G | B | B | B | B | B | B |
| SNP37 | 2 | 86.232 | 51834225 | A | G | A | A | A | A | A | A |
| SNP38 | 2 | 86.232 | 51834270 | C | T | A | A | A | A | A | A |
| SNP39 | 3 | 1.187 | 675632 | A | C | B | B | B | B | B | B |
| SNP40 | 3 | 2.498 | 948354 | T | C | B | B | B | B | B | B |
| SNP41 | 3 | 5.739 | 1516935 | G | A | B | B | B | B | B | B |
| SNP42 | 3 | 5.739 | 1516977 | A | T | B | B | B | B | B | B |
| SNP43 | 3 | 20.656 | 3369359 | A | G | A | A | A | A | A | A |
| SNP44 | 3 | 21.013 | 3409356 | T | G | B | B | B | B | B | B |
| SNP45 | 3 | 28.303 | 4315752 | T | G | A | A | A | A | A | A |
| SNP46 | 3 | 38.853 | 5932635 | G | A | A | A | A | A | A | A |
| SNP47 | 3 | 48.248 | 8135062 | T | G | B | B | B | B | B | B |
| SNP48 | 3 | 49.393 | 8510724 | C | T | A | A | A | A | A | A |
| SNP49 | 3 | 54.259 | 10912440 | T | G | B | B | B | B | B | B |
| SNP50 | 3 | 56.441 | 12711867 | C | A | B | B | B | B | B | B |
| SNP51 | 3 | 59.622 | 14684781 | A | T | B | B | B | B | B | B |
| SNP52 | 3 | 68.614 | 20818643 | T | C | B | B | B | B | B | B |
| SNP53 | 3 | 71.069 | 22019198 | A | G | B | B | B | B | B | B |
| SNP54 | 3 | 75.613 | 23508195 | T | G | A | A | A | A | A | A |
| SNP55 | 3 | 76.384 | 23746683 | C | T | B | B | B | B | B | B |
| SNP56 | 3 | 76.582 | 23809957 | T | C | A | A | A | A | A | A |
| SNP57 | 3 | 79.755 | 24764254 | T | G | A | A | A | A | A | A |
| SNP58 | 3 | 80.244 | 24921510 | T | C | A | A | A | A | A | A |
| SNP59 | 3 | 83.407 | 26569816 | A | C | B | B | B | B | B | B |

| SNP ID | Chr | cM | Location of SNPs on chromosomes | De-posited line | SHAS-TA | ERUDE | HAITSU SP | FOREST | TBR-449 | CASTLE | GREEN FACE |
|---|---|---|---|---|---|---|---|---|---|---|---|
| SNP30 | 2 | 64.493 | 46653493 | B | H | H | H | B | A | B | B |
| SNP31 | 2 | 74.571 | 49757428 | A | A | A | H | B | H | A | A |
| SNP32 | 2 | 77.901 | 50407246 | B | A | H | A | B | A | H | H |
| SNP33 | 2 | 83.240 | 51346970 | A | A | A | A | A | H | A | A |
| SNP34 | 2 | 83.240 | 51347002 | B | B | H | H | B | B | B | B |
| SNP35 | 2 | 84.263 | 51516676 | B | H | H | H | H | B | H | B |

TABLE 4B-continued

| SNP ID | Chr | cM | Location of SNPs on chromosomes | | | | | | | | |
|---|---|---|---|---|---|---|---|---|---|---|---|
| SNP36 | 2 | 84.263 | 51516714 | B | H | H | H | H | B | H | B |
| SNP37 | 2 | 86.232 | 51834225 | A | A | A | A | A | H | A | A |
| SNP38 | 2 | 86.232 | 51834270 | A | A | A | A | A | H | A | A |
| SNP39 | 3 | 1.187 | 675632 | B | A | B | H | H | A | H | B |
| SNP40 | 3 | 2.498 | 948354 | B | B | B | B | B | B | B | B |
| SNP41 | 3 | 5.739 | 1516935 | B | H | B | B | B | A | B | B |
| SNP42 | 3 | 5.739 | 1516977 | B | H | B | B | B | A | B | B |
| SNP43 | 3 | 20.656 | 3369359 | A | A | A | H | H | H | A | H |
| SNP44 | 3 | 21.013 | 3409356 | B | H | B | B | B | H | B | B |
| SNP45 | 3 | 28.303 | 4315752 | A | A | H | A | A | A | A | A |
| SNP46 | 3 | 38.853 | 5932635 | A | A | A | A | A | H | A | A |
| SNP47 | 3 | 48.248 | 8135062 | B | H | H | A | A | A | B | H |
| SNP48 | 3 | 49.393 | 8510724 | A | A | H | H | A | H | H | A |
| SNP49 | 3 | 54.259 | 10912440 | B | A | B | B | B | B | H | B |
| SNP50 | 3 | 56.441 | 12711867 | B | B | B | B | B | B | B | H |
| SNP51 | 3 | 59.622 | 14684781 | B | H | H | H | B | H | H | B |
| SNP52 | 3 | 68.614 | 20818643 | B | H | H | A | A | H | A | B |
| SNP53 | 3 | 71.069 | 22019198 | B | B | B | H | A | H | H | B |
| SNP54 | 3 | 75.613 | 23508195 | A | A | A | A | H | A | B | A |
| SNP55 | 3 | 76.384 | 23746683 | B | H | H | A | A | B | A | H |
| SNP56 | 3 | 76.582 | 23809957 | A | B | H | B | B | B | B | H |
| SNP57 | 3 | 79.755 | 24764254 | A | A | H | B | B | H | H | A |
| SNP58 | 3 | 80.244 | 24921510 | A | H | H | B | B | H | H | A |
| SNP59 | 3 | 83.407 | 26569816 | B | B | B | B | B | H | B | B |

| SNP ID | Chr | cM | Location of SNPs on chromosomes | MEGA-DOME | PIXEL | SK9-099 | GREEN CANNON | GRAN-DOME | HEART-LAND | DES-TINY | Gypsy |
|---|---|---|---|---|---|---|---|---|---|---|---|
| SNP30 | 2 | 64.493 | 46653493 | B | A | H | B | H | B | B | B |
| SNP31 | 2 | 74.571 | 49757428 | A | H | H | H | H | A | A | H |
| SNP32 | 2 | 77.901 | 50407246 | H | A | H | H | A | A | A | A |
| SNP33 | 2 | 83.240 | 51346970 | A | H | H | H | H | A | A | B |
| SNP34 | 2 | 83.240 | 51347002 | B | H | H | B | H | B | B | A |
| SNP35 | 2 | 84.263 | 51516676 | B | H | H | B | B | A | H | B |
| SNP36 | 2 | 84.263 | 51516714 | B | H | H | B | B | A | H | B |
| SNP37 | 2 | 86.232 | 51834225 | H | H | H | H | H | A | A | B |
| SNP38 | 2 | 86.232 | 51834270 | H | H | H | H | H | A | A | B |
| SNP39 | 3 | 1.187 | 675632 | A | A | H | H | H | B | H | A |
| SNP40 | 3 | 2.498 | 948354 | H | B | B | B | B | B | B | H |
| SNP41 | 3 | 5.739 | 1516935 | B | H | H | H | H | B | B | H |
| SNP42 | 3 | 5.739 | 1516977 | B | H | H | H | H | B | B | H |
| SNP43 | 3 | 20.656 | 3369359 | A | H | H | H | H | A | A | H |
| SNP44 | 3 | 21.013 | 3409356 | B | A | H | H | H | B | B | A |
| SNP45 | 3 | 28.303 | 4315752 | A | A | A | A | A | A | A | A |
| SNP46 | 3 | 38.853 | 5932635 | A | H | B | B | H | A | A | B |
| SNP47 | 3 | 48.248 | 8135062 | B | H | A | A | H | H | B | A |
| SNP48 | 3 | 49.393 | 8510724 | B | H | H | B | H | A | A | H |
| SNP49 | 3 | 54.259 | 10912440 | H | B | B | B | B | B | B | B |
| SNP50 | 3 | 56.441 | 12711867 | B | B | B | B | B | B | B | B |
| SNP51 | 3 | 59.622 | 14684781 | H | B | B | B | B | B | B | B |
| SNP52 | 3 | 68.614 | 20818643 | H | H | H | H | H | A | B | A |
| SNP53 | 3 | 71.069 | 22019198 | H | B | B | B | B | A | B | H |
| SNP54 | 3 | 75.613 | 23508195 | B | H | A | A | A | B | H | A |
| SNP55 | 3 | 76.384 | 23746683 | A | H | A | B | H | A | H | H |
| SNP56 | 3 | 76.582 | 23809957 | B | B | H | H | A | B | H | B |
| SNP57 | 3 | 79.755 | 24764254 | H | B | H | H | A | B | H | B |
| SNP58 | 3 | 80.244 | 24921510 | H | B | H | H | A | B | H | B |
| SNP59 | 3 | 83.407 | 26569816 | H | H | H | H | H | B | B | H |

| SNP ID | Chr | cM | Location of SNPs on chromosomes | Emerald Crown | Marathon | Avenger | Imperial | SUBARU | FIGHT-ER | SHIK-IMIDORI 96 | SPEED DOME 052 | IRON-MAN |
|---|---|---|---|---|---|---|---|---|---|---|---|---|
| SNP30 | 2 | 64.493 | 46653493 | A | H | H | A | B | H | B | B | H |
| SNP31 | 2 | 74.571 | 49757428 | H | H | H | H | A | H | A | A | H |
| SNP32 | 2 | 77.901 | 50407246 | A | H | H | A | A | A | H | H | A |
| SNP33 | 2 | 83.240 | 51346970 | H | H | H | H | A | H | A | A | B |
| SNP34 | 2 | 83.240 | 51347002 | H | H | H | H | B | H | B | B | A |
| SNP35 | 2 | 84.263 | 51516676 | H | B | B | H | H | B | H | H | B |
| SNP36 | 2 | 84.263 | 51516714 | H | B | B | H | H | B | H | H | B |
| SNP37 | 2 | 86.232 | 51834225 | H | H | H | B | A | H | A | A | H |
| SNP38 | 2 | 86.232 | 51834270 | H | H | H | B | A | H | A | A | H |
| SNP39 | 3 | 1.187 | 675632 | A | H | H | H | H | A | A | H | H |
| SNP40 | 3 | 2.498 | 948354 | B | B | B | B | B | H | H | B | H |
| SNP41 | 3 | 5.739 | 1516935 | H | H | H | H | B | H | B | B | H |
| SNP42 | 3 | 5.739 | 1516977 | H | H | H | H | B | H | B | B | H |
| SNP43 | 3 | 20.656 | 3369359 | H | H | H | H | A | H | A | A | A |

TABLE 4B-continued

| SNP44 | 3 | 21.013 | 3409356  | A | A | H | H | B | H | B | B | H |
| SNP45 | 3 | 28.303 | 4315752  | A | A | A | A | A | A | A | A | A |
| SNP46 | 3 | 38.853 | 5932635  | H | H | H | H | A | H | A | A | A |
| SNP47 | 3 | 48.248 | 8135062  | H | H | H | A | B | H | B | B | B |
| SNP48 | 3 | 49.393 | 8510724  | H | H | H | H | A | B | A | A | H |
| SNP49 | 3 | 54.259 | 10912440 | B | B | B | B | B | B | B | B | B |
| SNP50 | 3 | 56.441 | 12711867 | B | B | B | B | B | B | B | B | B |
| SNP51 | 3 | 59.622 | 14684781 | B | B | B | B | B | B | B | B | B |
| SNP52 | 3 | 68.614 | 20818643 | B | H | H | H | B | H | H | B | B |
| SNP53 | 3 | 71.069 | 22019198 | B | H | B | B | B | H | H | B | B |
| SNP54 | 3 | 75.613 | 23508195 | H | A | A | H | H | H | B | H | A |
| SNP55 | 3 | 76.384 | 23746683 | A | B | H | A | H | H | A | A | B |
| SNP56 | 3 | 76.582 | 23809957 | H | H | A | H | H | B | B | H | H |
| SNP57 | 3 | 79.755 | 24764254 | H | H | A | H | H | B | B | H | A |
| SNP58 | 3 | 80.244 | 24921510 | A | H | A | H | H | B | H | H | A |
| SNP59 | 3 | 83.407 | 26569816 | H | H | H | H | B | A | H | B | B |

TABLE 4C

| SNP ID | Chr | cM | Location of SNPs on chromosomes | A | B | Deposited line | Deposited line | Deposited line | Deposited line | Deposited line | Deposited line |
|---|---|---|---|---|---|---|---|---|---|---|---|
| SNP60 | 3 | 92.321  | 45636043 | C | T | A | A | A | A | A | A |
| SNP61 | 3 | 93.347  | 47819830 | G | A | A | A | A | A | A | A |
| SNP62 | 3 | 93.945  | 48535735 | T | C | B | B | B | B | B | B |
| SNP63 | 3 | 98.958  | 52628849 | T | C | B | B | B | B | B | B |
| SNP64 | 3 | 99.714  | 53167534 | T | C | B | B | B | B | B | B |
| SNP65 | 3 | 109.268 | 58494494 | T | G | A | A | A | A | A | A |
| SNP66 | 3 | 109.415 | 58569947 | C | A | A | A | A | A | A | A |
| SNP67 | 3 | 113.736 | 58628362 | C | T | B | B | B | B | B | B |
| SNP68 | 3 | 117.120 | 60116952 | C | G | B | B | B | B | B | B |
| SNP69 | 3 | 121.679 | 61115979 | A | G | B | B | B | B | B | B |
| SNP70 | 3 | 125.279 | 62286307 | C | T | B | B | B | B | B | B |
| SNP71 | 3 | 131.139 | 63119854 | G | A | B | B | B | B | B | B |
| SNP72 | 3 | 131.253 | 64347040 | C | T | B | B | B | B | B | B |
| SNP73 | 3 | 11.174  | 64369480 | G | A | A | A | A | A | A | A |
| SNP74 | 4 | 109.268 | 1826660  | C | T | A | A | A | A | A | A |
| SNP75 | 4 | 14.947  | 2437167  | T | C | A | A | A | A | A | A |
| SNP76 | 4 | 27.358  | 4981234  | G | T | B | B | B | B | B | B |
| SNP77 | 4 | 28.164  | 5155338  | A | T | A | A | A | A | A | A |
| SNP78 | 4 | 30.983  | 5756433  | C | T | A | A | A | A | A | A |
| SNP79 | 4 | 34.723  | 6571438  | C | A | B | B | B | B | B | B |
| SNP80 | 4 | 36.210  | 6888107  | T | G | A | A | A | A | A | A |
| SNP81 | 4 | 39.468  | 7584976  | C | T | A | A | A | A | A | A |
| SNP82 | 4 | 42.615  | 8421224  | A | C | B | B | B | B | B | B |
| SNP83 | 4 | 42.934  | 8529326  | A | T | A | A | A | A | A | A |
| SNP84 | 4 | 44.097  | 8977099  | G | A | A | A | A | A | A | A |
| SNP85 | 4 | 55.699  | 37635182 | C | T | A | A | A | A | A | A |
| SNP86 | 4 | 63.882  | 44453699 | G | A | B | B | B | B | B | B |
| SNP87 | 4 | 79.868  | 49190065 | G | T | A | A | A | A | A | A |
| SNP88 | 4 | 79.868  | 49190123 | A | T | A | A | A | A | A | A |
| SNP89 | 4 | 82.873  | 49966272 | A | C | A | A | A | A | A | A |

| SNP ID | Chr | cM | Location of SNPs on chromosomes | Deposited line | SHASTA | ERUDE | HAITSU SP | FOREST | TBR-449 | CASTLE | GREEN FACE |
|---|---|---|---|---|---|---|---|---|---|---|---|
| SNP60 | 3 | 92.321  | 45636043 | A | A | A | H | H | A | A | A |
| SNP61 | 3 | 93.347  | 47819830 | A | A | H | H | A | A | A | A |
| SNP62 | 3 | 93.945  | 48535735 | B | A | B | H | H | H | H | H |
| SNP63 | 3 | 98.958  | 52628849 | B | B | B | B | H | H | H | B |
| SNP64 | 3 | 99.714  | 53167534 | B | B | B | H | H | H | B | B |
| SNP65 | 3 | 109.268 | 58494494 | A | A | A | A | A | H | A | A |
| SNP66 | 3 | 109.415 | 58569947 | A | H | H | H | A | H | H | A |
| SNP67 | 3 | 113.736 | 58628362 | B | H | H | H | B | H | H | B |
| SNP68 | 3 | 117.120 | 60116952 | B | H | B | B | B | H | B | B |
| SNP69 | 3 | 121.679 | 61115979 | B | B | H | B | H | B | B | B |
| SNP70 | 3 | 125.279 | 62286307 | B | A | H | H | B | B | H | H |
| SNP71 | 3 | 131.139 | 63119854 | B | A | H | H | B | H | H | H |
| SNP72 | 3 | 131.253 | 64347040 | B | H | H | H | H | H | B | B |
| SNP73 | 3 | 11.174  | 64369480 | A | B | H | H | A | H | A | A |
| SNP74 | 4 | 109.268 | 1826660  | A | A | H | H | A | A | A | A |
| SNP75 | 4 | 14.947  | 2437167  | A | B | B | B | B | B | B | H |
| SNP76 | 4 | 27.358  | 4981234  | B | B | B | H | H | A | B | H |

TABLE 4C-continued

| SNP ID | Chr | cM | Location of SNPs on chromosomes | | | | | | | | |
|---|---|---|---|---|---|---|---|---|---|---|---|
| SNP77 | 4 | 28.164 | 5155338 | A | B | B | B | B | B | B | B |
| SNP78 | 4 | 30.983 | 5756433 | A | B | B | B | B | B | B | B |
| SNP79 | 4 | 34.723 | 6571438 | B | H | H | H | A | H | H | A |
| SNP80 | 4 | 36.210 | 6888107 | A | H | B | B | B | H | H | H |
| SNP81 | 4 | 39.468 | 7584976 | A | B | B | B | B | B | B | B |
| SNP82 | 4 | 42.615 | 8421224 | B | A | A | A | A | H | A | A |
| SNP83 | 4 | 42.934 | 8529326 | A | A | H | H | B | A | H | H |
| SNP84 | 4 | 44.097 | 8977099 | A | B | H | H | B | B | H | H |
| SNP85 | 4 | 55.699 | 37635182 | A | B | B | B | H | H | H | H |
| SNP86 | 4 | 63.882 | 44453699 | B | H | B | B | B | H | B | H |
| SNP87 | 4 | 79.868 | 49190065 | A | B | H | H | A | H | H | H |
| SNP88 | 4 | 79.868 | 49190123 | A | A | H | H | A | H | A | A |
| SNP89 | 4 | 82.873 | 49966272 | A | A | H | H | H | B | H | A |

| SNP ID | Chr | cM | Location of SNPs on chromosomes | MEGA-DOME | PIXEL | SK9-099 | GREEN CANNON | GRAN-DOME | HEART-LAND | DES-TINY | Gypsy |
|---|---|---|---|---|---|---|---|---|---|---|---|
| SNP60 | 3 | 92.321 | 45636043 | A | A | H | A | H | A | A | A |
| SNP61 | 3 | 93.347 | 47819830 | A | A | H | A | H | A | A | A |
| SNP62 | 3 | 93.945 | 48535735 | A | H | A | H | H | B | H | H |
| SNP63 | 3 | 98.958 | 52628849 | A | A | A | H | H | B | A | H |
| SNP64 | 3 | 99.714 | 53167534 | B | H | H | B | H | B | B | H |
| SNP65 | 3 | 109.268 | 58494494 | A | B | B | A | B | A | A | H |
| SNP66 | 3 | 109.415 | 58569947 | H | H | H | A | H | A | A | H |
| SNP67 | 3 | 113.736 | 58628362 | H | A | H | H | H | B | B | H |
| SNP68 | 3 | 117.120 | 60116952 | B | H | H | B | H | B | B | H |
| SNP69 | 3 | 121.679 | 61115979 | B | H | H | H | H | B | B | H |
| SNP70 | 3 | 125.279 | 62286307 | A | H | H | H | B | B | B | H |
| SNP71 | 3 | 131.139 | 63119854 | A | A | A | H | H | B | H | A |
| SNP72 | 3 | 131.253 | 64347040 | B | H | H | H | H | B | B | H |
| SNP73 | 3 | 11.174 | 64369480 | A | H | H | H | H | A | A | H |
| SNP74 | 4 | 109.268 | 1826660 | H | A | H | H | A | A | A | A |
| SNP75 | 4 | 14.947 | 2437167 | B | B | H | H | H | B | H | H |
| SNP76 | 4 | 27.358 | 4981234 | B | B | B | A | B | A | B | B |
| SNP77 | 4 | 28.164 | 5155338 | B | H | B | B | H | B | A | H |
| SNP78 | 4 | 30.983 | 5756433 | B | B | B | B | B | B | B | B |
| SNP79 | 4 | 34.723 | 6571438 | H | B | B | H | B | A | B | H |
| SNP80 | 4 | 36.210 | 6888107 | H | H | H | B | H | B | H | H |
| SNP81 | 4 | 39.468 | 7584976 | B | B | B | B | B | B | B | B |
| SNP82 | 4 | 42.615 | 8421224 | A | A | A | A | A | A | A | B |
| SNP83 | 4 | 42.934 | 8529326 | A | A | H | H | A | B | A | A |
| SNP84 | 4 | 44.097 | 8977099 | H | B | H | B | B | B | B | B |
| SNP85 | 4 | 55.699 | 37635182 | B | B | B | B | B | A | B | B |
| SNP86 | 4 | 63.882 | 44453699 | B | H | B | B | B | B | B | H |
| SNP87 | 4 | 79.868 | 49190065 | B | B | B | H | H | A | H | B |
| SNP88 | 4 | 79.868 | 49190123 | H | H | A | H | A | A | A | H |
| SNP89 | 4 | 82.873 | 49966272 | A | H | H | H | H | B | A | B |

| SNP ID | Chr | cM | Location of SNPs on chromosomes | Emerald Crown | Marathon | Avenger | Imperial | SUBARU | FIGHT-ER | SHIK-IMIDORI 96 | SPEED DOME 052 | IRON-MAN |
|---|---|---|---|---|---|---|---|---|---|---|---|---|
| SNP60 | 3 | 92.321 | 45636043 | H | A | H | H | A | H | H | A | A |
| SNP61 | 3 | 93.347 | 47819830 | H | A | H | H | A | H | H | A | A |
| SNP62 | 3 | 93.945 | 48535735 | A | B | H | A | H | A | A | H | H |
| SNP63 | 3 | 98.958 | 52628849 | A | H | H | H | H | A | H | H | B |
| SNP64 | 3 | 99.714 | 53167534 | H | H | H | H | B | B | B | B | B |
| SNP65 | 3 | 109.268 | 58494494 | B | B | H | H | A | H | A | A | H |
| SNP66 | 3 | 109.415 | 58569947 | H | H | H | H | A | H | H | H | H |
| SNP67 | 3 | 113.736 | 58628362 | H | H | H | H | B | H | B | H | H |
| SNP68 | 3 | 117.120 | 60116952 | H | H | H | H | B | H | H | H | H |
| SNP69 | 3 | 121.679 | 61115979 | H | H | H | H | B | A | H | B | H |
| SNP70 | 3 | 125.279 | 62286307 | H | B | B | H | H | H | A | H | B |
| SNP71 | 3 | 131.139 | 63119854 | A | H | H | A | H | A | A | H | H |
| SNP72 | 3 | 131.253 | 64347040 | H | H | H | H | B | A | H | B | A |
| SNP73 | 3 | 11.174 | 64369480 | H | H | H | H | A | B | H | A | B |
| SNP74 | 4 | 109.268 | 1826660 | A | A | A | A | A | A | H | A | A |
| SNP75 | 4 | 14.947 | 2437167 | B | H | H | H | A | B | B | B | B |
| SNP76 | 4 | 27.358 | 4981234 | B | B | B | H | B | B | B | B | B |
| SNP77 | 4 | 28.164 | 5155338 | B | A | H | B | B | B | B | B | A |
| SNP78 | 4 | 30.983 | 5756433 | B | B | B | B | B | B | B | B | B |
| SNP79 | 4 | 34.723 | 6571438 | B | B | B | H | B | B | H | H | B |
| SNP80 | 4 | 36.210 | 6888107 | B | A | H | B | H | B | B | B | A |
| SNP81 | 4 | 39.468 | 7584976 | B | B | B | B | B | B | B | B | B |
| SNP82 | 4 | 42.615 | 8421224 | A | H | A | A | A | A | A | A | H |
| SNP83 | 4 | 42.934 | 8529326 | A | A | A | H | A | A | A | A | A |
| SNP84 | 4 | 44.097 | 8977099 | B | B | B | B | B | B | B | B | B |

TABLE 4C-continued

| SNP85 | 4 | 55.699 | 37635182 | B | B | B | B | B | B | B | B | B |
| SNP86 | 4 | 63.882 | 44453699 | B | H | B | B | B | B | B | B | B |
| SNP87 | 4 | 79.868 | 49190065 | B | H | H | B | H | B | B | H | B |
| SNP88 | 4 | 79.868 | 49190123 | A | H | A | H | A | A | A | A | B |
| SNP89 | 4 | 82.873 | 49966272 | H | H | H | H | A | H | A | H | H |

TABLE 4D

| SNP ID | Chr | cM | Location of SNPs on chromosomes | A | B | Deposited line | Deposited line | Deposited line | Deposited line | Deposited line | Deposited line |
|---|---|---|---|---|---|---|---|---|---|---|---|
| SNP90 | 4 | 89.350 | 51208004 | A | C | A | A | A | A | A | A |
| SNP91 | 4 | 89.440 | 51222103 | T | C | A | A | A | A | A | A |
| SNP92 | 4 | 89.932 | 51294829 | C | G | B | B | B | B | B | B |
| SNP93 | 4 | 92.074 | 51600428 | T | A | A | A | A | A | A | A |
| SNP94 | 4 | 92.790 | 51699975 | T | C | A | A | A | A | A | A |
| SNP95 | 4 | 92.972 | 51724947 | A | G | A | A | A | A | A | A |
| SNP96 | 4 | 97.323 | 52290476 | G | A | A | A | A | A | A | A |
| SNP97 | 4 | 99.247 | 52528712 | A | C | B | B | B | B | B | B |
| SNP98 | 4 | 103.716 | 53075337 | G | A | B | B | B | B | B | B |
| SNP99 | 4 | 104.352 | 53152564 | G | T | B | B | B | B | B | B |
| SNP100 | 5 | 4.966 | 1140114 | A | G | A | A | A | A | A | A |
| SNP101 | 5 | 4.976 | 1141506 | G | T | B | B | B | B | B | B |
| SNP102 | 5 | 7.820 | 1514669 | G | C | B | B | B | B | B | B |
| SNP103 | 5 | 7.820 | 1514715 | G | C | B | B | B | B | B | B |
| SNP104 | 5 | 15.375 | 2554344 | T | C | B | B | B | B | B | B |
| SNP105 | 5 | 15.608 | 2588838 | A | G | A | A | A | A | A | A |
| SNP106 | 5 | 16.607 | 2732567 | T | C | B | B | B | B | B | B |
| SNP107 | 5 | 31.035 | 4956729 | A | G | B | B | B | B | B | B |
| SNP108 | 5 | 41.841 | 10181899 | C | T | A | A | A | A | A | A |
| SNP109 | 5 | 44.362 | 12281717 | T | A | B | B | B | B | B | B |
| SNP110 | 5 | 47.460 | 18521685 | G | T | A | A | A | A | A | A |
| SNP111 | 5 | 48.732 | 30884244 | G | C | B | B | B | B | B | B |
| SNP112 | 5 | 51.345 | 37641346 | G | C | A | A | A | A | A | A |
| SNP113 | 5 | 52.528 | 38794559 | T | C | A | A | A | A | A | A |
| SNP114 | 5 | 56.319 | 41364962 | T | C | B | B | B | B | B | B |
| SNP115 | 5 | 56.778 | 41506661 | C | T | B | B | B | B | B | B |
| SNP116 | 5 | 68.679 | 43448077 | C | T | B | B | B | B | B | B |
| SNP117 | 5 | 71.693 | 43800880 | C | G | B | B | B | B | B | B |
| SNP118 | 5 | 76.081 | 44280290 | C | T | B | B | B | B | B | B |
| SNP119 | 5 | 76.505 | 44322768 | T | C | A | A | A | A | A | A |

| SNP ID | Chr | cM | Location of SNPs on chromosomes | Deposited line | SHASTA | ERUDE | HAITSU SP | FOREST | TBR-449 | CASTLE | GREEN FACE |
|---|---|---|---|---|---|---|---|---|---|---|---|
| SNP90 | 4 | 89.350 | 51208004 | A | B | H | B | B | B | B | H |
| SNP91 | 4 | 89.440 | 51222103 | A | B | H | B | B | B | B | H |
| SNP92 | 4 | 89.932 | 51294829 | B | A | A | A | A | B | H | A |
| SNP93 | 4 | 92.074 | 51600428 | A | B | B | B | B | B | B | B |
| SNP94 | 4 | 92.790 | 51699975 | A | B | B | B | H | H | A | H |
| SNP95 | 4 | 92.972 | 51724947 | A | B | B | B | H | H | A | H |
| SNP96 | 4 | 97.323 | 52290476 | A | H | A | H | H | A | A | B |
| SNP97 | 4 | 99.247 | 52528712 | B | B | H | H | B | A | H | H |
| SNP98 | 4 | 103.716 | 53075337 | B | H | H | H | H | A | B | H |
| SNP99 | 4 | 104.352 | 53152564 | B | H | B | B | B | B | H | B |
| SNP100 | 5 | 4.966 | 1140114 | A | A | H | B | H | H | A | H |
| SNP101 | 5 | 4.976 | 1141506 | B | B | H | A | H | H | B | H |
| SNP102 | 5 | 7.820 | 1514669 | B | H | H | B | H | H | B | B |
| SNP103 | 5 | 7.820 | 1514715 | B | H | H | B | H | H | B | B |
| SNP104 | 5 | 15.375 | 2554344 | B | H | A | A | A | A | H | A |
| SNP105 | 5 | 15.608 | 2588838 | A | H | B | B | B | B | H | B |
| SNP106 | 5 | 16.607 | 2732567 | B | A | A | A | H | A | B | A |
| SNP107 | 5 | 31.035 | 4956729 | B | H | A | H | H | H | A | A |
| SNP108 | 5 | 41.841 | 10181899 | A | H | H | H | A | B | B | H |
| SNP109 | 5 | 44.362 | 12281717 | B | A | A | B | B | B | A | B |
| SNP110 | 5 | 47.460 | 18521685 | A | B | B | H | A | H | A | A |
| SNP111 | 5 | 48.732 | 30884244 | B | B | H | B | H | H | H | B |
| SNP112 | 5 | 51.345 | 37641346 | A | H | H | H | B | H | H | H |
| SNP113 | 5 | 52.528 | 38794559 | A | H | A | A | A | A | H | H |
| SNP114 | 5 | 56.319 | 41364962 | B | A | B | B | H | H | A | H |
| SNP115 | 5 | 56.778 | 41506661 | B | H | B | B | H | H | A | H |
| SNP116 | 5 | 68.679 | 43448077 | B | A | B | H | A | H | H | B |
| SNP117 | 5 | 71.693 | 43800880 | B | H | A | H | B | H | B | A |

TABLE 4D-continued

| SNP ID | Chr | cM | Location of SNPs on chromosomes | | | | | | | | |
|---|---|---|---|---|---|---|---|---|---|---|---|
| SNP118 | 5 | 76.081 | 44280290 | B | H | B | B | B | B | B | A |
| SNP119 | 5 | 76.505 | 44322768 | A | B | B | H | H | B | H | B |

| SNP ID | Chr | cM | Location of SNPs on chromosomes | MEGA-DOME | PIXEL | SK9-099 | GREEN CANNON | GRAN-DOME | HEART-LAND | DES-TINY | Gypsy |
|---|---|---|---|---|---|---|---|---|---|---|---|
| SNP90 | 4 | 89.350 | 51208004 | B | B | B | B | H | B | H | B |
| SNP91 | 4 | 89.440 | 51222103 | H | H | H | B | A | B | H | H |
| SNP92 | 4 | 89.932 | 51294829 | A | H | H | A | B | B | A | A |
| SNP93 | 4 | 92.074 | 51600428 | H | B | B | H | H | B | H | H |
| SNP94 | 4 | 92.790 | 51699975 | H | H | H | B | H | A | A | B |
| SNP95 | 4 | 92.972 | 51724947 | H | H | H | B | H | A | A | H |
| SNP96 | 4 | 97.323 | 52290476 | H | A | A | H | A | A | A | A |
| SNP97 | 4 | 99.247 | 52528712 | B | H | H | B | H | A | B | H |
| SNP98 | 4 | 103.716 | 53075337 | H | H | H | H | H | H | B | H |
| SNP99 | 4 | 104.352 | 53152564 | H | B | B | B | B | H | B | B |
| SNP100 | 5 | 4.966 | 1140114 | A | H | H | A | B | A | A | H |
| SNP101 | 5 | 4.976 | 1141506 | B | H | H | B | A | B | H | H |
| SNP102 | 5 | 7.820 | 1514669 | B | B | B | H | B | A | B | B |
| SNP103 | 5 | 7.820 | 1514715 | B | B | B | H | B | A | B | B |
| SNP104 | 5 | 15.375 | 2554344 | B | H | H | B | A | A | H | A |
| SNP105 | 5 | 15.608 | 2588838 | A | H | H | A | B | B | H | H |
| SNP106 | 5 | 16.607 | 2732567 | H | H | H | B | A | B | H | A |
| SNP107 | 5 | 31.035 | 4956729 | A | B | B | H | B | A | A | H |
| SNP108 | 5 | 41.841 | 10181899 | H | H | H | H | H | A | H | H |
| SNP109 | 5 | 44.362 | 12281717 | B | B | H | H | B | B | B | A |
| SNP110 | 5 | 47.460 | 18521685 | A | B | B | B | H | A | A | B |
| SNP111 | 5 | 48.732 | 30884244 | B | B | H | B | B | A | B | B |
| SNP112 | 5 | 51.345 | 37641346 | A | H | B | B | H | B | H | H |
| SNP113 | 5 | 52.528 | 38794559 | B | H | A | H | A | A | H | H |
| SNP114 | 5 | 56.319 | 41364962 | A | H | B | H | B | A | H | B |
| SNP115 | 5 | 56.778 | 41506661 | A | H | H | H | B | A | H | B |
| SNP116 | 5 | 68.679 | 43448077 | H | B | B | B | H | A | H | H |
| SNP117 | 5 | 71.693 | 43800880 | H | H | H | B | B | B | B | H |
| SNP118 | 5 | 76.081 | 44280290 | H | B | H | B | B | B | H | B |
| SNP119 | 5 | 76.505 | 44322768 | A | H | H | H | B | H | H | B |

| SNP ID | Chr | cM | Location of SNPs on chromosomes | Emerald Crown | Marathon | Avenger | Imperial | SUBARU | FIGHT-ER | SHIK-IMIDORI 96 | SPEED DOME 052 | IRON-MAN |
|---|---|---|---|---|---|---|---|---|---|---|---|---|
| SNP90 | 4 | 89.350 | 51208004 | B | H | H | H | H | B | B | B | H |
| SNP91 | 4 | 89.440 | 51222103 | H | A | A | H | H | H | B | B | A |
| SNP92 | 4 | 89.932 | 51294829 | H | B | B | B | H | H | A | A | H |
| SNP93 | 4 | 92.074 | 51600428 | B | H | H | H | H | B | B | B | A |
| SNP94 | 4 | 92.790 | 51699975 | H | H | H | H | A | H | A | H | H |
| SNP95 | 4 | 92.972 | 51724947 | B | H | H | H | A | H | A | H | H |
| SNP96 | 4 | 97.323 | 52290476 | A | A | A | H | A | A | H | H | H |
| SNP97 | 4 | 99.247 | 52528712 | H | H | H | H | B | H | H | B | B |
| SNP98 | 4 | 103.716 | 53075337 | H | H | H | H | H | H | H | B | B |
| SNP99 | 4 | 104.352 | 53152564 | B | B | B | B | B | B | B | B | B |
| SNP100 | 5 | 4.966 | 1140114 | H | B | B | H | H | H | A | H | B |
| SNP101 | 5 | 4.976 | 1141506 | H | A | A | H | H | H | B | H | A |
| SNP102 | 5 | 7.820 | 1514669 | B | B | B | B | B | B | B | B | B |
| SNP103 | 5 | 7.820 | 1514715 | B | B | B | B | B | B | B | B | B |
| SNP104 | 5 | 15.375 | 2554344 | H | A | A | H | H | H | B | H | A |
| SNP105 | 5 | 15.608 | 2588838 | H | B | B | H | H | H | A | H | B |
| SNP106 | 5 | 16.607 | 2732567 | H | A | A | A | H | H | B | H | A |
| SNP107 | 5 | 31.035 | 4956729 | H | B | B | H | H | H | H | A | B |
| SNP108 | 5 | 41.841 | 10181899 | H | H | H | H | H | H | H | H | B |
| SNP109 | 5 | 44.362 | 12281717 | B | B | B | H | H | H | A | B | H |
| SNP110 | 5 | 47.460 | 18521685 | B | H | H | B | B | B | B | A | A |
| SNP111 | 5 | 48.732 | 30884244 | B | B | B | H | B | B | H | B | B |
| SNP112 | 5 | 51.345 | 37641346 | H | H | H | H | H | H | B | A | H |
| SNP113 | 5 | 52.528 | 38794559 | H | A | A | H | H | H | B | H | B |
| SNP114 | 5 | 56.319 | 41364962 | H | B | B | B | H | H | A | H | H |
| SNP115 | 5 | 56.778 | 41506661 | H | B | B | H | H | H | A | H | H |
| SNP116 | 5 | 68.679 | 43448077 | B | H | H | H | B | H | B | H | B |
| SNP117 | 5 | 71.693 | 43800880 | B | H | H | H | B | B | B | B | H |
| SNP118 | 5 | 76.081 | 44280290 | B | B | H | H | H | B | B | B | B |
| SNP119 | 5 | 76.505 | 44322768 | A | B | H | H | H | A | A | A | H |

TABLE 4E

| SNP ID | Chr | cM | Location of SNPs on chromosomes | A | B | Deposited line | Deposited line | Deposited line | Deposited line | Deposited line | Deposited line |
|---|---|---|---|---|---|---|---|---|---|---|---|
| SNP120 | 5 | 76.505 | 44322808 | C | G | A | A | A | A | A | A |
| SNP121 | 5 | 81.616 | 44870044 | G | A | A | A | A | A | A | A |
| SNP122 | 5 | 86.439 | 45492393 | T | C | B | B | B | B | B | B |
| SNP123 | 5 | 86.707 | 45530316 | T | G | A | A | A | A | A | A |
| SNP124 | 5 | 93.187 | 46733625 | C | T | B | B | B | B | B | B |
| SNP125 | 6 | 4.372 | 724690 | C | T | B | B | B | B | B | B |
| SNP126 | 6 | 6.800 | 1007519 | A | G | B | B | B | B | B | B |
| SNP127 | 6 | 22.962 | 2922287 | G | C | B | B | B | B | B | B |
| SNP128 | 6 | 24.373 | 3114174 | G | T | B | B | B | B | B | B |
| SNP129 | 6 | 28.036 | 3627446 | A | G | B | B | B | B | B | B |
| SNP130 | 6 | 31.980 | 4189191 | A | C | A | A | A | A | A | A |
| SNP131 | 6 | 39.058 | 5440585 | A | G | A | A | A | A | A | A |
| SNP132 | 6 | 39.058 | 5440620 | A | T | A | A | A | A | A | A |
| SNP133 | 6 | 43.889 | 6852182 | G | A | A | A | A | A | A | A |
| SNP134 | 6 | 44.870 | 7272721 | G | A | B | B | B | B | B | B |
| SNP135 | 6 | 48.965 | 10618159 | G | A | A | A | A | A | A | A |
| SNP136 | 6 | 50.138 | 13042773 | C | T | B | B | B | B | B | B |
| SNP137 | 6 | 50.525 | 13884163 | T | C | B | B | B | B | B | B |
| SNP138 | 6 | 52.027 | 15217464 | G | C | A | A | A | A | A | A |
| SNP139 | 6 | 55.973 | 18016782 | G | C | A | A | A | A | A | A |
| SNP140 | 6 | 66.709 | 24827566 | A | G | B | B | B | B | B | B |
| SNP141 | 6 | 67.753 | 29368693 | G | A | B | B | B | B | B | B |
| SNP142 | 6 | 67.775 | 30981277 | C | G | A | A | A | A | A | A |
| SNP143 | 6 | 70.902 | 36429664 | G | A | B | B | B | B | B | B |
| SNP144 | 6 | 71.169 | 36729257 | C | G | B | B | B | B | B | B |
| SNP145 | 6 | 73.316 | 38879766 | T | G | B | B | B | B | B | B |
| SNP146 | 7 | 1.305 | 20364274 | A | G | A | A | A | A | A | A |
| SNP147 | 7 | 1.653 | 25133727 | A | C | B | B | B | B | B | B |
| SNP148 | 7 | 3.260 | 29384441 | A | G | A | A | A | A | A | A |
| SNP149 | 7 | 12.311 | 33894835 | G | A | B | B | B | B | B | B |

| SNP ID | Chr | cM | Location of SNPs on chromosomes | Deposited line | SHASTA | ERUDE | HAITSU SP | FOREST | TBR-449 | CASTLE | GREEN FACE |
|---|---|---|---|---|---|---|---|---|---|---|---|
| SNP120 | 5 | 76.505 | 44322808 | A | B | H | H | B | H | B | B |
| SNP121 | 5 | 81.616 | 44870044 | A | H | H | A | H | H | H | B |
| SNP122 | 5 | 86.439 | 45492393 | B | B | H | H | B | H | B | B |
| SNP123 | 5 | 86.707 | 45530316 | A | A | H | H | A | B | A | A |
| SNP124 | 5 | 93.187 | 46733625 | B | B | H | A | B | A | B | B |
| SNP125 | 6 | 4.372 | 724690 | B | H | H | B | H | H | H | H |
| SNP126 | 6 | 6.800 | 1007519 | B | H | A | H | A | H | H | A |
| SNP127 | 6 | 22.962 | 2922287 | B | H | H | H | B | H | B | A |
| SNP128 | 6 | 24.373 | 3114174 | B | B | B | H | A | H | H | H |
| SNP129 | 6 | 28.036 | 3627446 | B | B | B | H | A | H | H | H |
| SNP130 | 6 | 31.980 | 4189191 | A | A | A | A | A | A | A | H |
| SNP131 | 6 | 39.058 | 5440585 | A | A | H | H | A | H | A | A |
| SNP132 | 6 | 39.058 | 5440620 | A | A | H | H | A | H | A | A |
| SNP133 | 6 | 43.889 | 6852182 | A | A | H | B | H | H | A | H |
| SNP134 | 6 | 44.870 | 7272721 | B | B | B | A | B | H | B | B |
| SNP135 | 6 | 48.965 | 10618159 | A | A | H | H | A | H | A | H |
| SNP136 | 6 | 50.138 | 13042773 | B | H | B | H | B | H | B | B |
| SNP137 | 6 | 50.525 | 13884163 | B | H | B | H | A | B | B | H |
| SNP138 | 6 | 52.027 | 15217464 | A | H | H | B | H | H | A | H |
| SNP139 | 6 | 55.973 | 18016782 | A | H | H | H | A | H | H | A |
| SNP140 | 6 | 66.709 | 24827566 | B | H | B | H | B | H | B | H |
| SNP141 | 6 | 67.753 | 29368693 | B | H | H | H | B | H | B | H |
| SNP142 | 6 | 67.775 | 30981277 | A | B | B | B | B | B | B | B |
| SNP143 | 6 | 70.902 | 36429664 | B | B | H | H | B | H | B | H |
| SNP144 | 6 | 71.169 | 36729257 | B | H | H | H | B | B | B | H |
| SNP145 | 6 | 73.316 | 38879766 | B | H | B | H | B | A | B | B |
| SNP146 | 7 | 1.305 | 20364274 | A | H | H | H | A | H | A | H |
| SNP147 | 7 | 1.653 | 25133727 | B | B | B | B | B | B | H | B |
| SNP148 | 7 | 3.260 | 29384441 | A | H | B | H | A | H | H | H |
| SNP149 | 7 | 12.311 | 33894835 | B | B | B | B | B | B | B | H |

| SNP ID | Chr | cM | Location of SNPs on chromosomes | MEGA-DOME | PIXEL | SK9-099 | GREEN CANNON | GRAN-DOME | HEART-LAND | DES-TINY | Gypsy |
|---|---|---|---|---|---|---|---|---|---|---|---|
| SNP120 | 5 | 76.505 | 44322808 | A | H | H | H | H | B | H | B |
| SNP121 | 5 | 81.616 | 44870044 | A | A | H | A | H | H | H | A |
| SNP122 | 5 | 86.439 | 45492393 | B | H | B | H | B | B | B | H |

TABLE 4E-continued

| SNP ID | C hr | cM | Location of SNPs on chromosomes | | | | | | | | |
|---|---|---|---|---|---|---|---|---|---|---|---|
| SNP123 | 5 | 86.707 | 45530316 | A | H | A | H | A | A | A | B |
| SNP124 | 5 | 93.187 | 46733625 | B | H | B | H | B | B | B | A |
| SNP125 | 6 | 4.372 | 724690 | B | B | H | B | H | A | H | H |
| SNP126 | 6 | 6.800 | 1007519 | B | B | H | H | H | A | H | H |
| SNP127 | 6 | 22.962 | 2922287 | B | H | H | H | H | B | B | H |
| SNP128 | 6 | 24.373 | 3114174 | B | B | H | B | H | A | H | H |
| SNP129 | 6 | 28.036 | 3627446 | B | B | H | H | H | A | H | H |
| SNP130 | 6 | 31.980 | 4189191 | A | A | A | A | A | A | A | A |
| SNP131 | 6 | 39.058 | 5440585 | A | H | H | H | H | A | A | H |
| SNP132 | 6 | 39.058 | 5440620 | A | H | H | H | H | A | A | H |
| SNP133 | 6 | 43.889 | 6852182 | A | H | B | B | A | A | A | B |
| SNP134 | 6 | 44.870 | 7272721 | B | H | A | H | A | B | B | B |
| SNP135 | 6 | 48.965 | 10618159 | A | H | B | H | H | A | A | H |
| SNP136 | 6 | 50.138 | 13042773 | B | B | B | B | B | B | B | B |
| SNP137 | 6 | 50.525 | 13884163 | B | B | B | B | B | B | B | B |
| SNP138 | 6 | 52.027 | 15217464 | A | H | B | B | H | A | A | H |
| SNP139 | 6 | 55.973 | 18016782 | B | B | B | H | H | A | H | H |
| SNP140 | 6 | 66.709 | 24827566 | B | B | B | B | B | B | B | H |
| SNP141 | 6 | 67.753 | 29368693 | B | H | H | H | H | B | B | H |
| SNP142 | 6 | 67.775 | 30981277 | B | B | B | B | B | B | B | B |
| SNP143 | 6 | 70.902 | 36429664 | B | H | B | B | B | B | B | A |
| SNP144 | 6 | 71.169 | 36729257 | A | H | B | B | B | B | H | B |
| SNP145 | 6 | 73.316 | 38879766 | B | H | H | B | H | B | B | A |
| SNP146 | 7 | 1.305 | 20364274 | A | A | A | H | A | B | A | A |
| SNP147 | 7 | 1.653 | 25133727 | H | H | B | B | B | B | H | B |
| SNP148 | 7 | 3.260 | 29384441 | H | B | H | A | A | A | H | B |
| SNP149 | 7 | 12.311 | 33894835 | B | B | B | B | B | B | B | B |

| SNP ID | C hr | cM | Location of SNPs on chromosomes | Emerald Crown | Marathon | Avenger | Imperial | SUBARU | FIGHTER | SHIK-IMIDORI 96 | SPEED DOME 052 | IRON-MAN |
|---|---|---|---|---|---|---|---|---|---|---|---|---|
| SNP120 | 5 | 76.505 | 44322808 | A | B | H | H | H | A | A | A | H |
| SNP121 | 5 | 81.616 | 44870044 | A | H | H | H | A | A | H | A | A |
| SNP122 | 5 | 86.439 | 45492393 | B | H | B | B | B | B | B | H | H |
| SNP123 | 5 | 86.707 | 45530316 | A | H | A | A | A | A | A | A | H |
| SNP124 | 5 | 93.187 | 46733625 | B | A | B | B | B | B | B | B | B |
| SNP125 | 6 | 4.372 | 724690 | B | H | H | H | H | H | B | H | H |
| SNP126 | 6 | 6.800 | 1007519 | B | H | H | H | H | H | A | H | B |
| SNP127 | 6 | 22.962 | 2922287 | H | H | H | A | B | H | A | H | B |
| SNP128 | 6 | 24.373 | 3114174 | B | H | H | H | H | H | B | H | H |
| SNP129 | 6 | 28.036 | 3627446 | B | H | H | B | H | H | B | H | H |
| SNP130 | 6 | 31.980 | 4189191 | A | A | A | A | A | A | A | A | A |
| SNP131 | 6 | 39.058 | 5440585 | H | H | H | H | A | H | A | H | A |
| SNP132 | 6 | 39.058 | 5440620 | H | H | H | H | A | H | A | H | A |
| SNP133 | 6 | 43.889 | 6852182 | H | A | H | B | A | A | A | A | A |
| SNP134 | 6 | 44.870 | 7272721 | H | H | A | H | B | H | B | B | B |
| SNP135 | 6 | 48.965 | 10618159 | H | H | H | H | A | H | A | A | A |
| SNP136 | 6 | 50.138 | 13042773 | B | B | B | H | B | B | B | H | B |
| SNP137 | 6 | 50.525 | 13884163 | B | B | B | B | B | B | B | H | B |
| SNP138 | 6 | 52.027 | 15217464 | H | H | H | H | A | H | A | H | A |
| SNP139 | 6 | 55.973 | 18016782 | B | H | H | H | H | H | H | H | A |
| SNP140 | 6 | 66.709 | 24827566 | B | B | B | H | B | B | B | B | B |
| SNP141 | 6 | 67.753 | 29368693 | H | H | H | H | B | H | B | B | B |
| SNP142 | 6 | 67.775 | 30981277 | B | B | B | B | B | B | B | B | B |
| SNP143 | 6 | 70.902 | 36429664 | B | A | B | H | B | B | B | B | B |
| SNP144 | 6 | 71.169 | 36729257 | H | B | B | H | B | H | B | H | B |
| SNP145 | 6 | 73.316 | 38879766 | H | H | H | H | H | H | H | B | B |
| SNP146 | 7 | 1.305 | 20364274 | A | A | A | H | A | A | H | H | H |
| SNP147 | 7 | 1.653 | 25133727 | H | B | B | H | B | B | B | H | B |
| SNP148 | 7 | 3.260 | 29384441 | H | H | A | H | H | H | A | H | H |
| SNP149 | 7 | 12.311 | 33894835 | B | B | B | B | B | B | B | B | B |

TABLE 4F

| SNP ID | C hr | cM | Location of SNPs on chromosomes | A | B | Deposited line | Deposited line | Deposited line | Deposited line | Deposited line | Deposited line |
|---|---|---|---|---|---|---|---|---|---|---|---|
| SNP150 | 7 | 13.369 | 34371604 | T | C | A | A | A | A | A | A |
| SNP151 | 7 | 13.825 | 34583372 | A | G | B | B | B | B | B | B |
| SNP152 | 7 | 25.291 | 38743951 | T | C | B | B | B | B | B | B |
| SNP153 | 7 | 28.998 | 40014701 | G | T | B | B | B | B | B | B |
| SNP154 | 7 | 37.842 | 43233659 | A | C | A | A | A | A | A | A |
| SNP155 | 7 | 38.592 | 43345503 | G | T | A | A | A | A | A | A |

TABLE 4F-continued

| SNP ID | Chr | cM | Location of SNPs on chromosomes | | | | | | | | |
|---|---|---|---|---|---|---|---|---|---|---|---|
| SNP156 | 7 | 41.700 | 43818102 | G | A | B | B | B | B | B | B |
| SNP157 | 7 | 43.584 | 44096110 | T | A | B | B | B | B | B | B |
| SNP158 | 7 | 44.266 | 44191945 | C | T | A | A | A | A | A | A |
| SNP159 | 7 | 44.266 | 44191975 | A | G | A | A | A | A | A | A |
| SNP160 | 7 | 46.334 | 44490415 | A | G | B | B | B | B | B | B |
| SNP161 | 7 | 48.124 | 44794150 | T | C | B | B | B | B | B | B |
| SNP162 | 7 | 54.996 | 46191816 | C | T | B | B | B | B | B | B |
| SNP163 | 7 | 61.162 | 47585593 | T | A | A | A | A | A | A | A |
| SNP164 | 7 | 61.702 | 47714484 | C | G | A | A | A | A | A | A |
| SNP165 | 7 | 63.419 | 48124324 | A | C | A | A | A | A | A | A |
| SNP166 | 7 | 63.806 | 48216530 | G | A | B | B | B | B | B | B |
| SNP167 | 8 | 0.016 | 148296 | A | G | B | B | B | B | B | B |
| SNP168 | 8 | 0.016 | 2426797 | G | C | A | A | A | A | A | A |
| SNP169 | 8 | 0.032 | 13520717 | C | T | B | B | B | B | B | B |
| SNP170 | 8 | 2.152 | 18675613 | A | G | A | A | A | A | A | A |
| SNP171 | 8 | 4.123 | 19739628 | T | C | B | B | B | B | B | B |
| SNP172 | 8 | 4.915 | 20071352 | C | G | A | A | A | A | A | A |
| SNP173 | 8 | 11.767 | 24841237 | G | C | B | B | B | B | B | B |
| SNP174 | 8 | 13.753 | 26341786 | C | G | A | A | A | A | A | A |
| SNP175 | 8 | 21.371 | 28667380 | T | A | A | A | A | A | A | A |
| SNP176 | 8 | 31.456 | 31835841 | C | T | A | A | A | A | A | A |
| SNP177 | 8 | 32.905 | 32719677 | T | G | B | B | B | B | B | B |
| SNP178 | 8 | 35.366 | 33804788 | C | T | A | A | A | A | A | A |
| SNP179 | 8 | 40.549 | 35972043 | T | G | A | A | A | A | A | A |

| SNP ID | Chr | cM | Location of SNPs on chromosomes | Deposited line | SHASTA | ERUDE | HAITSU SP | FOREST | TBR-449 | CASTLE | GREEN FACE |
|---|---|---|---|---|---|---|---|---|---|---|---|
| SNP150 | 7 | 13.369 | 34371604 | A | H | B | H | H | H | B | H |
| SNP151 | 7 | 13.825 | 34583372 | B | H | B | B | H | H | A | B |
| SNP152 | 7 | 25.291 | 38743951 | B | A | A | H | H | H | A | A |
| SNP153 | 7 | 28.998 | 40014701 | B | A | A | H | B | A | B | B |
| SNP154 | 7 | 37.842 | 43233659 | A | H | B | H | H | B | B | A |
| SNP155 | 7 | 38.592 | 43345503 | A | A | H | H | H | B | H | A |
| SNP156 | 7 | 41.700 | 43818102 | B | B | A | H | H | H | A | B |
| SNP157 | 7 | 43.584 | 44096110 | B | A | A | B | H | H | H | B |
| SNP158 | 7 | 44.266 | 44191945 | A | A | H | A | A | A | H | A |
| SNP159 | 7 | 44.266 | 44191975 | A | B | H | H | B | B | H | A |
| SNP160 | 7 | 46.334 | 44490415 | B | H | B | B | B | B | H | H |
| SNP161 | 7 | 48.124 | 44794150 | B | H | B | H | B | B | H | B |
| SNP162 | 7 | 54.996 | 46191816 | B | B | H | H | H | H | H | B |
| SNP163 | 7 | 61.162 | 47585593 | A | A | H | H | A | H | A | A |
| SNP164 | 7 | 61.702 | 47714484 | A | B | H | A | H | B | B | H |
| SNP165 | 7 | 63.419 | 48124324 | A | B | B | H | H | B | H | H |
| SNP166 | 7 | 63.806 | 48216530 | B | A | A | H | H | A | H | H |
| SNP167 | 8 | 0.016 | 148296 | B | H | H | B | B | B | H | B |
| SNP168 | 8 | 0.016 | 2426797 | A | H | A | H | H | H | H | B |
| SNP169 | 8 | 0.032 | 13520717 | B | B | H | H | B | B | B | B |
| SNP170 | 8 | 2.152 | 18675613 | A | A | H | A | H | B | B | A |
| SNP171 | 8 | 4.123 | 19739628 | B | B | H | H | H | B | B | B |
| SNP172 | 8 | 4.915 | 20071352 | A | H | B | H | H | H | B | H |
| SNP173 | 8 | 11.767 | 24841237 | B | H | A | H | B | H | H | H |
| SNP174 | 8 | 13.753 | 26341786 | A | B | H | A | A | B | H | A |
| SNP175 | 8 | 21.371 | 28667380 | A | H | H | H | A | B | H | A |
| SNP176 | 8 | 31.456 | 31835841 | A | B | A | A | H | B | B | A |
| SNP177 | 8 | 32.905 | 32719677 | B | A | A | A | A | A | A | H |
| SNP178 | 8 | 35.366 | 33804788 | A | A | H | B | H | A | A | A |
| SNP179 | 8 | 40.549 | 35972043 | A | A | A | H | A | H | A | A |

| SNP ID | Chr | cM | Location of SNPs on chromosomes | MEGA-DOME | PIXEL | SK9-099 | GREEN CANNON | GRAN-DOME | HEART-LAND | DES-TINY | Gypsy |
|---|---|---|---|---|---|---|---|---|---|---|---|
| SNP150 | 7 | 13.369 | 34371604 | B | H | B | H | B | H | H | H |
| SNP151 | 7 | 13.825 | 34583372 | A | H | A | A | H | A | H | H |
| SNP152 | 7 | 25.291 | 38743951 | A | A | A | A | H | A | H | A |
| SNP153 | 7 | 28.998 | 40014701 | B | H | H | A | B | B | B | B |
| SNP154 | 7 | 37.842 | 43233659 | B | B | H | A | B | H | B | B |
| SNP155 | 7 | 38.592 | 43345503 | A | H | A | H | A | B | A | H |
| SNP156 | 7 | 41.700 | 43818102 | A | H | A | H | B | A | H | B |
| SNP157 | 7 | 43.584 | 44096110 | B | B | B | B | B | A | B | B |
| SNP158 | 7 | 44.266 | 44191945 | B | A | A | H | A | A | A | A |
| SNP159 | 7 | 44.266 | 44191975 | H | H | H | H | H | B | A | B |
| SNP160 | 7 | 46.334 | 44490415 | H | B | B | B | B | B | B | B |
| SNP161 | 7 | 48.124 | 44794150 | A | H | A | H | H | B | H | H |
| SNP162 | 7 | 54.996 | 46191816 | B | B | B | B | B | A | B | B |
| SNP163 | 7 | 61.162 | 47585593 | H | B | H | H | A | A | H | H |

TABLE 4F-continued

| SNP164 | 7 | 61.702 | 47714484 | B | B | B | B | H | B | H | B |
| SNP165 | 7 | 63.419 | 48124324 | H | B | B | B | H | B | H | H |
| SNP166 | 7 | 63.806 | 48216530 | H | A | A | A | H | A | H | H |
| SNP167 | 8 | 0.016 | 148296 | H | B | A | B | H | B | B | B |
| SNP168 | 8 | 0.016 | 2426797 | B | H | H | H | H | A | B | H |
| SNP169 | 8 | 0.032 | 13520717 | B | B | H | B | H | B | B | B |
| SNP170 | 8 | 2.152 | 18675613 | H | H | B | H | H | B | H | A |
| SNP171 | 8 | 4.123 | 19739628 | H | B | H | H | H | B | B | H |
| SNP172 | 8 | 4.915 | 20071352 | H | H | B | H | H | B | H | H |
| SNP173 | 8 | 11.767 | 24841237 | H | H | H | H | H | B | B | H |
| SNP174 | 8 | 13.753 | 26341786 | B | H | H | B | H | A | A | B |
| SNP175 | 8 | 21.371 | 28667380 | H | H | H | B | H | A | A | H |
| SNP176 | 8 | 31.456 | 31835841 | B | B | B | B | H | B | H | B |
| SNP177 | 8 | 32.905 | 32719677 | A | A | A | A | H | A | H | A |
| SNP178 | 8 | 35.366 | 33804788 | H | H | H | A | A | A | H | A |
| SNP179 | 8 | 40.549 | 35972043 | A | H | H | H | H | A | A | B |

| SNP ID | Chr | cM | Location of SNPs on chromosomes | Emerald Crown | Marathon | Avenger | Imperial | SUBARU | FIGHTER | SHIK-IMIDORI 96 | SPEED DOME 052 | IRON-MAN |
|---|---|---|---|---|---|---|---|---|---|---|---|---|
| SNP150 | 7 | 13.369 | 34371604 | B | A | H | B | H | H | B | B | H |
| SNP151 | 7 | 13.825 | 34583372 | A | B | H | H | H | H | A | H | H |
| SNP152 | 7 | 25.291 | 38743951 | H | H | H | A | H | A | A | A | A |
| SNP153 | 7 | 28.998 | 40014701 | B | H | B | B | B | B | B | B | H |
| SNP154 | 7 | 37.842 | 43233659 | H | H | A | H | H | H | B | B | H |
| SNP155 | 7 | 38.592 | 43345503 | A | H | A | A | A | A | A | A | A |
| SNP156 | 7 | 41.700 | 43818102 | H | B | B | H | H | H | A | A | H |
| SNP157 | 7 | 43.584 | 44096110 | B | B | B | H | B | B | B | H | B |
| SNP158 | 7 | 44.266 | 44191945 | A | A | A | A | A | H | H | H | A |
| SNP159 | 7 | 44.266 | 44191975 | H | H | H | B | A | H | A | A | A |
| SNP160 | 7 | 46.334 | 44490415 | B | B | B | B | B | H | H | B | H |
| SNP161 | 7 | 48.124 | 44794150 | A | B | H | H | H | A | A | H | A |
| SNP162 | 7 | 54.996 | 46191816 | B | B | B | B | B | B | B | B | B |
| SNP163 | 7 | 61.162 | 47585593 | H | H | A | H | H | A | B | B | A |
| SNP164 | 7 | 61.702 | 47714484 | B | H | B | B | B | B | B | B | H |
| SNP165 | 7 | 63.419 | 48124324 | B | H | B | B | B | B | H | H | B |
| SNP166 | 7 | 63.806 | 48216530 | A | H | H | A | H | A | A | A | H |
| SNP167 | 8 | 0.016 | 148296 | H | B | H | H | B | H | A | B | H |
| SNP168 | 8 | 0.016 | 2426797 | H | H | B | H | H | H | B | B | H |
| SNP169 | 8 | 0.032 | 13520717 | H | B | H | B | H | B | B | B | B |
| SNP170 | 8 | 2.152 | 18675613 | B | H | H | B | H | B | B | H | A |
| SNP171 | 8 | 4.123 | 19739628 | H | B | H | H | B | H | B | H | H |
| SNP172 | 8 | 4.915 | 20071352 | B | H | H | H | B | H | B | H | A |
| SNP173 | 8 | 11.767 | 24841237 | H | H | H | H | B | H | B | B | H |
| SNP174 | 8 | 13.753 | 26341786 | H | H | H | H | A | H | A | H | A |
| SNP175 | 8 | 21.371 | 28667380 | H | H | H | H | A | H | A | A | H |
| SNP176 | 8 | 31.456 | 31835841 | B | H | H | B | H | B | B | H | B |
| SNP177 | 8 | 32.905 | 32719677 | A | H | H | A | H | A | A | A | A |
| SNP178 | 8 | 35.366 | 33804788 | H | A | A | H | H | A | A | B | A |
| SNP179 | 8 | 40.549 | 35972043 | H | H | H | H | A | H | A | A | H |

TABLE 4G

| SNP ID | Chr | cM | Location of SNPs on chromosomes | A | B | Deposited line | Deposited line | Deposited line | Deposited line | Deposited line | Deposited line |
|---|---|---|---|---|---|---|---|---|---|---|---|
| SNP180 | 8 | 45.635 | 36966286 | T | C | B | B | B | B | B | B |
| SNP181 | 8 | 49.698 | 37687701 | C | G | A | A | A | A | A | A |
| SNP182 | 8 | 53.908 | 38577262 | C | A | A | A | A | A | A | A |
| SNP183 | 8 | 62.287 | 40758807 | G | A | B | B | B | B | B | B |
| SNP184 | 8 | 62.374 | 40785808 | G | T | A | A | A | A | A | A |
| SNP185 | 9 | 0.030 | 313527 | G | C | A | A | A | A | A | A |
| SNP186 | 9 | 0.104 | 330755 | C | T | B | B | B | B | B | B |
| SNP187 | 9 | 0.183 | 340706 | G | A | B | B | B | B | B | B |
| SNP188 | 9 | 1.079 | 455157 | C | T | B | B | B | B | B | B |
| SNP189 | 9 | 7.242 | 1254086 | G | A | B | B | B | B | B | B |
| SNP190 | 9 | 10.178 | 1639986 | C | T | B | B | B | B | B | B |
| SNP191 | 9 | 15.497 | 2355085 | C | T | A | A | A | A | A | A |
| SNP192 | 9 | 26.071 | 3745424 | C | G | B | B | B | B | B | B |
| SNP193 | 9 | 30.177 | 4464952 | C | T | A | A | A | A | A | A |
| SNP194 | 9 | 32.759 | 5079336 | A | C | A | A | A | A | A | A |
| SNP195 | 9 | 41.524 | 7839999 | C | A | B | B | B | B | B | B |
| SNP196 | 9 | 45.092 | 9246116 | C | T | B | B | B | B | B | B |

TABLE 4G-continued

| SNP ID | Chr | cM | Location of SNPs on chromosomes | | | | | | | | |
|---|---|---|---|---|---|---|---|---|---|---|---|
| SNP197 | 9 | 53.464 | 17031088 | T | G | B | B | B | B | B | B |
| SNP198 | 9 | 58.238 | 42755363 | G | A | A | A | A | A | A | A |
| SNP199 | 9 | 60.841 | 44984162 | G | A | A | A | A | A | A | A |
| SNP200 | 9 | 69.310 | 48249783 | C | T | B | B | B | B | B | B |
| SNP201 | 9 | 70.587 | 48542186 | C | T | B | B | B | B | B | B |
| SNP202 | 9 | 73.370 | 49125336 | C | G | B | B | B | B | B | B |
| SNP203 | 9 | 77.936 | 50007823 | G | T | A | A | A | A | A | A |
| SNP204 | 9 | 82.039 | 50576467 | C | T | A | A | A | A | A | A |
| SNP205 | 9 | 95.733 | 51845327 | G | T | A | A | A | A | A | A |
| SNP206 | 9 | 100.571 | 52317409 | G | A | B | B | B | B | B | B |
| SNP207 | 9 | 106.361 | 53047247 | T | C | A | A | A | A | A | A |
| SNP208 | 9 | 111.615 | 54261547 | A | T | A | A | A | A | A | A |
| SNP209 | 9 | 112.468 | 54570013 | G | A | A | A | A | A | A | A |

| SNP ID | Chr | cM | Location of SNPs on chromosomes | Deposited line | SHASTA | ERUDE | HAITSU SP | FOREST | TBR-449 | CASTLE | GREEN FACE |
|---|---|---|---|---|---|---|---|---|---|---|---|
| SNP180 | 8 | 45.635 | 36966286 | B | A | B | B | H | A | A | B |
| SNP181 | 8 | 49.698 | 37687701 | A | B | H | A | H | B | B | A |
| SNP182 | 8 | 53.908 | 38577262 | A | A | A | A | A | H | A | H |
| SNP183 | 8 | 62.287 | 40758807 | B | H | B | B | B | B | H | H |
| SNP184 | 8 | 62.374 | 40785808 | A | H | H | A | H | H | B | A |
| SNP185 | 9 | 0.030 | 313527 | A | H | B | H | H | A | H | H |
| SNP186 | 9 | 0.104 | 330755 | B | H | A | H | B | B | H | B |
| SNP187 | 9 | 0.183 | 340706 | B | B | B | H | H | B | B | H |
| SNP188 | 9 | 1.079 | 455157 | B | H | B | H | H | B | B | H |
| SNP189 | 9 | 7.242 | 1254086 | B | B | B | B | H | B | A | B |
| SNP190 | 9 | 10.178 | 1639986 | B | A | H | A | H | H | H | A |
| SNP191 | 9 | 15.497 | 2355085 | A | A | B | H | H | B | H | H |
| SNP192 | 9 | 26.071 | 3745424 | B | H | B | H | H | B | H | H |
| SNP193 | 9 | 30.177 | 4464952 | A | B | H | B | B | H | B | A |
| SNP194 | 9 | 32.759 | 5079336 | A | A | H | H | A | A | A | A |
| SNP195 | 9 | 41.524 | 7839999 | B | H | B | H | B | B | H | B |
| SNP196 | 9 | 45.092 | 9246116 | B | B | B | B | B | B | H | B |
| SNP197 | 9 | 53.464 | 17031088 | B | A | B | B | H | B | H | B |
| SNP198 | 9 | 58.238 | 42755363 | A | A | A | A | A | H | A | A |
| SNP199 | 9 | 60.841 | 44984162 | A | A | A | A | H | A | H | A |
| SNP200 | 9 | 69.310 | 48249783 | B | H | B | B | B | B | H | B |
| SNP201 | 9 | 70.587 | 48542186 | B | B | B | B | B | B | H | B |
| SNP202 | 9 | 73.370 | 49125336 | B | B | H | B | B | H | B | H |
| SNP203 | 9 | 77.936 | 50007823 | A | H | A | H | B | A | B | A |
| SNP204 | 9 | 82.039 | 50576467 | A | A | H | B | H | A | A | A |
| SNP205 | 9 | 95.733 | 51845327 | A | B | H | H | A | H | A | H |
| SNP206 | 9 | 100.571 | 52317409 | B | H | B | H | H | B | H | H |
| SNP207 | 9 | 106.361 | 53047247 | A | A | H | H | A | B | A | H |
| SNP208 | 9 | 111.615 | 54261547 | A | B | B | A | A | B | A | B |
| SNP209 | 9 | 112.468 | 54570013 | A | B | H | H | H | B | A | B |

| SNP ID | Chr | cM | Location of SNPs on chromosomes | MEGA-DOME | PIXEL | SK9-099 | GREEN CANNON | GRAN-DOME | HEART-LAND | DES-TINY | Gypsy |
|---|---|---|---|---|---|---|---|---|---|---|---|
| SNP180 | 8 | 45.635 | 36966286 | A | A | H | H | H | A | H | A |
| SNP181 | 8 | 49.698 | 37687701 | B | B | H | H | H | B | H | H |
| SNP182 | 8 | 53.908 | 38577262 | A | B | H | H | H | A | A | H |
| SNP183 | 8 | 62.287 | 40758807 | H | H | A | H | H | B | H | A |
| SNP184 | 8 | 62.374 | 40785808 | B | A | B | A | H | B | A | A |
| SNP185 | 9 | 0.030 | 313527 | B | H | B | A | B | A | B | H |
| SNP186 | 9 | 0.104 | 330755 | A | H | A | B | A | B | A | H |
| SNP187 | 9 | 0.183 | 340706 | B | B | B | B | B | B | B | B |
| SNP188 | 9 | 1.079 | 455157 | B | B | B | B | B | B | B | B |
| SNP189 | 9 | 7.242 | 1254086 | A | H | B | B | B | A | H | B |
| SNP190 | 9 | 10.178 | 1639986 | A | A | H | H | B | B | H | A |
| SNP191 | 9 | 15.497 | 2355085 | A | H | B | B | B | B | H | B |
| SNP192 | 9 | 26.071 | 3745424 | H | H | B | B | B | B | H | H |
| SNP193 | 9 | 30.177 | 4464952 | B | B | H | H | A | B | H | H |
| SNP194 | 9 | 32.759 | 5079336 | A | A | A | A | A | A | A | A |
| SNP195 | 9 | 41.524 | 7839999 | B | B | B | B | B | A | B | H |
| SNP196 | 9 | 45.092 | 9246116 | H | B | B | B | B | B | B | B |
| SNP197 | 9 | 53.464 | 17031088 | H | H | H | H | B | A | H | H |
| SNP198 | 9 | 58.238 | 42755363 | A | H | A | A | A | A | A | H |
| SNP199 | 9 | 60.841 | 44984162 | A | A | A | A | A | A | A | B |
| SNP200 | 9 | 69.310 | 48249783 | H | B | B | B | B | A | B | B |
| SNP201 | 9 | 70.587 | 48542186 | A | B | B | B | B | B | B | B |
| SNP202 | 9 | 73.370 | 49125336 | B | B | B | H | B | B | B | B |
| SNP203 | 9 | 77.936 | 50007823 | B | H | B | H | H | B | H | H |
| SNP204 | 9 | 82.039 | 50576467 | A | A | A | A | A | A | A | A |

TABLE 4G-continued

| SNP ID | Chr | cM | Location of SNPs on chromosomes | | | | | | | | |
|---|---|---|---|---|---|---|---|---|---|---|---|
| SNP205 | 9 | 95.733 | 51845327 | H | H | H | A | A | A | A | B |
| SNP206 | 9 | 100.571 | 52317409 | B | B | H | B | B | B | B | H |
| SNP207 | 9 | 106.361 | 53047247 | A | H | H | H | B | A | H | H |
| SNP208 | 9 | 111.615 | 54261547 | A | H | H | H | H | A | H | H |
| SNP209 | 9 | 112.468 | 54570013 | A | H | A | H | H | A | H | H |

| SNP ID | Chr | cM | Location of SNPs on chromosomes | Emerald Crown | Marathon | Avenger | Imperial | SUBARU | FIGHTER | IMIDORI 96 | DOME 052 | IRON-MAN |
|---|---|---|---|---|---|---|---|---|---|---|---|---|
| SNP180 | 8 | 45.635 | 36966286 | A | H | H | A | H | A | A | A | H |
| SNP181 | 8 | 49.698 | 37687701 | B | H | H | B | H | B | B | B | H |
| SNP182 | 8 | 53.908 | 38577262 | B | H | H | H | A | H | A | A | H |
| SNP183 | 8 | 62.287 | 40758807 | A | B | H | A | H | A | A | H | B |
| SNP184 | 8 | 62.374 | 40785808 | H | A | H | H | A | B | B | H | A |
| SNP185 | 9 | 0.030 | 313527 | B | H | B | H | B | B | H | B | B |
| SNP186 | 9 | 0.104 | 330755 | A | H | A | H | A | A | H | A | H |
| SNP187 | 9 | 0.183 | 340706 | B | B | B | B | B | B | B | B | H |
| SNP188 | 9 | 1.079 | 455157 | B | B | B | B | B | B | B | B | B |
| SNP189 | 9 | 7.242 | 1254086 | H | B | B | H | H | H | A | H | B |
| SNP190 | 9 | 10.178 | 1639986 | A | H | H | A | H | H | H | H | H |
| SNP191 | 9 | 15.497 | 2355085 | H | B | B | H | H | B | H | A | B |
| SNP192 | 9 | 26.071 | 3745424 | H | B | B | H | H | B | H | H | B |
| SNP193 | 9 | 30.177 | 4464952 | H | H | A | H | H | H | B | H | H |
| SNP194 | 9 | 32.759 | 5079336 | A | A | A | H | A | A | A | A | A |
| SNP195 | 9 | 41.524 | 7839999 | B | B | B | B | B | H | H | B | H |
| SNP196 | 9 | 45.092 | 9246116 | B | B | B | B | B | B | H | B | B |
| SNP197 | 9 | 53.464 | 17031088 | H | B | B | B | H | H | H | H | H |
| SNP198 | 9 | 58.238 | 42755363 | A | H | A | A | A | A | A | A | A |
| SNP199 | 9 | 60.841 | 44984162 | A | A | A | H | A | A | A | H | A |
| SNP200 | 9 | 69.310 | 48249783 | B | B | B | B | B | B | A | H | B |
| SNP201 | 9 | 70.587 | 48542186 | B | B | B | B | B | B | A | H | B |
| SNP202 | 9 | 73.370 | 49125336 | B | B | B | H | B | B | B | B | B |
| SNP203 | 9 | 77.936 | 50007823 | B | A | H | H | H | B | B | B | B |
| SNP204 | 9 | 82.039 | 50576467 | A | A | A | A | A | A | A | A | A |
| SNP205 | 9 | 95.733 | 51845327 | A | H | A | H | A | A | A | A | A |
| SNP206 | 9 | 100.571 | 52317409 | B | B | B | H | B | B | B | H | B |
| SNP207 | 9 | 106.361 | 53047247 | H | B | B | H | H | A | A | A | H |
| SNP208 | 9 | 111.615 | 54261547 | A | B | H | H | H | A | A | A | H |
| SNP209 | 9 | 112.468 | 54570013 | A | B | H | H | H | A | A | H | B |

While the present invention has been described above with reference to embodiments and examples, the present invention is by no means limited thereto. Various changes and modifications that may become apparent to those skilled in the art may be made in the configuration and specifics of the present invention without departing from the scope of the present invention.

SUPPLEMENTARY NOTES

Some or all of the above example embodiments and examples may be described as in the following Supplementary Notes, but are not limited thereto.
(Supplementary Note 1)
A broccoli plant including a broccoli plant identified by Accession No. FERM BP-22393 or a progeny line thereof
(Supplementary Note 2)
The broccoli plant according to Supplementary Note 1, wherein
    the progeny line has 50% or more allele of the broccoli plant identified by Accession No. FERM BP-22393.
(Supplementary Note 3)
The broccoli plant according to Supplementary Note 1 or 2, wherein
    the progeny line has 50% or more allele of the broccoli plant identified by Accession No. FERM BP-22393, and
    the progeny line has the following characteristics (1) through (10):
(1) anthocyanin coloration of leaf blade: absent;
(2) anthocyanin coloration of petiole: absent;
(3) intensity of anthocyanin coloration of head: weak;
(4) number of leaves: many;
(5) length of stem: short;
(6) firmness of head: firm;
(7) number of lobes: many;
(8) depth of lobe: deep;
(9) time of harvest: late; and
(10) self-incompatibility gene: SRK[18] gene and SLG[18] gene.
(Supplementary Note 4)
The broccoli plant according to any one of Supplementary Notes 1 to 3, wherein
    the progeny line has 50% or more allele of the broccoli plant identified by Accession No. FERM BP-22393, and
    the progeny line has at least one SNP selected from the group consisting of SNP7, SNP8, SNP20, SNP21, SNP75, SNP78, SNP81, SNP84, SNP90, SNP142, SNP165, and SNP177.
(Supplementary Note 5)
The broccoli plant according to any one of Supplementary Notes 1 to 4, wherein
    the broccoli plant is a plant body or a part thereof
(Supplementary Note 6)
The broccoli plant according to any one of Supplementary Notes 1 to 5, wherein
    the broccoli plant is a seed.
(Supplementary Note 7)
A method for producing a broccoli plant, including the step of:
    crossing a first broccoli plant with a second broccoli plant, wherein the first broccoli plant is the broccoli plant according to any one of Supplementary Notes 1 to 6.
(Supplementary Note 8)
A seed of a broccoli variety Takii 12, wherein
   a typical sample is a seed of a broccoli plant deposited under Accession No. FERM BP-22393.
(Supplementary Note 9)
A broccoli plant of a broccoli variety Takii 12, wherein
   a typical sample is a seed of a broccoli plant deposited under Accession No. FERM BP-22393.
(Supplementary Note 10)
A broccoli plant or a part thereof, having essentially all physiological and morphological characteristics of the broccoli plant according to Supplementary Note 9.
(Supplementary Note 11)
A progeny broccoli plant of the broccoli plant according to Supplementary Note 9, having at least 50% allele of the broccoli plant according to Supplementary Note 9, wherein
   the progeny broccoli plant has the following characteristics (1) through (10):
(1) anthocyanin coloration of leaf blade: absent;
(2) anthocyanin coloration of petiole: absent;
(3) intensity of anthocyanin coloration of head: weak;
(4) number of leaves: many;
(5) length of stem: short;
(6) firmness of head: firm;
(7) number of lobes of leaf: many;
(8) depth of lobe of leaf: deep;
(9) time of harvest: late; and
(10) self-incompatibility gene: $SRK^{18}$ gene and $SLG^{18}$ gene.
(Supplementary Note 12)
A seed for production of the broccoli plant according to Supplementary Note 11.
(Supplementary Note 13)
A progeny broccoli plant of the broccoli plant according to Supplementary Note 9, wherein
   the progeny broccoli plant has at least 50% allele of the broccoli plant, according to Supplementary Note 9, and
   the progeny broccoli plant has at least one SNP selected from the group consisting of SNP7, SNP8, SNP20, SNP21, SNP75, SNP78, SNP81, SNP84, SNP90, SNP142, SNP165, and SNP177.
(Supplementary Note 14)
A seed for production of the broccoli plant according to Supplementary Note 13.
(Supplementary Note 15)
A plant part of the broccoli plant according to Supplementary Note 9.
(Supplementary Note 16)
The plant part according to Supplementary Note 15, wherein
   the plant part includes microspores, pollens, ovaries, ovules, embryonic sacs, egg cells, cuttings, roots, trunks, leaves, cells, or protoplasts.
(Supplementary Note 17)
A method for producing a broccoli seed, including the step of:
   self-crossing the broccoli plant according to Supplementary Note 9, or crossing the broccoli plant according to Supplementary Note 9 with another broccoli plant, and
   collecting (gathering) a resulting seed(s).
(Supplementary Note 18)
A broccoli seed derived from a broccoli plant produced by the method according to Supplementary Note 17.
(Supplementary Note 19)
A broccoli plant or a part thereof produced by growing the broccoli seed according to Supplementary Note 18.

(Supplementary Note 20)
The broccoli plant or the part thereof according to Supplementary Note 19, having at least 50% allele of a broccoli variety Takii 12 whose typical sample is a seed of a broccoli plant deposited under Accession No. FERM BP-22393, wherein
   the broccoli plant or the part thereof has the following characteristics (1) through (10):
(1) anthocyanin coloration of leaf blade: absent;
(2) anthocyanin coloration of petiole: absent;
(3) intensity of anthocyanin coloration of head: weak;
(4) number of leaves: many;
(5) length of stem: short;
(6) firmness of head: firm;
(7) number of lobes: many;
(8) depth of lobe: deep;
(9) time of harvest: late; and
(10) self-incompatibility gene: $SRK^{18}$ gene and $SLG^{18}$ gene.
(Supplementary Note 21)
The broccoli plant or the part thereof according to Supplementary Note 19, having at least 50% allele of a broccoli variety Takii 12 whose typical sample is a seed of a broccoli plant deposited under Accession No. FERM BP-22393, wherein
   the broccoli plant or the part thereof has at least one SNP selected from the group consisting of SNP7, SNP8, SNP20, SNP21, SNP75, SNP78, SNP81, SNP84, SNP90, SNP142, SNP165, and SNP177.
(Supplementary Note 22)
The broccoli plant or the part thereof according to Supplementary Note 19, having essentially all physiological and morphological characteristics of a broccoli variety Takii 12 whose typical sample is a seed of a broccoli plant deposited under Accession No. FERM BP-22393.
(Supplementary Note 23)
The broccoli plant or the part thereof according to Supplementary Note 20, wherein
   one or more characteristics have been modified.
(Supplementary Note 24)
The broccoli plant or the part thereof according to Supplementary Note 23, wherein
   the modification is performed by mutagenesis.
(Supplementary Note 25)
A method for producing a seed of a broccoli plant derived from the broccoli plant according to Supplementary Note 9, including the steps of:
   (a) crossing a broccoli variety Takii 12, which is a seed of a broccoli plant deposited under Accession No. FERM BP-22393, with another broccoli plant to produce a seed;
   (b) growing a broccoli plant from the seed obtained in step (a) to produce a broccoli plant derived from the broccoli variety Takii 12;
   (c) self-crossing the broccoli plant obtained in step (b) or crossing the broccoli plant obtained in step (b) with another broccoli plant to produce an additional broccoli plant derived from the broccoli variety Takii 12; and
   (d) optionally repeating steps (b) and (c) one or more times to further produce a broccoli plant(s) derived from the broccoli variety Takii 12, wherein the broccoli plant in step (b) has been grown from the additional broccoli plant obtained in step (c).
(Supplementary Note 26)
A seed produced by the method according to Supplementary Note 25, having at least 50% allele of the broccoli plant according to Supplementary Note 9, wherein
   the broccoli plant grown from the seed has the following characteristics (1) through (10):

(1) anthocyanin coloration of leaf blade: absent;
(2) anthocyanin coloration of petiole: absent;
(3) intensity of anthocyanin coloration of head: weak;
(4) number of leaves: many;
(5) length of stem: short;
(6) firmness of head: firm;
(7) number of lobes: many;
(8) depth of lobe: deep;
(9) time of harvest: late; and
(10) self-incompatibility gene: SRK$^{18}$ gene and SLG$^{18}$ gene.

(Supplementary Note 27)
A broccoli plant produced by growing the seed of the broccoli plant according to Supplementary Note 26.

(Supplementary Note 28)
A seed produced by the method according to Supplementary Note 25, having at least 50% allele of the broccoli plant according to Supplementary Note 9, wherein
the broccoli plant grown from the seed has at least one SNP selected from the group consisting of SNP7, SNP8, SNP20, SNP21, SNP75, SNP78, SNP81, SNP84, SNP90, SNP142, SNP165, and SNP177.

(Supplementary Note 29)
A broccoli plant produced by growing the seed of the broccoli plant according to Supplementary Note 28.

(Supplementary Note 30)
A method for introducing at least one new characteristic into the broccoli plant according to Supplementary Note 9, including the steps of:
(a) crossing a broccoli variety Takii 12, which is a seed of a broccoli plant deposited under Accession No. FERM BP-22393, with a broccoli plant having at least one new characteristic to produce a progeny(s);
(b) selecting a progeny having at least one new characteristic;
(c) crossing the progeny with the broccoli variety Takii 12 to produce a backcross progeny(s);
(d) selecting a backcross progeny having at least one new characteristic and having essentially all physiological and morphological characteristics of the broccoli variety Takii 12; and
(e) optionally repeating steps (c) and (d) one or more times to produce a broccoli plant(s) having at least one new characteristic and having essentially all physiological and morphological characteristics of the broccoli variety Takii 12, wherein the broccoli plant in step (c) is a backcross progeny that has been selected in step (d).

(Supplementary Note 31)
A broccoli plant produced by the method according to Supplementary Note 30.

(Supplementary Note 32)
A method for producing a broccoli plant derived from a broccoli variety Takii 12 having at least one new characteristic, including the step of:
transferring a mutation or a transgene that imparts at least one characteristic into a broccoli variety Takii 12, which is a seed of a broccoli plant deposited under Accession No. FERM BP-22393.

(Supplementary Note 33)
A broccoli plant produced by the method according to Supplementary Note 32.

(Supplementary Note 34)
A method for producing a flower head of a broccoli as a food, including the step of:
harvesting a flower head or the flower head and a peduncle of the broccoli plant according to Supplementary Note 9.

(Supplementary Note 35)
A processed product of the broccoli plant according to Supplementary Note 9, including:
a cut, sliced, ground, pureed, dried, canned, bottled, washed, packaged, frozen and/or heat-treated flower head.

(Supplementary Note 36)
A method for determining a genotype of the broccoli plant according to Supplementary Note 9 or a progeny line thereof, including the steps of:
(a) obtaining a nucleic acid sample from the broccoli plant according to Supplementary Note 9 or a progeny line thereof, and
(b) detecting a polymorphism in the nucleic acid sample.

(Supplementary Note 37)
A tissue culture of regenerable cells or protoplasts derived from the broccoli plant according to Supplementary Note 9.

(Supplementary Note 38)
The culture tissue according to Supplementary Note 37, wherein
the cells or protoplasts are derived from leaves, pollens, embryos, cotyledons, hypocotyls, meristematic cells, roots, root tips, anthers, flowers, seeds, or stems.

(Supplementary Note 39)
A broccoli plant regenerated from the tissue culture according to Supplementary Note 38.

(Supplementary Note 40)
The broccoli plant according to Supplementary Note 39, having essentially all physiological and morphological characteristics of a broccoli variety Takii 12, which is a seed of a broccoli plant deposited under Accession No. FERM BP-22393.

(Supplementary Note 41)
A method for vegetative propagation of the broccoli plant according to Supplementary Note 9, including the steps of:
(a) collecting a propagatable tissue from a broccoli plant of a broccoli variety Takii 12, which is a seed of a broccoli plant deposited under Accession No. FERM BP-22393;
(b) culturing the tissue to obtain a grown shoot;
(c) rooting the grown shoot to obtain a rooted plantlet; and
(d) optionally growing a plant from the rooted plantlet.

(Supplementary Note 42)
A broccoli plantlet or a plant produced by the method according to Supplementary Note 41, having essentially all physiological and morphological characteristics of a broccoli variety Takii 12, which is a seed of a broccoli plant deposited under Accession No. FERM BP-22393.

(Supplementary Note 43)
A broccoli plant including a broccoli plant identified by Accession No. FERM BP-22393.

(Supplementary Note 44)
A broccoli plant including a progeny line of the broccoli plant according to Supplementary Note 43, wherein
the progeny line has the following characteristics (1) through (10):
(1) anthocyanin coloration of leaf blade: absent;
(2) anthocyanin coloration of petiole: absent;
(3) intensity of anthocyanin coloration of head: weak;
(4) number of leaves: many;
(5) length of stem: short;
(6) firmness of head: firm;
(7) number of lobes: many;
(8) depth of lobe: deep;
(9) time of harvest: late; and
(10) self-incompatibility gene: SRK$^{18}$ gene and SLG$^{18}$ gene.

(Supplementary Note 45)
A broccoli plant including:
  a hybrid first-generation line of the broccoli plant according to Supplementary Note 43 or 44.
(Supplementary Note 46)
The broccoli plant according to any one of Supplementary Notes 43 to 45, wherein
  the broccoli plant is a plant body or a part thereof
(Supplementary Note 47)
The broccoli plant according to any one of Supplementary Notes 43 to 46, wherein
  the broccoli plant is a seed.
(Supplementary Note 48)
A method for producing a broccoli plant, including the step of:
  self-crossing the broccoli plant according to any one of Supplementary Notes 43 to 47.
(Supplementary Note 49)
A method for producing a broccoli plant, including the step of:
  crossing the broccoli plant according to any one of Supplementary Notes 43 to 47 with another broccoli plant.
(Supplementary Note 50)
The method for producing a broccoli plant according to Supplementary Note 48 or 49, including the step of:
  gathering a seed(s).

INDUSTRIAL APPLICABILITY

As described above, according to the present invention, a new broccoli plant can be provided. For this reason, the present invention is extremely useful in an agricultural field such as breeding, for example.

What is claimed is:

1. A hybrid broccoli plant, having as a parent plant broccoli variety Takii 12, a sample seed of variety Takii 12 having been deposited under Accession No. FERM BP-22393, wherein the hybrid broccoli plant has at least 50% or more alleles of the plant of broccoli variety Takii 12.

2. The hybrid broccoli plant according to claim 1, wherein the hybrid broccoli plant contains:
   a. anthocyanin coloration of leaf blade: absent;
   b. anthocyanin coloration of petiole: absent;
   c. intensity of anthocyanin coloration of head: weak;
   d. number of leaves: many;
   e. length of stem: short;
   f. firmness of head: firm;
   g. number of lobes: many;
   h. depth of lobe: deep;
   i. time of harvest: late; and
   j. self-incompatibility gene: SRK$^{18}$ gene and SLG$^{18}$ gene.

3. The hybrid broccoli plant according to claim 1, wherein the hybrid broccoli plant comprises at least one SNP selected from the group consisting of SNP7, SNP8, SNP20, SNP21, SNP75, SNP78, SNP81, SNP84, SNP90, SNP142, SNP165, and SNP177.

4. An inbred broccoli seed of a broccoli variety designated Takii 12, a sample of the seed having been deposited under Accession No. FERM BP-22393.

5. A broccoli plant, or part thereof, wherein the plant is an inbred broccoli plant grown from the broccoli variety Takii 12, a representative seed sample of the variety deposited under Accession No. FERM BP-22393.

6. The plant part according to claim 5, wherein the plant part is selected from the group consisting of microspores, pollens, ovaries, ovules, embryonic sacs, egg cells, cuttings, roots, trunks, leaves, cells, and protoplasts.

7. A method for producing a broccoli seed, comprising the steps of:
   a. collecting seed resulting in self-crossing the broccoli plant according to claim 5; or
   b. collecting seed resulting in crossing the broccoli plant according to claim 5 with another broccoli plant.

8. An F1 broccoli seed obtained from a broccoli plant produced by the method according to claim 7.

9. An F1 broccoli plant produced by growing the broccoli seed according to claim 8, wherein the F1 broccoli plant has all the morphological and physiological characteristics of broccoli variety Takii 12, a representative seed sample of the variety deposited under Accession No. FERM BP-22393.

10. A method for producing a seed of a broccoli plant derived from the broccoli plant according to claim 5, comprising the steps of:
    (a) crossing a broccoli variety Takii 12, with another broccoli plant to produce a seed;
    (b) growing a broccoli plant from the seed obtained in step (a) to produce a broccoli plant derived from the broccoli variety Takii 12;
    (c) self-crossing the broccoli plant obtained in step (b) or crossing the broccoli plant obtained in step (b) with another broccoli plant to produce an additional broccoli plant derived from the broccoli variety Takii 12; and (d) repeating steps (b) and (c) two or more times to further produce a broccoli plant(s) derived from the broccoli variety Takii 12, wherein the broccoli plant in step (b) has been grown from the additional broccoli plant obtained in step (c).

11. A seed produced by the method according to claim 10.

12. A broccoli plant produced by growing the seed of the broccoli plant according to claim 11, having all the morphological and physiological characteristics of a broccoli plant of a broccoli variety Takii 12, a representative seed sample of the variety deposited under Accession No. FERM BP-22393.

13. A seed produced by the method according to claim 10, wherein the broccoli plant grown from the seed has at least one SNP selected from the group consisting of SNP7, SNP8, SNP20, SNP21, SNP75, SNP78, SNP81, SNP84, SNP90, SNP142, SNP165, and SNP177.

14. A broccoli plant produced by growing the seed of the broccoli plant according to claim 13, having all the morphological and physiological characteristics of a broccoli plant of a broccoli variety Takii 12, a representative seed sample of the variety deposited under Accession No. FERM BP-22393.

15. A method for introducing at least one new morphological or physiological characteristic into the broccoli plant according to claim 5, comprising the steps of:
(a) crossing a broccoli variety Takii 12, which is a seed of a broccoli plant deposited under Accession No. FERM BP-22393, with a broccoli plant having at least one new characteristic to produce a progeny(s);
(b) selecting a progeny having at least one new characteristic;
(c) crossing the progeny with the broccoli variety Takii 12 to produce a backcross progeny(s);
(d) selecting a backcross progeny having at least one new characteristic and having all physiological and morphological characteristics of the broccoli variety Takii 12; and
(e) repeating steps (c) and (d) two or more times to produce a broccoli plant(s) having at least one new characteristic and having all physiological and morphological characteristics of the broccoli variety Takii 12, wherein the broccoli plant in step (c) is a backcross progeny that has been selected in step (d).

16. A broccoli plant produced by the method according to claim 15, wherein the broccoli plant has all the morphological and physiological characteristics of a broccoli plant of a broccoli variety Takii 12, and at least one new morphological or physiological characteristic.

17. A method for producing a broccoli plant obtained from a broccoli variety Takii 12 having at least one new characteristic, comprising the step of:
transferring a transgene that imparts at least one new characteristic into a broccoli variety Takii 12, a representative seed sample of the variety deposited under Accession No. FERM BP-22393.

18. A method for producing a flower head of a broccoli as a food, comprising the step of:
harvesting a flower head or the flower head and a peduncle of the broccoli plant according to claim 5.

19. A processed product of the broccoli plant according to claim 5, comprising:
a cut, sliced, ground, pureed, dried, canned, bottled, washed, packaged, frozen and/or heat-treated flower head.

20. A method for determining a genotype of the broccoli plant according to claim 5 or an inbred progeny line thereof, comprising the steps of:
(a) obtaining a nucleic acid sample from the broccoli plant according to claim 5 or an inbred progeny line thereof, and
(b) detecting a polymorphism in the nucleic acid sample.

21. A tissue culture of regenerable cells or protoplasts derived from the broccoli plant according to claim 5.

22. The culture tissue according to claim 21, wherein
the cells or protoplasts are derived from leaves, pollens, embryos, cotyledons, hypocotyls, meristematic cells, roots, root tips, anthers, flowers, seeds, and stems.

23. A broccoli plant regenerated from the tissue culture according to claim 22, wherein the broccoli plant has all the morphological and physiological characteristics of a broccoli plant of the broccoli variety Takii 12, and at least one new morphological or physiological characteristic.

24. A method for vegetative propagation of the broccoli plant according to claim 5, comprising the steps of:
(a) collecting a propagatable tissue from a broccoli plant of a broccoli variety Takii 12, which is a seed of a broccoli plant deposited under Accession No. FERM BP-22393;
(b) culturing the tissue to obtain a grown shoot;
(c) rooting the grown shoot to obtain a rooted plantlet; and
(d) growing a plant from the rooted plantlet.

25. A broccoli plantlet or a plant produced by the method according to claim 24, having all physiological and morphological characteristics of a broccoli variety Takii 12, which is a seed of a broccoli plant deposited under Accession No. FERM BP-22393.

* * * * *

```
                          SEQUENCE LISTING

<160> NUMBER OF SEQ ID NOS: 211

<210> SEQ ID NO 1
    <211> LENGTH: 2685
    <212> TYPE: DNA
    <213> ORGANISM: Brassica oleracea

<400> SEQUENCE: 1
atgaaaggtg tacgaaacat ctatcaccat tcttacacct ccttgttgct cgtctacgtt      60
gtcatgattc tatttcatcc tggccttgcg atctatatca ccactttgtc ggctacagaa     120
tctcttacaa tctcaagcaa cagaacactt gtatctcccg gcaatgtctt cgagctcggt     180
ttcttcaaaa ccacctcaag ttcccgttgg tatctcggga tatggtacaa gaaattgccc     240
gacagaacct atgtatggat tgccaacaga gataaccctc tccccaatac cattggaacc     300
ctcaaaatct caggcaataa tcttgtcatc cttggtcatt ccaataaatc tgtttggtcg     360
acgaatgtaa ctagaggaaa tgagagatct ccggtggtgg cagagcttct cgctaacgga     420
aacttcgtga tgcgagactc caataacaca gacgcaaatg aattcttgtg gcaaagtttc     480
gatttcccta caaatacttt gcttccagag atgaaactgg gttacgacct caaaacaggg     540
ctgaacaggt tccttacatc atggagaggt tcagatgatc cgtcaagcgg ggatcacttg     600
tacaagctcg aaccccgaag ttttcctgaa ttttatatat ttaacgacga ctttccagtg     660
catcggattg gtccatggaa tggaatcgaa tttagtggca taccagagga ccagaagtcg     720
agttacatgg tgtacaattt cacagagaat agtgaggagg ttgcttattc atttcgaatg     780
accaacaaca gcatttactc gagattgata ataagttccg aagggtattt acagcgactg     840
atatggactc cgtcaacaaa gatatggcaa gagttctggt cttctccagt gagcctccag     900
tgcgatccat acaggatttg tgggccttac gcttactgtg acgagaacac atcaccggtg     960
tgtaactgta tacaagggtt cgatcccaag aaccagcagc agtgggatct gagatcccat    1020
gcaagtgggt gtataaggag gacgtggctg agctgccgtg tgatggtttt acaaggatg    1080 aagaatatga agttgccaga cactacggcg gcgattgtcg accggagtgt tggtgtgaaa    1140
gaatgtgaga agaaatgcct tagcaattgt aattgtactg catttgcaaa tgcggatatc    1200
cggaatggtg ggacgggttg tgtgatttgg accggggagc ttgaagatat ccggaattac    1260
gttgctgacg gtcaagatct ttatgtcaga ttagctgctg ctgatctcgt taagaagaga    1320
aactcgaatg ggaaaatcat aggtttgatt gttggagtta gtgttctgct tcttctaata    1380
atttcctgcc tctggaaaag gagacaaaag cgagcaaaag caagtgcaac atctattgca    1440
```

| | |
|---|---|
| aatcgacaga gaaaccaaaa tatgcctatg aacgggatgg tgctatcaag caagagacag | 1500 |
| ttgtctggag agaacaaaat tgaggatttg aacttccat tgatagagtt ggaagctgtt | 1560 |
| gtcaaagcca ccgaaaattt ctccagttgt aataaaatcg gagaaggtgg ttttggtatt | 1620 |
| gtttacaagg gaagattact tgatgggcaa gaaatcgcgg taaaaaggct atcaaagacg | 1680 |
| tcatttcaag ggactgatga gtttatgaat gaggtgacat taatcgcaag gcttcagcat | 1740 |
| ataaaccttg ttcaagttct tggctgttgc attgaaggag atgagaaaat gctgatatat | 1800 |
| gagtatttgg aaaatttaag cctcgattct tatctcttcg gaaaaacccg aagctctaag | 1860 |
| ctaagttgga aggagagatt cgacattacc aatggtgttg ctcgagggct tttatatcta | 1920 |
| catcaagact cacgatttag gataatccac agagatttga agtaagtaa cattttgctt | 1980 |
| gataaaaata tgatcccaaa gatctcggat tttgggatgg ccagaatatt tgcaagggat | 2040 |
| gagacggaag caaacacaat gaaggtggtc ggaacttacg gctacatgtc cccagagtat | 2100 |
| gcaatgaatg gatcttctc agaaaaatca gatgttttca gttttggagt catagttctt | 2160 |
| gaaattgtta ctggaaagag gaacagagga ttctacaact tgaactacaa aaacaatttt | 2220 |
| ctaagctatg catggagtaa ttggaaggaa ggaagagcgc tagaaatcgt agatccagtc | 2280 |
| attgtagatt cattgtcacc actgtcatca acatttcaac cacaagaagt cctaaaatgc | 2340 |
| atacaaattg gtctcttgtg tgttcaagaa cttgcagagc acagaccaac gatgtcgact | 2400 |
| gtggtttgga tgcttggaag tgaagcaaca gagattcctc agcctaaacc gccaggttat | 2460 |
| tgcgtcggaa gcagtcctta tgaactagat ccatcagcaa gtaggcagtt ggacgatgat | 2520 |
| gaatcctgga cggtgaacca gtacacttgc tcagtcatcg atgcccggta atatgaacgc | 2580 |
| tgttgaggaa gttcatataa ttaaacatta ctaaatgcag tgactcaata tcatatgtga | 2640 |
| aagaaggaaa taaattctca aaatataagt atgttatttt gtaac | 2685 |

<210> SEQ ID NO 2
<211> LENGTH: 1311
<212> TYPE: DNA
<213> ORGANISM: Brassica oleracea

<400> SEQUENCE: 2

| | |
|---|---|
| atgaaaggcg tgagaaaaac ctacgataat tcttacaccg taaccttttt gcttgtcttt | 60 |
| ttcgtcttga tcctatttcg tcctgccttt tcgatcaaca cgttgtcggc tacagaatct | 120 |
| cttacaatct caagcaacag aacacttgta tctcccggca acgtcttcga gctcggcttc | 180 |
| ttccgaacca ccctcaagtt ctcgttggtat ctcgggatat ggtacaagaa attgcccgac | 240 |
| agaacctatg tatgggttgc caacagagat aaccctctct ccagttccac tggaaccctc | 300 |
| aaaatttcag gcaataatct tgtcatcctt ggccactcca ataaatctgt ttggtcgacg | 360 |
| aatgtaacta gaggaaatga gagatctccg gtggttgcag agcttctcgc taatggaaac | 420 |
| tatgtgatac gagactccaa taacaaggac gcaagtggat tcttgtggca agtttcgat | 480 |
| ttccctacaa atactttgct tccagagatg aaactgggtt acgacctcaa acagggctg | 540 |
| aacaggttcc ttacatcatg gagaggttca gatgatccgt caagcgggga aatcacttac | 600 |
| aagctcgaac cccgaaggtt tcctgagttt atatatttta gcgacgactt ttgagtgcac | 660 |
| cggattggtc catggaatgg aatcggattt agtggcatac cagaggacca gaagtcgagt | 720 |
| tacatggtgt acaatttcac agagaatagt gaggaggttg cttattcatt tcaaatgacc | 780 |
| aacaacagca tttactcgag attgataata acttccgaag ggtatttaca gctactgatg | 840 |

-continued

```
tggactccgt caacaaagat gtggcaagag ttctggtctt ctccagtgag cctccagtgc      900
gatccataca ggatttgtgg gccttgcgct tactgtgacg agaacacatc accggtatgt      960
aactgtatac aagggttcta tcccaagaac cggcagcagt gggatgtgag agtcgcttca     1020
agtgggtgta taaggagaac acggctgagc tgcagtggag atggttttac caggatgaag     1080
aacatgaatt tgccagacac tacaatggcg actgtagaca ggagcattga tgtaaaagaa     1140
tgtaagaaga gatgccttag cgattgtaat tgtaccgctt atgcaaatgc ggatatccgg     1200
aatggtggga cgggttgtgt gatctggacc ggagcgcttg aggacatccg gacttacttt     1260
gctgaaggtc aagatcttta tgtcaaatcg gctgctgctg accttgctta g              1311
```

<210> SEQ ID NO 3
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 3

```
tgacttgtgt cggtggctag aggaaaaggc cccttgtgtcc acaaacgtgt ngtctgtctg      60
ggccattcat ttcaagccca tgtattacgg ttttaattac g                          101
```

<210> SEQ ID NO 4
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 4

```
tttgaaacaa caagcagata acccaaagca acttcttgct gagctaatgg ncatggcatc      60
agctaataag gcaagtgcta gtgacaaggc tgttgctact g                          101
```

<210> SEQ ID NO 5
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 5

```
attctctgtt cttgatcatg cgcttgtgtc ttctattccc tgaaccttca ntggactctt      60
gacctctttt cttaccaaaa caagtaaaat cctcaagaga a                          101
```

<210> SEQ ID NO 6
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 6

```
acgatgtgct ggaggatgga agtgaagtgg aaaatttgtt gaaaaatgcc ncagagaaga      60
cagcagaggc gctgcaggcg aaagacgagt atgagaaaca t                          101
```

<210> SEQ ID NO 7
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 7
tcttgcagcc taatctttcg gctatcccat ggcactcggt gatttggctc naagagagga    60
tacaaaagca cgcttttatt tcatgggtcc ttgtgagaca c                       101

<210> SEQ ID NO 8
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 8
tgagatttgg agctgcagtg atcacagact ctagcgaccg tcggacagcg nttagtagag    60
tgacctattt ctttgcataa ctcacatacc ggtggcatcc a                       101

<210> SEQ ID NO 9
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 9
aagtttggat cggacgcaat cgctgcactg gcggcactaa cgctctcggc natcgaagaa    60
gttgcagcca tctgcagcgg ctgagcgggt aactgtaaac c                       101

<210> SEQ ID NO 10
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 10
aaccggaaca ttccgtagtc tgcagcgtac cagaacttag ctcggttctc ngcaggaaag    60
tagaacatgg tctctgcggg aacaccacac tctcccccag a                       101

<210> SEQ ID NO 11
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 11
tcagcctggc gtctctctcc agctccaagc tgagcccagt tcagcctgaa ngtctgctca    60
caccccggca tttgagcacc attgtaggtc tgcaaaatcc t                          101

<210> SEQ ID NO 12
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 12
tgagaccaag gtcatagagc gagccgaact ctgagtggac agaagaaacc nacatcaaca      60
tcagccaagc gtaactaata gttacaaggt ggatctctgc a                          101

<210> SEQ ID NO 13
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 13
cgtttgggaa atgcgcgatg acgtgatctc gtttgcgttt cttctgcttc ntatctcact      60
cgcatctcga gctcgggcct tcgtctctgc agctgcggga c                          101

<210> SEQ ID NO 14
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 14
tcgttaaatg ctgcagtttc catgccaagc ttctgatctt caaatggtgt ntcgtcaact      60
ttttctaatc gctgaggaag aggcgttggc ataggattgc a                          101

<210> SEQ ID NO 15
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 15
tctccggcaa cagccgatgg acctgtttgc ccaccgacga caaaactaag ncgggcaagt      60
ttccctgaag gtttcctatt tggcacggct actgcagcat a                          101

<210> SEQ ID NO 16
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or A

<400> SEQUENCE: 16
tgtctgagag gcaaaaatgc caagatcaga gtggtgaaaa tgaactattc ntagcacata     60
acaaatgaag tagtcttcta tgaccatcac actatactac a                      101

<210> SEQ ID NO 17
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 17
ctgcagatac agacggagga ttgcgttaga tcgggatcgg gagggagcaa ngagatcgat    60
cggttgccgt ggaaaggagg gagcgagggg aatcctgatt a                      101

<210> SEQ ID NO 18
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 18
tatgtgggag tcattgcttg aaccgcttct gagtcctttg ttgacacact ntcagcgagc    60
tcttgactcc tcgtggacta gtcttctacg ggaaggcagg g                      101

<210> SEQ ID NO 19
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 19
agtacgaccg cacctggttt gaaaatttcc atcactttcc ccatgatggg nttgaacaag    60
agatgatagc tctcgtcgtc gataccatcg tccagtggta c                      101

<210> SEQ ID NO 20
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 20
tccatcactt tccccatgat gggtttgaac aagagatgat agctctcgtc ntcgatacca    60
tcgtccagtg gtacgttgag agaatagtac tttccacttc c                      101

<210> SEQ ID NO 21
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 21
agtcctctgc agcataatca gagtaagcaa agaagagcag gcttggagtg ncgaaagaga    60
tgctctttgg gttctgaatg gttttcatgc ccgtggtgtg a                       101

<210> SEQ ID NO 22
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 22
ataacttcca caatcgctgg tgttgccgtc tctaacgcta acctattcgg nattgcaaac    60
ggaacagcac gaggcggtgt tccctctgct cgaatagcca c                       101

<210> SEQ ID NO 23
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 23
acttccacaa tcgctggtgt tgccgtctct aacgctaacc tattcggtat ngcaaacgga    60
acagcacgag gcggtgttcc ctctgctcga atagccactt a                       101

<210> SEQ ID NO 24
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 24
gaagcgagtg cgatgagtgc aagacctcct acgattgctg ccgtgttctc ngccccatcg    60
gacgaagatc ctgcagtgcc tgagcttatg gcgctctctg c                       101

<210> SEQ ID NO 25
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 25
agtgaagaac cctgcagaga agactcgagt agtttctccg tgtttgcttg ntttgaggcg    60
tttgagagaa gaagaagtgg cggaagcagc tatagaacag t                       101

<210> SEQ ID NO 26
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 26
gctgaaaaac gaactagccg cgatcattgt gaagagggca tcactaaatc ncaatgcagt    60
aaataaagag gttgaagaag ataacatcaa agacattagt g                       101

<210> SEQ ID NO 27
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 27
ttgctgcagc tttgtgagga gagtgtggtg tatcgaacca tggtggcgcg ngaaggtgcg    60
attgctcctg tggtggcttt gtcgcagagt agtaagagtc g                       101

<210> SEQ ID NO 28
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 28
ggaagcacga gttttgcggc tgtggaggac agcatagaca cggtgttggg ngatgcctag    60
ctgggatcgc ctcttgtaga gcgtaggaga ggcaatgagt t                       101

<210> SEQ ID NO 29
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 29
atgacctacg acaagtagac aagatgtgtg tgtccgaaac aggcggctca ngcaagttag    60
ttttcaggaa tgcatcaacc acaacaggtg aggcatatgt t                       101

<210> SEQ ID NO 30
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 30
caccataaaa gctgcagcag cctcttcaac aacaattttt cttcttcctt ncacgatcct    60
ctcctagagg gttctcctac ttctcctctt cttttcaaag a                       101

<210> SEQ ID NO 31
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 31
ctcattgctc gtacactgca aatgttcatg tctctgctcc tgctgtgtcc ngcagatttg     60
tacttctata cggtcctcag atagttggct tctcatttgc c                        101

<210> SEQ ID NO 32
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 32
gagcaagaga ctgtgatgag gttcctgtgc tgtgaaatgt tgtagaaaga ntctgatggt     60
ccacaaactg aggagaagag tagttctgta tctgaggctg c                        101

<210> SEQ ID NO 33
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 33
tcacggtggc tgaaaaaact tcgggatcag cataaaagat ccaccggagg ngaggtgttc     60
ggaggaggga aacatgcgac gggatggtgg cttccgggga a                        101

<210> SEQ ID NO 34
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 34
aggtcagaat cagtgacacc tggataaaac gacctggaga ctgactgaga naagtccagc     60
tcgacgattt gagtgaacct gagggcgaga cggccaagca a                        101

<210> SEQ ID NO 35
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 35
gttcctatcc tttgcaagag cgtgatcccg gtgtctatac cggtgattct nctcaaggta     60
ggcacgagga cgcggtcgta gattatgatg aaaacagtca t                        101

<210> SEQ ID NO 36
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 36
gtctataccg gtgattctcc tcaaggtagg cacgaggacg cggtcgtaga ntatgatgaa    60
aacagtcatt cccgtcatca agaagaccac ataggtggct g    101

<210> SEQ ID NO 37
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 37
agtccaacgc ggtcgtagtc aacgggatcg ttgaccgctc gttggtgaga nacagccgtt    60
gacgcgatta cgttgcggtg agtgaggaga acgcctttga c    101

<210> SEQ ID NO 38
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 38
tcgttggtga gagacagccg ttgacgcgat tacgttgcgg tgagtgagga naacgccttt    60
gactttcccc gtggtcccgg acgagaagag aatcgctgca g    101

<210> SEQ ID NO 39
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 39
cttggtattg tgcagtttat cccaacacgt ttgactctgg attcagcggt nacaaggcca    60
ccaccgctat tgtgtgaagc tgacttactg agttgcatgg a    101

<210> SEQ ID NO 40
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 40
gcggtaacaa ggccaccacc gctattgtgt gaagctgact tactgagttg natggacaag    60
gtgagtaaaa ctgtcttgtt tgcccctctt ttcatggtgg t    101

<210> SEQ ID NO 41
<211> LENGTH: 101
<212> TYPE: DNA
<213> ORGANISM: Brassica oleracea
<220> FEATURE:
<221> NAME/KEY: misc_feature
<222> LOCATION: (51)..(51)

<223> OTHER INFORMATION: n is A or C

<400> SEQUENCE: 41
gcctcctcgt tccagcgttg taacgagaca caaaacgctt tagtgagact ncacaacagc    60
ttgttgcaac aagccgtgat aaagctcaat aacgaagcca a    101

<210> SEQ ID NO 42
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 42
gtcgtctctg ccctccccgg cgggttcaac gagatcgatc ccgtcgccgt ngtcgtggtc    60
ctcgcgatca ccgtcatcat ctgctgcagc acgagggaga g    101

<210> SEQ ID NO 43
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 43
gtggttgaag gacagccaac gcagccagag caaggtaacc aagccacgtc nctactcgtg    60
tccatggcca ggagtagagt ctgagccgga gttccgatct t    101

<210> SEQ ID NO 44
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 44
gccacgtcac tactcgtgtc catggccagg agtagagtct gagccggagt nccgatctta    60
gccttgacaa tgtacgttgc gctctgcagc atttgacgcc c    101

<210> SEQ ID NO 45
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 45
cgggtgtggg agccggagga gaggcagcag agtcggtggg tgcctcgcca naatcactgg    60
gactagccgc ggagtagtca tcctcagcag cgggtccttc t    101

<210> SEQ ID NO 46
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 46
tctgtttaga ggcagtggac ttgagtttcc ggtctggctt caccgtctca ncgcgtttag    60
gtttagcgtt cttgtccaca ggagaagact tctctgcctc a                       101

<210> SEQ ID NO 47
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 47
ttgaacttgc cgtgtttgaa cttaccgtga ccatgatacc cgtagccata nccgtgacca    60
tggtggtgac catagtgtcc gtggtgagac atatggtgag a                       101

<210> SEQ ID NO 48
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 48
gtgaccaagc taacaaagcg agtccaggaa tgttccaatt ctgtgtccac ncaagagctg    60
aataaagggc atgagcttat tcaccaaacg ccaaaacaaa t                       101

<210> SEQ ID NO 49
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 49
gctggtcgga actcatggag agtgagtaaa ttttcttctt tacacgagaa ngaatccatc    60
catggctcaa atcttgatcg gtttcagggt acgttgaaga a                       101

<210> SEQ ID NO 50
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 50
agtcaccgga gaggacccgg gttcaacggg agccactcta gtaatagtag naatacctgg    60
gggaggttcg gcgggaacag cagggcggtt gtgacgaaga c                       101

<210> SEQ ID NO 51
<211> LENGTH: 101
<212> TYPE: DNA
<213> ORGANISM: Brassica oleracea
<220> FEATURE:

```
<221> NAME/KEY: misc_feature
<222> LOCATION: (51)..(51)
<223> OTHER INFORMATION: n is T or G

<400> SEQUENCE: 51
agttggatcc tcaacgtttg ccttctttgg gttcaacggt aatgacattc ncaatctcat      60
tacttttctg aataaagctt ttttcttatt gtgtgaaact a                        101

<210> SEQ ID NO 52
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or A

<400> SEQUENCE: 52
ctgcagatta ttgttcaata cactatacta ttgggaggtg gctgtaaggt nttatgggca      60
ttgaaggtgg gaacacaagt tcaaaatctg gaaatgtgga c                        101

<210> SEQ ID NO 53
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 53
tctcctgcat cgaaggtcca gtgaaccgca tagtgtgtac gttcatttgt ntgaaacgcc      60
agagaggaaa tgtaaccatt gtgtatctcc ccgcatatcc c                        101

<210> SEQ ID NO 54
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 54
gcggcacaaa cggagcagga tcttacttct gagaagagag tatgcgttcg ngatcgattc      60
accttttgct agggatcgat ttcctggctt agtatacttt g                        101

<210> SEQ ID NO 55
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 55
agccaatgag cttgtggact tcatggaagc ctctggggat cttctggatg ncaaagcaat      60 ggcgtctttga gtcgaagggc attgcgatgc caaagatctc g                       101

<210> SEQ ID NO 56
<211> LENGTH: 101
<212> TYPE: DNA
<213> ORGANISM: Brassica oleracea
```

```
<220> FEATURE:
<221> NAME/KEY: misc_feature
<222> LOCATION: (51)..(51)
<223> OTHER INFORMATION: n is T or G

<400> SEQUENCE: 56
tgttggagag tgcagtttat gactctaatg ccgctgacat cctgttcgtt nccgtacctt      60
ccaaggcttc cgacactgat tccatgtcct ggaccgcagg t                          101

<210> SEQ ID NO 57
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 57
agagtcttcc ttggggttgg agttggtgac gacaggtccg ctacagtact ncctgccgga      60
ctcaccggat ccgtcgccca acccttctcc atatctggtt c                          101

<210> SEQ ID NO 58
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 58
ttcttctcag tggcactacc atttgctgca gaagctctga gaagaggctc naagagcttg      60
cttgccacat caggaggcaa agcgtcttca ccgggaagaa c                          101

<210> SEQ ID NO 59
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 59
ctagcatcaa cctctgtccc gccagtccct gtcacagctg ctctatcccc ngcctgccct      60
atctcatctg ccctagcccc tgctgcaggt tcttcgggct g                          101

<210> SEQ ID NO 60
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 60
acacatccac aatctcctca aacgaacaac gcctcatgct acggcctcta naatcttgag      60
catagttcct caagtccaaa agctctccga tctgcagctc a                          101

<210> SEQ ID NO 61
<211> LENGTH: 101
<212> TYPE: DNA
```

<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 61
ctccgccgcc actagcgctc ccatttcctc cagctccacc ttccttatcc ncctgtttcc      60
ccgtggtcgt cctctcccct tccacctccc tgtacttctg c                         101

<210> SEQ ID NO 62
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 62
tttggccatg gtgaggggga agctgcaggc gaagaagaag gagacagctg nggagattcg      60
tctgcaggag gtgcgagctc ggatcaaagc tttgaccgag t                         101

<210> SEQ ID NO 63
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 63
cggttcgatc agcttgcact tctcggtaaa gcaatggatg tagaagacca natcgaatac      60
attgttgaag gcctatccga tgattacaag caggtagctg a                         101

<210> SEQ ID NO 64
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 64
gcttcaacac taaggtacta tagaagaact tgtttatgta tgttgcatct ncatacgtgt      60
ctgcgctttg gattcggtca atcattgtat gtatgttgca t                         101

<210> SEQ ID NO 65
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 65
ctgtttaccc aagaacttga tgccaacgac cctgtctttg tcgtatggct naggagaaga      60
ggacatggcc atgttgcaca ccacttcggt ttggtaagtg g                         101

<210> SEQ ID NO 66
<211> LENGTH: 101

<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 66
cattatgttc tgcagcatct gcagtggatc accatggctc accaccagaa ntgcgcacct      60
ttgaaattct gcttccatgg ataacatggc agtggcaagt c                          101

<210> SEQ ID NO 67
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 67
taaactgtat tagctcactt tcagcatcgg ttagtccaga cgagaagaat nacgacttct      60
gaacacttac tgccaagcct gatcgaagct caaatccttg a                          101

<210> SEQ ID NO 68
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or A

<400> SEQUENCE: 68
agtcataagt cttcttcact ctctttgtta cacggtagct tagaacagcc ncaagaaaaa      60
gaacaaagac aaagaacggc acacaaattg ctaagattat c                          101

<210> SEQ ID NO 69
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 69
agaattggtc tgcagccaag cagattcaag cgatggtggc taatcttgtg ntcccacgtg      60
gagcagaagc gatgccggtt tacataatga gcagtgttat g                          101

<210> SEQ ID NO 70
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 70
ccttctcact cgctgcagcg acttctcttc ttcttcatca ctaacaacaa nactaacaaa      60
ctcgtcagct tcttcctcat cacctctctc ggtttcttca t                          101

<210> SEQ ID NO 71

```
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 71
tttgacattg gctcatcagg aggtggaggt ggtgggtctg ttccataggc ngtgatgaaa      60
cggtccagac agttggagtg gaggtggtct gtgttgcaga c                        101

<210> SEQ ID NO 72
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 72
acgtcccttt gttgtcatcc caccagaatc gagtgaatgc agactgtatc ngtttgcaca      60
atgaaaccgg gagcttgaag caagtcatag agtgcgatgg a                        101

<210> SEQ ID NO 73
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 73
agcttccaaa gaaccttccc aaacctaaac cataccaaga atccaagcac naaaccacct      60
aaaacactcg acagcaatga tctccgacgg cacgagagag a                        101

<210> SEQ ID NO 74
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 74
ttatgctgtt ttagcactag tgcttgaccg agcacgacct agagcagcgg nttctgaggg      60
gctaaccatc ctagctgcag ccgctgcctt cagtcaggag c                        101

<210> SEQ ID NO 75
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 75
cggtgagcgt tggggttgat gtcgggttgg atacagagct ttgagccagg nacgaacttt      60
ctcgcttcta caacggtctt gagacctgag tctactctgc a                        101
```

```
<210> SEQ ID NO 76
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 76
agacctcgtg ctccctctg tcgtagttca cgtacacgga tttcttctcc nggagtgcgt     60
cggaggtctt cgctgcagct cgaggacgat aggcgcggga a                        101

<210> SEQ ID NO 77
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 77
ccatctgcga aagcaatccc gagctcaggc agctccatgt tgctctcctc nacaccagac    60
acgttgaagc aagggtctag gatcgggaag tcttcaaaca c                        101

<210> SEQ ID NO 78
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 78
agtgcgaagg atgatgttct caggtactgc attattttct tctttattta nttcagtgca    60
ctacatgtta ctgctttcac ttgcctcatt tcattatttt t                        101

<210> SEQ ID NO 79
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 79
aaaaaaactg caaagttcta tatgaaagtt tgaaagaaga acatatacca ntttgttgta    60
gactctgagt ctttccttga caacttctgc agtgtcatca g                        101

<210> SEQ ID NO 80
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 80
ctgcagcagt ccaactcatt ccccgctaga actggagatc cccaggctac ntcagctgca    60
agcaatccag gtgtctctgg aggacagaag ccgtttgtgc c                        101
```

<210> SEQ ID NO 81
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or A

<400> SEQUENCE: 81
tacgagatca tcctctcgaa actcccttgc aaatggcgcc ccgctttgga ncatgtcatg    60
aaaatcctca accgttagat tcaaggcacg ctgctgcaga a                        101

<210> SEQ ID NO 82
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 82
gagaaggagg aagccttgga gagggttggg agtttgagtg aggaagctga naagagcggg    60
aagagagcgg agaacgcgag ggaacagcta ggagcagcgc a                        101

<210> SEQ ID NO 83
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 83
cagcgagtgc agcaaatcct ataacccgcg tatgcatcgt tgtcaagagg ncatgacggc    60
gactaagagc atcggcgact ttattggttt tgtcggactg a                        101

<210> SEQ ID NO 84
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 84
cctcatttca aactttccc atctctagtc ttcagctcag tgacgatgag ntgatcagtg     60
gcaggaacgg taaagagatg gatgagagtc agagtccaga g                        101

<210> SEQ ID NO 85
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 85
cattacggaa ctttgaagag gtacgagttt gagatgcata gtagagtctc natggcttgg    60
attcttggac ttgggcctag ccttgggctt gttcgtgttc c                        101

<210> SEQ ID NO 86
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 86
ctgaggagtt tggtagtgtc gctaaagcta ctgatagtga tcttgatttc nttgtggttt    60
ctccttcaaa ggctattgag gatgataagg atgctaaggt t                       101

<210> SEQ ID NO 87
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 87
agaaatcttg tcacaattat caaacattcg caacacatta gcaggagatt ngccaagtga    60
gaaactcgtt catgtcgttg agaagcttca atgcaagcca c                       101

<210> SEQ ID NO 88
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 88
tgcggaggcc tgtagttgcg gttttccaaa gcggctgcaa tggctctttc nacggatgct    60
gctgatacgg atctggaggt tctagaggaa ggctttgggc a                       101

<210> SEQ ID NO 89
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 89
acaacgttgc tctgcagata gtgatcatat atctcagact tattagactc naggatagcg    60
agagctgcct ttcttcttca agaactctgg aatctccacc g                       101

<210> SEQ ID NO 90
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 90
cgagagctgc ctttcttctt caagaactct ggaatctcca ccgaaccacc ntctctaaag    60
gaggaagaag gtcttcttgt agctccagtt gaggcagtat c         101

<210> SEQ ID NO 91
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 91
caaaagtaga agcgaaagct atgatgatga ttacaaaagt ctccatcctt ntaaacaaaa    60
tcggcacgta taattatcct agatatgtgt atatataagt a                       101

<210> SEQ ID NO 92
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 92
gttaaggtgt ggcgggtcca cgtcatctca gggaaccgaa gccatgactc naaggcagat    60
catggccgtt gaagatggca gaagaaactt gacgcctgca g                       101

<210> SEQ ID NO 93
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 93
gagggcggta gatctctcag attcctctct ccatctccct cgttttcttc ngtctcttct    60
gctggtggtg aagcaaatag acactctagg tctcttagtg t                       101

<210> SEQ ID NO 94
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 94
ttcgatcagg gatctgcaga tcagaagaga gacgcatgga gcacgtgata ntaggaggcg    60
ttcatgatct cccaggaaac cagaacagtg gagagatcga g                       101

<210> SEQ ID NO 95
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 95
agcgatggga gcatcttgta ccttgatctt ccctccaaca tggtaggatc nttcttgatg    60

```
ggttggttcg gcgtcgtgtt caaagcagac ataaccagag t            101
```

<210> SEQ ID NO 96
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 96

```
tctccgtctg gagtctctgt catgtctccg ctctcgccgt cctccggggg naacgggatg   60
tcgtcgatgg cgtggccgca gccgaacgtt cctgctctgc a                      101
```

<210> SEQ ID NO 97
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 97

```
aaagtgcaac catcatgcat atcgacttta tgatcatctt tgagatggtc nacaagggtt   60
tgaatatcac cggtcaccga acactcggag ccagcgtagg g                      101
```

<210> SEQ ID NO 98
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 98

```
ctcggtgctg cagcaggagg ctggatcaat gactactacg gacgtaaaaa ngccaccatg   60
tttgctgatg ttgttttcgc agctggagca atcgtcatgg c                      101
```

<210> SEQ ID NO 99
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 99

```
agaatagggt ttacctgcaa caagattctc acaagctccg tgcttccaaa ncgagaagct   60
tcaagaaagc attggttcac gttatccgcg cctccttcca c                      101
```

<210> SEQ ID NO 100
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 100

```
gtcaaccgtg tggagctgct agccaagaaa atcacagagc ttggttactc ntgcttctat    60
atccatgcga agatggctca agaccaccgt aacagggttt t                       101
```

<210> SEQ ID NO 101
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 101

```
gacaacatct ctctgatctc accgttcaca acgctctgca catcagcaaa naccttagcc    60
cacaacggct tctcagagac cggtaaatcg aaaagatcat t                       101
```

<210> SEQ ID NO 102
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 102

```
gaatctgtac atgttccttt gtttatatgg agaactcgtc cttcagaccg ngggatgtgg    60
gggaaaggtg tctctacagg tactttcttc tgcagaactc g                       101
```

<210> SEQ ID NO 103
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 103

```
acgacccttg ggatcgggat aaggaacgac actgcacgta gcgatctctt ngttgattcg    60
agctcacggt acgagatctt cgcggcggag tatctcggcg c                       101
```

<210> SEQ ID NO 104
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 104

```
aacaaccatc tctgcaggaa agagatagag agaccataag aactgaactt natatgcata    60
aacatttaca aagtaccttc agcagcatct ccactaccgc t                       101
```

<210> SEQ ID NO 105
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 105
acttcatatg cataaacatt tacaaagtac cttcagcagc atctccacta ncgctagaac    60
catcagcgtt gtcaatctcc atagcaggct gcttaggagc t                       101

<210> SEQ ID NO 106
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 106
tcacggaggg cagtcgcagt tgaatcatct attcccagca gatactgtag nctcgacacc    60
ttttctggcg ccggcttggg atcactcttt gaatagatac t                       101

<210> SEQ ID NO 107
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 107
gcgaaatgga cagcagtaaa aggcgcgttc atgagaacag tcgtcctata ngaagcgtag    60
aacgcaccaa acccttcctc cctcataacc ctcctcacgc a                       101

<210> SEQ ID NO 108
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 108
catagaaaag ccacgagcga agcaacctct tcaggctccc cgaaacgccc naacggcttt    60
ctagacgtta cagccttctt gaagtcatca tcgtatacct g                       101

<210> SEQ ID NO 109
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 109
ctatgatgat gtcctcgccc actgtctccc aagacgctcg aataaactca nctgagtagc    60
catccggtca cgggctcttg ttcagtggca tagagaataa t                       101

<210> SEQ ID NO 110
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C ot T

<400> SEQUENCE: 110
acctggacca ccaccatctc cagcgcctac tgcagaaacc acagacacat ngtcacctgc    60
cgcaccacaa caacaaccaa cacgatgag caccagaaac c                         101

<210> SEQ ID NO 111
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 111
taccgttagt gctctgcttc ggtttattcc tcaacttttg gcaagcgtca ngaggatcag    60
ccacgtaaag gactccggtt tctaccgtag cctcttctga t                        101

<210> SEQ ID NO 112
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 112
tatacgcaat cctgcagcat aatgaacatc agtaggagct tggagaaact nactcagtct    60
gtgaacagta aaggttatat ctggacgagt aatagtcaga t                        101

<210> SEQ ID NO 113
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 113
agtcatcggg cgtggaccat gttagcgaac tcgcgcttgt ctctgccttg nactgacaag    60
atttgatggc ggagacggta tcgcagcagt attgtgatcc t                        101

<210> SEQ ID NO 114
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 114
cctgcagaag gtggagacca gaccactctc gaagctgatg ttgtcctcgt ntcagcagga    60
agatctccct tcacatctgg acttgatctt gacaaaatcg g                        101

<210> SEQ ID NO 115
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 115
tcccgagttg gctgcaggcg tacaccacca gatgtaacaa ctgtttccag nagcttttcc    60
tcacgggttt tgctctcaag acgaactgaa cccgaacttt c    101

<210> SEQ ID NO 116
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 116
ctggtttcga tgatctacga aaagggcttg acacttcctt gtcactcgaa ncaaggacac    60
accagcggcg agatcataaa cctcatgacg gttgatgcag a    101

<210> SEQ ID NO 117
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 117
tgtatcagcc gcctatctgg aaaatatact tgtctcctaa caatcgcagg nctaatcgga    60
gacagaagag gtgacaatag atctgtaact ttctccttgt a    101

<210> SEQ ID NO 118
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 118
ttggaactta ttactgtgtt tttttgtttc tgtgggagca gggatgagag ngttaccaaa    60
gcagcggttg cagcaatggg tgatctggca gatgttgtag g    101

<210> SEQ ID NO 119
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 119
gcagatcctg gcttcggcga acaatacact gcctccaaag ataacgccag nggattacag    60
agctgaagtg cgccgaggat tgctgactcc aagaagttct a    101

<210> SEQ ID NO 120
<211> LENGTH: 101
<212> TYPE: DNA
<213> ORGANISM: Brassica oleracea
<220> FEATURE:
<221> NAME/KEY: misc_feature
<222> LOCATION: (51)..(51)

<223> OTHER INFORMATION: n is C or T

<400> SEQUENCE: 120
aatgtgttta ctgtgctgtg ctcgacgctg agccatgcag tgcgaacggg naagaaaagt    60
caaggcacgt ctgaatctgc agccaaggaa cctgaggaat c    101

<210> SEQ ID NO 121
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 121
atcccatccg atttgacgga gacgccgaga gattcatcct tcgtcggcgt ngtcttctcc    60
aagctctctt gattgaagaa tctctgaaga cgaaatggcg t    101

<210> SEQ ID NO 122
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 122
tcgtcggcgt tgtcttctcc aagctctctt gattgaagaa tctctgaaga ngaaatggcg    60
ttctggtggc cgctgatcgt tctcgccttc gcttacgcga t    101

<210> SEQ ID NO 123
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 123
gcggtgacgg tgacgccgcc gccgacaagg cggccaccgg ggaggccgcc naagaagaaa    60
acgccggcgg aggaggtgat gaagcggcag ctgcagtgta g    101

<210> SEQ ID NO 124
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 124
gacagagaag agtgcctgac cacgtggaga agagcgtaga cgaaaacgct ngaaggtgcg    60
ttccctttgt ttgcttcagc tatgagatcc ccatagctgc a    101

<210> SEQ ID NO 125
<211> LENGTH: 101
<212> TYPE: DNA
<213> ORGANISM: Brassica oleracea
<220> FEATURE:
<221> NAME/KEY: misc_feature

```
<222> LOCATION: (51)..(51)
<223> OTHER INFORMATION: n is T or G

<400> SEQUENCE: 125
gggatcagga gcagtatcag ttgcaacacc aggctcatgg tgaggcacaa natcacgatg    60
gaaatgatgg gggagatcaa gttgatgaag gtgaggaagg a                       101

<210> SEQ ID NO 126
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 126
cccagtgccg tcaccaaagg atggaaagcc aatcctgttg aatttgattc ngtcttcaac    60
aagagcagac acacgtttgc ttatggcagt ccagatatca t                       101

<210> SEQ ID NO 127
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 127
tgaaaacagc attccacact cacaacggtc actatgaata cctagtgttg nccttcggat    60
tgtgcaatgc cccatcgaca ttccaggcgt tgatgaactc t                       101

<210> SEQ ID NO 128
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 128
tttctgaggt catactgtcg attgatgctg aggtcggatc tccagtgctc ngctctccag    60
atccatgatg ttcatctctc tttgccattc tgaggtcgtc a                       101

<210> SEQ ID NO 129
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 129
tcgtagtttt cgttctgatc atcaaaaccg aagaagtctt gtatgggaag ngagctagtc    60
gtgaatgacg tgtcaaagtc atcatcgtcg ccaaggattg t                       101

<210> SEQ ID NO 130
<211> LENGTH: 101
<212> TYPE: DNA
<213> ORGANISM: Brassica oleracea
<220> FEATURE:
```

```
<221> NAME/KEY: misc_feature
<222> LOCATION: (51)..(51)
<223> OTHER INFORMATION: n is G or T

<400> SEQUENCE: 130
aagtgcatgg gctagcatcg tagctgcagt ttccgccatc aagttgtgtg nttcgccttc    60 aagtacccctt tgtcttcttg tttcactctc caccgggtct g                      101

<210> SEQ ID NO 131
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 131
aggagagttt cgtggttttg atggacgtat ctgagagtaa gcctgcctcc ngtcaaacgc    60
aagagcaaag gtataaccga accatcatcg ttgttcgcaa c                       101

<210> SEQ ID NO 132
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 132
atactttgat ggtgcaaaga ttgaatgcag aggtatggct tttttagtcc ngtcccttct    60
ggattgaata gacttttagc tactgctgca gatttgttca t                       101

<210> SEQ ID NO 133
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 133
gttgtttcgt gcaaatctca ctgctgcagc ttgagcattc gtcatagtct nggaaggttg    60
agttgttgtt gcagtcatac caaggaccgg cgtcttctct t                       101

<210> SEQ ID NO 134
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 134
cattcgtcat agtctaggaa ggttgagttg ttgttgcagt cataccaagg nccggcgtct    60
tctcttcttg tcgcatagca ttcagatggc attcttcttg a                       101

<210> SEQ ID NO 135
<211> LENGTH: 101
<212> TYPE: DNA
<213> ORGANISM: Brassica oleracea
```

```
<220> FEATURE:
<221> NAME/KEY: misc_feature
<222> LOCATION: (51)..(51)
<223> OTHER INFORMATION: n is G or A

<400> SEQUENCE: 135
ttcccatcaa caacctttgt aggatcagca agcgccgcct gagcaccttc ngaagtctta      60
tacacaaaca aagcaaaccc tcgtgacttc ccagtgactt t                        101

<210> SEQ ID NO 136
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 136
ataacaacag atccgtctgc agctattccc caatacaaac tctcagctcc ntcagatcct      60
agagctgcga aaacagagga ggtctgagca tcatagacaa c                        101

<210> SEQ ID NO 137
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 137
atcttgatct ctctgcagat ctggccacga acagtgtcat cgtggttacc nttgattatc      60
ttgagtgcgt atacgcggga ggttggacgg tggactactc t                        101

<210> SEQ ID NO 138
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 138
atagcaaacc tgttggtgta gtactgatct tgacaattat agccagccaa ngttctgggt      60
cgaccagaca taacatcttc agcagctgca gcctcaacat t                        101

<210> SEQ ID NO 139
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 139
aaatatgcga tccgaatccg aacggatacc cgaacgtcga cccctagctc ngaaggacaa      60
tgaaaaccaa tcgattcagc ggcatagagc catagaggaa g                        101

<210> SEQ ID NO 140
<211> LENGTH: 101
<212> TYPE: DNA
```

<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 140
gccattctcc atcgaattga acaaggtctc gttatcgatt tggagccagt nagtcctgat    60
gaggtcccag tcactgctgc tggtgcgttg aagtcataca a                       101

<210> SEQ ID NO 141
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 141
tgcagtgaga gccaatgatg aatgggtgcc ctactcacca tctcaagctg ntgtgtctga    60
cacaaaagcc cggggaatag ccacacaggt tggtcttact g                       101

<210> SEQ ID NO 142
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 142
gtagaaaaga ggggaagagt atttatgagt gagcaaacac ctatctatcg ngattacaaa    60
ttagtaggaa taaagtgctt gccttcccaa agtctatatc t                       101

<210> SEQ ID NO 143
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 143
aactttctct tgagaaacaac cgcaaacacg agcgggaaga gttggttttc ngcatcaaac   60
cccgcggcga ctagcagttt tccggagtgt ttaccgcagt c                       101

<210> SEQ ID NO 144
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 144
aaacatgaga ccacactgca gtagaaattg gcttgcccgc taacgctact ncaaataatt    60
gatgccatac ccagacagct ttgcagacct cagtcgaaag a                       101

<210> SEQ ID NO 145
<211> LENGTH: 101

<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 145
gcttatgagt tgtgtgtttt tttctatctc agataagttg tattgggacc ntgcggctca     60
tgttggaaca aacacaccag gaggactggt actagtagcg t                        101

<210> SEQ ID NO 146
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 146
ctgctacacc cacctcttca ttcccatggg gttgaagtac tcctccttgg ncatcgaacc     60
cgttgctgtg aggcggtgct tgtgagttca tctctatctg t                        101

<210> SEQ ID NO 147
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 147
ctatctgcag gagccctaat actgacacgt gtaatctcaa atattccac ngcgaagaag     60 ttgaggtgac ccattttgct gttgatagat ttgatgcggc t                        101

<210> SEQ ID NO 148
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 148
ttagaacacc tgtgctgccg cactgtggtc aaggcttctc tcagagccaa ngcttccgcc     60
atcagaggtg aggctacata ctctgctcga gcttgaaact c                        101

<210> SEQ ID NO 149
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 149
gcagtatact ctggtatggt gatacctctg tactttgcag ggctttcatc ngacaaaagc     60
tctttgatcg gttcataaac cgtgtcattt ggaaacagac t                        101

<210> SEQ ID NO 150

```
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 150
tcatcgctca cgtcactgct cgtgcttcct ctgtagatac tgcttttgcc nctctccatg    60
aaatcaaggc ggcttccact aagcttggcg cttccgctcg t                      101

<210> SEQ ID NO 151
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 151
tcgttaccgg tccgagcgcc gtcgctggtt tcttcccgga gaatcttcca ngagaaactc    60
cacgaacttc ccaggtgcgc caatttagcc caagtgaagc a                      101

<210> SEQ ID NO 152
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 152
gaacggttag tttctccact aatttctcca aattcagaca cgggtttggt nttattcaga    60
catgtggttt agtcaacgta aagctaaaat gggtaaaaga c                      101

<210> SEQ ID NO 153
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 153
tactgcagag atgcgcaaag ccgaggtcac gtgaggccaa gaacttgata nagaagcaga    60
gcctagctct tttcggtccc gagggaaagg aggaagagag c                      101

<210> SEQ ID NO 154
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 154
gggtttagta caatagcctc tgcagttggt taccctgtcc actctgagtt ngctgacctc    60
aagacataca cgaatggtgt gataaagctt cgtgttgtag t                      101
```

<210> SEQ ID NO 155
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 155
aacatgagtg tcctcttctc tccgaggaac ccggatcgtg tcccgattcc nacactgaga    60
cgtttctttg gtgacgatta ttacatctgc aggtttcagg t                       101

<210> SEQ ID NO 156
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 156
ctgcagtata tttttggaa tcacactctg caaatctgat ctttcttgtt ntctttctct    60
atcccctaat ctaaaagata ctatcaacga agcgaacttg c                       101

<210> SEQ ID NO 157
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 157
tcactgcagt gagtctcata aagtaccatt ttattttgat tacaggctgg ngttctggct    60
ggagatgtga gcgacattgt ccttctcgac gtgacgccgc t                       101

<210> SEQ ID NO 158
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 158
tcatcaagtg gcaccataag agggttcgcc tcatccatct ctacattcat ntctgaatcg    60
taatctagtt tcatttcttc atctccatca ccctcctgca g                       101

<210> SEQ ID NO 159
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 159
attttgagat gtctggactg tttcatcctg atcagatccg gttggtggcg nctgaacagg    60
aggagctgcc cggcttaggt tggttgagga agctgcagca g                       101

<210> SEQ ID NO 160
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 160
ggtaaggctt ctcgaggaac ctcgtgtaga gtgtaagtga gaaacgaggg nttggggttt    60
actactattc ttggacattc gatggacagc atctccaatg a                        101

<210> SEQ ID NO 161
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 161
gtgtaagtga gaaacgaggg cttggggttt actactattc ttggacattc natggacagc    60
atctccaatg agtccttatc aattcgtggc tgcagaagaa g                        101

<210> SEQ ID NO 162
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 162
agccacaaag aacgagaaat cacttctttc cagtgcttgt gggagatttg ngcatggaga    60
tacagagatc agaagccacc tgatgtttgc tcatgagatg g                        101

<210> SEQ ID NO 163
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 163
gtgaacatgc catccacttc gctgtctcct gcgggtacct caaaaagaaa ngtcggacaa    60
tcaggtttcc ctccggaaac cacaaatgct gggtatgaaa g                        101

<210> SEQ ID NO 164
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 164
tgaaactcat atggtaatat aattttttt cttcctcata ttcattctgt ntcactttga    60
ggcttgatga atgagtgtct tgtgacaggt ggaactagag g                        101

```
<210> SEQ ID NO 165
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 165
acacgcattg gtaacctctc gttctgaaca gcgtgcgcgc aagcttctac ngatagcttc      60
ctacagtcca ttagcctgca gattctcttc ttctcgctct t                        101

<210> SEQ ID NO 166
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 166
ggtggtggtg ctgcaggagg cggcggaggt acggtagagg gtgatggagg nacagcgaaa      60
ggagctttct ccgtcgtcac aaagcctcgc ttcttcaacc c                        101

<210> SEQ ID NO 167
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 167
gtgcaatcag ctgagaagtg accttgcttg taacagttgt tgcagagtct naggtcacca      60
ggagggaggt ggcgagccgt gcagtcttta gcttggtgtc c                        101

<210> SEQ ID NO 168
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 168
atcccgagta cttgactctc tgcctgacca cggtagactt gattctcaga nattttttga      60
cgccagagac atggttccca attatacaga gtcatctccg c                        101

<210> SEQ ID NO 169
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 169
caggttcctg gagggacaac actgttggag catttgcaag gtaaagtttc natagaagag      60
```
agtgtgatga gtgctgcagc agaagctgtg agggcagcaa t                                101

<210> SEQ ID NO 170
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 170
atgatttcgg aaaagaagca gaagctagag ccgaagagaa ggagacaaaa ncgatgagct           60
ggagaaggaa atggtagtga ccttcaagac ctaagtgatc a                                101

<210> SEQ ID NO 171
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 171
cgccgaaccc tgatcaaccg agatcggtgc aggaagccac cgttgagacg ngtcgtccaa           60
tctctgacgg atctcagcct caataaaaag ggctgcagat g                                101

<210> SEQ ID NO 172
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or G

<400> SEQUENCE: 172
tgaccgcaag cacatctgac atctcggccc gttgagagat ccatatggcg nactcgaatc           60
ttgccccaac tgcagcgcct gtaaccccac acatttttta a                                101

<210> SEQ ID NO 173
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 173
accactcgtt tccaatgacg ctattcgttc ctcggaccac acatctggat naccgcacgc           60
tggaacagct caataactgg acgtggcagt tctgtgttat c                                101

<210> SEQ ID NO 174
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 174
gctctactca tctgctccag cctcaccgcg ctaatgggag ggagactagt ngcagcgcca           60

```
acgctttggc ctgagttact acctcctcct gttgttaaac c                          101
```

<210> SEQ ID NO 175
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 175

```
atatgtactc cggcgagtgg aatttagtga aatctgaatg ttgggcaggg ngagggcgga      60
tgatatccat gtagcgaggg aggtaatagc tgcagatgag g                         101
```

<210> SEQ ID NO 176
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 176

```
tagatgaaag ccaaggtaga gaaagggcaa taaaccaagt atatgagatc naacaagacg      60
ctagatatga acttgctgaa ggagctgcag ctcctggaat a                         101
```

<210> SEQ ID NO 177
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or A

<400> SEQUENCE: 177

```
ttctgccagt cactttatca tagataacct acaaacaaaa ccaaacccca nttcatcata      60
aattcaaaac aaaaccaaat ctcaaattat cttcaaagac c                         101
```

<210> SEQ ID NO 178
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 178

```
acgaggccat ggtcagaatc agctgcagct ggatcagctg gttacgttga ntgtccagct      60
gtatgttcac gtaatcttcc gtgtcgtcaa tgtattccct c                         101
```

<210> SEQ ID NO 179
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 179
catgttcact attatcattc tgcacgcttg ttccatcctt agccacagat nctacaacat    60
tgtcatcacc tgttttagct tctctctgca gcagaacaag a    101

<210> SEQ ID NO 180
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 180
aagaaagaaa agctcctcgc cagctgagga ggaggaagca gcggaccttg ngggtacgt    60 gtgcggggtc ctcgggagag atctatcgga ggatccttgg c    101

<210> SEQ ID NO 181
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or G

<400> SEQUENCE: 181
ataatcgttg cggtggcggt tccagtttcg ccgccggacc agcactcgcc naggttggga    60
cacttagcct cctcgcagac ggtgtgaagg ttaaggtctc t    101

<210> SEQ ID NO 182
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is T or C

<400> SEQUENCE: 182
cgtcgaacct cggtttagca cgcaaccagt ggtacaacac atccagccat ntcgggaaga    60
agaacctctc catcagatca gccattaggt gtatcggcac t    101

<210> SEQ ID NO 183
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 183
aatccagaag ttgaaaagaa agcgagatct ttggctataa cctcactatc ngatcacact    60
caactctgtt tttggccctc aactgtcgca gccgggcttg t    101

<210> SEQ ID NO 184
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or A

<400> SEQUENCE: 184
aggaagctag aatatctaca cttgtgggat ttgcctgagc tgatgagcat ntactggagt    60
cctttgccgt ttccgtattt gagtctgatc aatgtacaaa a                       101

<210> SEQ ID NO 185
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 185
gcgtggagaa catctccacc gaagtcctca agtccttcaa aatccggcac nactttctca    60
gcattctctc ccgtagccac cacaagcgtc ctgcagatat a                       101

<210> SEQ ID NO 186
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 186
ttgtcgatca aggaagagga cagtcaaact gagcggggag atgaagatag ntttgataat    60
gaacaaccac caagtcctcc tatgcattta tctgcagggc t                       101

<210> SEQ ID NO 187
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or C

<400> SEQUENCE: 187
ctcccggttg atcatgttct gaagttccat gaatgcttgt tcccatggaa nctcctccat    60
ctcctttgga atggttagat acaatatatt cttggaagaa c                       101

<210> SEQ ID NO 188
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 188
tgcttcctcc tttcactgcc gttttccctc gttagcggtt acatcctccg naccccgcc    60 gctgagaaac ttgttgaaag tctcggcgtc gggaacagtg c                       101

<210> SEQ ID NO 189
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 189
gagaagaaga gctagaggca gggtttccca gaagtgactg tgaatcagaa nagctgtaca    60
agtaagcagg ttgaagcaag ggtgcgtttg aagcagggat g                        101

<210> SEQ ID NO 190
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 190
taagtgagac agttgttaca gttttctca gacaagtctg gcgtgcactg nacggaagcg    60
aagaatctag tgtaaggtgg agaagcagga ccatctcctt g                        101

<210> SEQ ID NO 191
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 191
ttctccttct cacgtaaccg atcctctaaa cgatctttgg ctgatctgag ngagaggagg    60
tttctcttca gctgcagatt ctcggtttct gcatctatca a                        101

<210> SEQ ID NO 192
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 192
attgaggtgt ctattcaggg tgagcagttc accaagacct tcaaagtgga ncttttgcca    60
aagatttatg agacactaca gaagttggtt gggctgttga a                        101

<210> SEQ ID NO 193
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C orT

<400> SEQUENCE: 193
ctgcagaatc aacagtctaa gctggtgtct gaagaccaca taaatctcga naacaaacaa    60
aacatagcta catatttctc ttacccgact agtgtctaca a                        101

<210> SEQ ID NO 194
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 194
gggaaagagc ctctggctta gctaaagacg tcatcatctg ctcgagctgc ngtttcagtt        60
cctcgaggtg ggatagagtt tgtttcacag cctccatagc t                           101

<210> SEQ ID NO 195
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 195
ttcttgtaca tgataacgtg gtggcatcca tcttctttgg cttgagccgc nttctcattg        60
gtcgagacag ttccaatgac ggtagctcca agcgcatttg c                           101

<210> SEQ ID NO 196
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or C

<400> SEQUENCE: 196
ctctactcca accgcaactg cagtctgcaa gaaaccaacc tttcaagaac naaaacctta        60
ccaacaagca tagaagaagt gaaggagaga tgaaaggacc t                           101

<210> SEQ ID NO 197
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or A

<400> SEQUENCE: 197
tgaagacggt tacgttgtga ctaagcctgg tactacgaag acgagcgtgg ntggtgtgtt        60
cgctgcggga gatgtgcaag ataagaagta caggcaggcc a                           101

<210> SEQ ID NO 198
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 198
ggaggcgttc tctccgcgct tgcaacgttc aggattcttc aggagccgct naggaatttt        60
cctgatctgg tgtcaatgat ggctcagact aaagtgtctc t                           101

<210> SEQ ID NO 199
<211> LENGTH: 101
<212> TYPE: DNA
<213> ORGANISM: Brassica oleracea
<220> FEATURE:
<221> NAME/KEY: misc_feature
<222> LOCATION: (51)..(51)

<223> OTHER INFORMATION: n is T or G

<400> SEQUENCE: 199
tagcttctta ggtccacttt ttgtgcacac tgctcttcaa acaggtggct ncatgtcctc    60
ttactccctg ggctcttgct tgtctgtctt tctagcttgt t                        101

<210> SEQ ID NO 200
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 200
tttgacccgc cggagacttg acaaaaggaa ccagggcagc cgaggatgat natctcgtct    60
tcatctgttc tttgcctaaa cctgagttga gtttagctgg t                        101

<210> SEQ ID NO 201
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 201
cttccgcaga atcagcttta taatggtcat caagcaacac agcagcatca ngcacaacaa    60
acatctatgc atcatttgca accccaagta gtttcgggat c                        101

<210> SEQ ID NO 202
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 202
attgtagtga ccatttccat ctctctcttc accatcatcc ctcttctcta nccttttgtt    60
gaagacccta acttcttctt caagcaacaa catccaagtc a                        101

<210> SEQ ID NO 203
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 203
aagaagatcc agtcgatgaa ggacaagaat ctgaggtcgg agatggagac ngtcaccagg    60
gacgcgagga ggctcgcggt ttcgtactgc aggattcacc t                        101

<210> SEQ ID NO 204
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or G

<400> SEQUENCE: 204
ttcaatgcgc ttgctatcaa gagattgaag gagattcagt gttaccgtgg ngttaggcac    60
atccaagggt tgccgtgtcg tggacagaga accaagaaca a                        101

<210> SEQ ID NO 205
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 205
aaggaagcag gctttgcacg aacgtcggtt ggcacttgaa caagatgtac naaccttctc    60
ttgagttttt gtgtttctat tctccaattt ttattcataa t                        101

<210> SEQ ID NO 206
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is C or T

<400> SEQUENCE: 206
taacaaacgt accttacaaa tggcaaggca gggtcagcac agcgagttcc ngaaggcaat    60
ctatccgctg aatttgcaag ggagctagca agaccatttt g                        101

<210> SEQ ID NO 207
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or T

<400> SEQUENCE: 207
tccttttcag ctgttttagc acttcgtcca cgtcccsttc cacgccctct ncctctaccc    60
cttccactgg gtcccacttg ccccgtctca tgctgcagtg a                        101

<210> SEQ ID NO 208
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 208
gtcacctctc agcaggaatc gattcaagag ctctacgctg agctcgacga ngagagaaac    60
gcggcttcca cggctgcgaa cgaggcgatg tctatgatac t                        101

<210> SEQ ID NO 209
<211> LENGTH: 101
<212> TYPE: DNA
<213> ORGANISM: Brassica oleracea
<220> FEATURE:

```
<221> NAME/KEY: misc_feature
<222> LOCATION: (51)..(51)
<223> OTHER INFORMATION: n is T or C

<400> SEQUENCE: 209
cctactatcc taaggttagt ctcgatgttc ccagcaacct ttcttagcaa nccggctcta        60
ccaatcaagg cggtgcttgc cgcctcgaac gaagaatgcc a                          101

<210> SEQ ID NO 210
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is A or T

<400> SEQUENCE: 210
ttaaacaaca ggggaagagg tggttttacg gggcggcctc gtggtggttt nggcggtggt        60
aatttccgag gtggtagagg aggcagggga ggtagaggag g                          101

<210> SEQ ID NO 211
<211> LENGTH: 101
<212> TYPE: DNA
<213> ORGANISM: Brassica oleracea
<220> FEATURE:
<221> NAME/KEY: misc_feature
<222> LOCATION: (51)..(51)
<223> OTHER INFORMATION: n is G or A

<400> SEQUENCE: 211
gcatctgaca tcattgtcga gacagcagag gcattcctgc caaaactcgg ntctgcacgg        60
cttgtcctgg ttgacttgag ccatgggtcg aagattctgt c                          101
```